US008580270B2

(12) United States Patent
Morrison

(10) Patent No.: US 8,580,270 B2
(45) Date of Patent: Nov. 12, 2013

(54) RESPIRATORY SYNCTIAL VIRUS (RSV) SEQUENCES FOR PROTEIN EXPRESSION AND VACCINES

(75) Inventor: Trudy G. Morrison, Northborough, MA (US)

(73) Assignee: University of Massachusetts, Boston, MA (US)

( * ) Notice: Subject to any disclaimer, the term of this patent is extended or adjusted under 35 U.S.C. 154(b) by 241 days.

(21) Appl. No.: 13/121,848

(22) PCT Filed: Sep. 30, 2009

(86) PCT No.: PCT/US2009/005383

§ 371 (c)(1), (2), (4) Date: Jun. 3, 2011

(87) PCT Pub. No.: WO2010/039224

PCT Pub. Date: Apr. 8, 2010

(65) Prior Publication Data

US 2011/0236408 A1 Sep. 29, 2011

Related U.S. Application Data

(60) Provisional application No. 61/101,340, filed on Sep. 30, 2008.

(51) Int. Cl.

| | |
|---|---|
| ***C12Q 1/70*** | (2006.01) |
| ***A61K 39/295*** | (2006.01) |
| ***A61K 39/155*** | (2006.01) |
| ***A61K 39/17*** | (2006.01) |
| ***A61K 39/12*** | (2006.01) |
| ***C07K 1/00*** | (2006.01) |

(52) U.S. Cl.

USPC .................. 424/186.1; 424/202.1; 424/204.1; 424/211.1; 424/214.1; 435/5; 530/350

(58) Field of Classification Search

USPC ...................................................... 424/186.1

See application file for complete search history.

(56) References Cited

U.S. PATENT DOCUMENTS

| | | | | |
|---|---|---|---|---|
| 5,344,760 | A | 9/1994 | Harvey et al. | 435/7.5 |
| 5,674,753 | A | 10/1997 | Harvey et al. | 436/501 |
| 5,837,816 | A | 11/1998 | Ciardelli et al. | 530/350 |
| 5,847,096 | A | 12/1998 | Schubert et al. | 536/23.4 |
| 5,851,993 | A | 12/1998 | Jalkanen et al. | 514/10.2 |
| 6,140,059 | A | 10/2000 | Schawaller | 435/7.1 |
| 6,248,327 | B1 | 6/2001 | Daniel et al. | 424/143.1 |
| 6,417,341 | B1 | 7/2002 | Anders et al. | 536/23.5 |
| 6,531,295 | B1 | 3/2003 | Saunders et al. | 435/69.1 |
| 6,566,074 | B1 | 5/2003 | Goetinck | 435/7.1 |
| 6,689,367 | B1 | 2/2004 | Collins et al. | 424/211.1 |
| 6,699,476 | B1 | 3/2004 | Collins et al. | 424/199.1 |
| 6,713,066 | B1 | 3/2004 | Collins et al. | 424/199.1 |
| 6,900,035 | B2 | 5/2005 | Mizzen et al. | 435/69.7 |
| 6,930,181 | B1 | 8/2005 | Pietropaolo et al. | 536/23.5 |
| 6,939,952 | B2 | 9/2005 | Zhao | 530/350 |
| 6,942,866 | B2 | 9/2005 | Birkett | 424/268.1 |
| 6,946,543 | B2 | 9/2005 | Ward et al. | 530/350 |
| 6,991,797 | B2 | 1/2006 | Andersen et al. | 424/248.1 |
| 7,018,637 | B2 | 3/2006 | Chong et al. | 424/197.11 |
| 7,022,324 | B2 | 4/2006 | Binley et al. | 424/188.1 |
| 7,029,685 | B2 | 4/2006 | Lanar et al. | 424/272.1 |
| 7,037,510 | B2 | 5/2006 | Andersen et al. | 424/248.1 |
| 7,060,276 | B2 | 6/2006 | Lanar et al. | 424/184.1 |
| 7,067,110 | B1 | 6/2006 | Gillies et al. | 424/1.49 |
| 7,101,556 | B2 | 9/2006 | Pan | 424/194.1 |
| 7,119,165 | B2 | 10/2006 | Strittmatter | 530/350 |
| 7,122,347 | B2 | 10/2006 | Verheije et al. | 435/69.1 |
| 7,153,659 | B2 | 12/2006 | Harding et al. | 435/6.14 |
| 7,166,291 | B2 | 1/2007 | Morgenstern et al. | 424/275.1 |
| 7,189,403 | B2 | 3/2007 | Despres et al. | 424/218.1 |
| 7,217,526 | B2 | 5/2007 | Terajima et al. | 435/7.1 |
| 7,220,420 | B2 | 5/2007 | Chisari et al. | 424/228.1 |
| 7,223,390 | B2 | 5/2007 | Brown | 424/93.2 |
| 7,238,356 | B2 | 7/2007 | Bosman et al. | 424/228.1 |
| 7,250,171 | B1 | 7/2007 | Tao et al. | 424/211.1 |
| 7,253,254 | B1 | 8/2007 | Sebald | 530/300 |
| 7,262,270 | B2 | 8/2007 | Weissenhorn et al. | 530/324 |
| 7,297,337 | B2 | 11/2007 | Storkus et al. | 424/185.1 |
| 2007/0178120 | A1 | 8/2007 | Morrison et al. | 424/214.1 |
| 2008/0233150 | A1 | 9/2008 | Smith et al. | 424/211.1 |

FOREIGN PATENT DOCUMENTS

| | | | | |
|---|---|---|---|---|
| WO | WO0242326 | * | 5/2002 | |
| WO | WO 0242326 A1 | * | 5/2002 | C07K 14/08 |
| WO | WO 2006/034292 | | 3/2006 | |
| WO | WO 2008/061243 | | 5/2008 | |
| WO | WO 2009/105152 | | 8/2009 | |

OTHER PUBLICATIONS

Rebuffo-Scheer et al. 2011. Whole Genome Sequencing and Evolutionary Analysis of Human Respiratory Syncytial Virus A and B from Milwaukee, WI 1998-2010. PLoS One 6:E25468-E25468(2011).*

McGinnes et al., 2011. Assembly and immunological properties of newcastle disease virus-like particles containing the respiratory syncytial virus F and G proteins. J.Virol.85(1).p. 366-377.*

Murawski et al., 2010. Newcastle Disease Virus-Like Particles Containing Respiratory Syncytial Virus G Protein Induced Protection in BALB/c Mice, with No Evidence of Immunopathology. J.Virol. 84(2). p. 1110-1123.*

(Continued)

*Primary Examiner* — Louise Humphrey
*Assistant Examiner* — Yunus Abdul
(74) *Attorney, Agent, or Firm* — Medlen & Carroll, LLP

(57) ABSTRACT

The invention provides RSV fusion (F) protein ectodomain polypeptide sequences and nucleotide sequences encoding them, as well as cells containing the invention's polypeptide and nucleotide sequences. The invention further provides VLPs that contain the invention's polypeptides, and methods for using the VLPs for protein expression and vaccine formulation. Also provided are methods for distinguishing between subjects immunized with the invention's compositions and subjects infected with RSV.

18 Claims, 24 Drawing Sheets

(56) References Cited

OTHER PUBLICATIONS

Altschul, et al., "Basic Local Alignment Search Tool." *J Mol Biol*, 215(3):403-410 (1990).

Bernsel and Von Heijne "Improved Membrane Protein Topology Prediction by Domain Assignments." *Protein Science*, 14(7):1723-1728 (2005).

Collins, et al., "Nucleotide Sequence of the Gene Encoding the Fusion (F) Glycoprotein of Human Respiratory Syncytial Virus." *Proceedings of the National Academy of Sciences*, 81(24):7683-7687 (1984).

González-Reyes, et al., "Cleavage of the Human Respiratory Syncytial Virus Fusion Protein at Two Distinct Sites Is Required for Activation of Membrane Fusion." *Proceedings of the National Academy of Sciences*, 98(17):9859-9864 (2001).

Haffar, et al., "Inhibition of Virus Production in Peripheral Blood Mononuclear Cells from Human Immunodeficiency Virus (HIV) Type 1-Seropositive Donors by Treatment with Recombinant HIV-Like Particles." *J Virol*, 66(7):4279-4287 (1992).

Hagensee, et al., "Self-Assembly of Human Papillomavirus Type 1 Capsids by Expression of the Ll Protein Alone or by Coexpression of the L1 and L2 Capsid Proteins." *J Virol*, 67(1):315-322 (1993).

High, et al., "Sec61p Is Adjacent to Nascent Type I and Type Ii Signal-Anchor Proteins During Their Membrane Insertion." *J Cell Biol*, 121(4):743-750 (1993).

Karlin and Altschul "Methods for Assessing the Statistical Significance of Molecular Sequence Features by Using General Scoring Schemes." *Proc Natl Acad Sci U S A*, 87(6):2264-2268 (1990).

Kirnbauer, et al., "Papillomavirus L1 Major Capsid Protein Self-Assembles into Virus-Like Particles That Are Highly Immunogenic." *Proc Natl Acad Sci U S A*, 89(24):12180-12184 (1992).

McGinnes and Morrison "Inhibition of Receptor Binding Stabilizes Newcastle Disease Virus Hn and F Protein-Containing Complexes." *J Virol*, 80(6):2894-2903 (2006).

Pantua, et al., "Requirements for the Assembly and Release of Newcastle Disease Virus-Like Particles." *J Virol*, 80(22):11062-11073 (2006).

Singer "The Structure and Insertion of Integral Proteins in Membranes." *Annu Rev Cell Biol*, 6:247-296 (1990).

Winokur, et al., "The Hepatitis a Virus Polyprotein Expressed by a Recombinant Vaccinia Virus Undergoes Proteolytic Processing and Assembly into Viruslike Particles." *J Virol*, 65(9):5029-5036 (1991).

ISR PCT-US09-05383.

NCBI Gen Bank Accession No. CAA26143 (Apr. 18, 2005).

* cited by examiner

```
Novavax F           1 MELLILKANAITTILTAVTFCFASGQNITEEFYQSTCSAVSKGYLSALRT  50
RSV F S2            1 MELPILKTNAITAILAAVTLCFASSQNITEEFYQSTCSAVSKGYLSALRT  50
RSV F B unident     1 MELLIHRSSAIFLTLAVNALYLTSSQNITEEFYQSTCSAVSRGYFSALRT  50
RSV FB              1 MELLIHRSSAIFLTLAINALYLTSSQNITEEFYQSTCSAVSRGYFSALRT  50
RSV F NP56863       1 MELLIHRLSAIFLTLAINALYLTSSQNITEEFYQSTCSAVSRGYFSALRT  50
RSV F B1 cp         1 MELLIHRLSAIFLTLAINALYLTSSQNITEEFYQSTCSAVSRGYFSALRT  50
RSV F B1            1 MELLIHRLSAIFLTLAINALYLTSSQNITEEFYQSTCSAVSRGYFSALRT  50
RSV F A2cp          1 MELLILKANAITTILTAVTFCFASGQNITEEFYQSTCSAVSKGYLSALRT  50
RSV F A2            1 MELLILKANAITTILTAVTFCFASGQNITEEFYQSTCSAVSKGYLSALRT  50
RSV F Pringle       1 MELPILKTNAITAILAAVTLCFASSQNITEEFYQSTCSAVSKGYLSALRT  50
RSV F 9320          1 MELLIHRSSAIFLTLAINALYLTSSQNITEEFYQSTCSAVSRGYFSALRT  50
synthetic const     1 MELPILKANAITTILAAVTFCFASSQNITEEFYQSTCSAVSKGYLSALRT  50
synthetic CAA01     1 MELPILKANAITTILAAVTFCFASSQNITEEFYQSTCSAVSKGYLSALRT  50
                      *** * .  **   *.  .   .* ****************.** *****

Novavax F          51 GWYTSVITIELSNIKENKCNGTDAKVKLIKQELDKYKNAVTELQLLMQST 100
RSV F S2           51 GWYTSVITIELSNIKENKCNGTDAKVKLIKQELDKYKSAVTELQLLMQST 100
RSV F B unident    51 GWYTSVITIELSNIKETKCNGTDTKVKLIKQELDKYKNAVTELQLLMQNT 100
RSV FB             51 GWYTSVITIELSNIKETKCNGTDTKVKLIKQELDKYKNAVTELQLLTQNT 100
RSV F NP56863      51 GWYTSVITIELSNIKETKCNGTDTKVKLIKQELDKYKNAVTELQLLMQNT 100
RSV F B1 cp        51 GWYTSVITIELSNIKETKCNGTDTKVKLIKQELDKYKNAVTELQLLMQNT 100
RSV F B1           51 GWYTSVITIELSNIKETKCNGTDTKVKLIKQELDKYKNAVTELQLLMQNT 100
RSV F A2cp         51 GWYTSVITIELSNIKENKCNGTDAKVKLIKQELDKYKNAVTELQLLMQST 100
RSV F A2           51 GWYTSVITIELSNIKENKCNGTDAKVKLIKQELDKYKNAVTELQLLMQST 100
RSV F Pringle      51 GWYTSVITIELSNIKENKCNGTDAKVKLIKQELDKYKSAVTELQLLMQST 100
RSV F 9320         51 GWYTSVITIELSNIKETKCNGTDTKVKLIKQELDKYKNAVTELQLLTQNT 100
synthetic const    51 GWYTSVITIELSNIKENKCNGTDAKVKLMKQELDKYKNAVTELQLLMQST 100
synthetic CAA01    51 GWYTSVITIELSNIKENKCNGTDAKVKLMKQELDKYKNAVTELQLLMQST 100
                      ****************.******.****.******** ******** * *

Novavax F         101 PPTNNRARRELPRFMNYTLNNAKKTNVTLSKKRKRRFLGFLLGVGSAIAS 150
RSV F S2          101 PATNNRARRELPRFMNYTLNNTKNTNVTLSKKRKRRFLGFLLGVGSAIAS 150
RSV F B unident   101 PAANNRARREAPQYMNYTINTTKNLNVSISKKRKRRFLGFLLGVGSAIAS 150
RSV FB            101 PAANNRARREAPQYMNYTINTTKNLNVSISKKRKRRFLGFLLGVGSAIAS 150
RSV F NP56863     101 PAANNRARREAPQYMNYTINTTKNLNVSISKKRKRRFLGFLLGVGSAIAS 150
RSV F B1 cp       101 PAANNRARREAPQYMNYTINTTKNLNVSISKKRKRRFLGFLLGVGSAIAS 150
RSV F B1          101 PAANNRARREAPQYMNYTINTTKNLNVSISKKRKRRFLGFLLGVGSAIAS 150
RSV F A2cp        101 PATNNRARRELPRFMNYTLNNAKKTNVTLSKKRKRRFLGFLLGVGSAIAS 150
RSV F A2          101 PATNNRARRELPRFMNYTLNNAKKTNVTLSKKRKRRFLGFLLGVGSAIAS 150
RSV F Pringle     101 PATNNRARRELPRFMNYTLNNTKNTNVTLSKKRKRRFLGFLLGVGSAIAS 150
RSV F 9320        101 PAANNRARREAPQYMNYTINTTKNLNVSISKKRKRRFLGFLLGVGSAIAS 150
synthetic const   101 PAANNRARRELPRFMNYTLNNTKKTNVTLSKKRKRRFLGFLLGVGSAIAS 150
synthetic CAA01   101 PAANNRARRELPRFMNYTLNNTKKTNVTLSKKRKRRFLGFLLGVGSAIAS 150
                      * .******* *..****.*..*  **..*********************
```

Figure 1 (A)

```
 Novavax F        151 GVAVSKVLHLEGEVNKIKSALLSTNKAVVSLSNGVSVLTSKVLDLKNYID 200
RSV F S2          151 GIAVSKVLHLEGEVNKIKSALLSTNKAVVSLSNGVSVLTSKVLDLKNYID 200
RSV F B unident   151 GIAVSKVLHLEGEVNKIKNALLSTNKAVVSLSNGVSVLTSKVLDLKNYIN 200
RSV FB            151 GIAVSKVLHLEGEVNKIKNALLSTNKAVVSLSNGVSVLTSKVLDLKSYIN 200
RSV F NP56863     151 GIAVSKVLHLEGEVNKIKNALLSTNKAVVSLSNGVSVLTSKVLDLKNYIN 200
RSV F B1 cp       151 GIAVSKVLHLEGEVNKIKNALLSTNKAVVSLSNGVSVLTSKVLDLKNYIN 200
RSV F B1          151 GIAVSKVLHLEGEVNKIKNALLSTNKAVVSLSNGVSVLTSKVLDLKNYIN 200
RSV F A2cp        151 GVAVSKVLHLEGEVNKIKSALLSTNKAVVSLSNGVSVLTSKVLDLKNYID 200
RSV F A2          151 GVAVSKVLHLEGEVNKIKSALLSTNKAVVSLSNGVSVLTSKVLDLKNYID 200
RSV F Pringle     151 GIAVSKVLHLEGEVNKIKSALLSTNKAVVSLSNGVSVLTSKVLDLKNYID 200
RSV F 9320        151 GIAVSKVLHLEGEVNKIKNALLSTNKAVVSLSNGVSVLTSKVLDLKSYIN 200
synthetic const   151 GIAVSKVLHLEGEVNKIKSALLSTNKAVVSLSNGVSVLTSKVLDLKNYID 200
synthetic CAA01   151 GIAVSKVLHLEGEVNKIKSALLSTNKAVVSLSNGVSVLTSKVLDLKNYID 200
                      *.**************** *************************** **

Novavax F         201 KQLLPIVNKQSCSISNIETVIEFQQKNNRLLEITREFSVNAGVTTPVSTY 250
RSV F S2          201 KQLLPIVNKQSCSISNIETVIEFQQKNNRLLEITREFSVNAGVTTPVSTY 250
RSV F B unident   201 NRLLPIVNQQSCRISNIETVIEFQQMNSRLLEITREFSVNAGVTTPLSTY 250
RSV FB            201 NQLLPIVNQQSCRISNIETVIEFQQKNSRLLEITREFSVNAGVTTPLSTY 250
RSV F NP56863     201 NQLLPIVNQQSCRISNIETVIEFQQKNSRLLEINREFSVNAGVTTPLSTY 250
RSV F B1 cp       201 NQLLPIVNQQSCRISNIGTVIEFQQKNSRLLEINREFSVNAGVTTPLSTY 250
RSV F B1          201 NQLLPIVNQQSCRISNIETVIEFQQKNSRLLEINREFSVNAGVTTPLSTY 250
RSV F A2cp        201 KQLLPIVNKQSCSISNIATVIEFQQKNNRLLEITREFSVNAGVTTPVSTY 250
RSV F A2          201 KQLLPIVNKQSCSISNIATVIEFQQKNNRLLEITREFSVNAGVTTPVSTY 250
RSV F Pringle     201 KQLLPIVNKQSCSISNIETVIEFQQKNNRLLEITREFSVNAGVTTPVSTY 250
RSV F 9320        201 NQLLPIVNQQSCRISNIETVIEFQQKNSRLLEITREFSVNAGVTTPLSTY 250
synthetic const   201 KQLLPIVNKQSCRISNIETVIEFQQKNNRLLEITREFSVNVGVTTPVSTY 250
synthetic CAA01   201 KQLLPIVNKRSCRISNIETVIEFQHKNNRLLEITREFSVNAGVTTPVSTY 250
                      .******..** **** ******.  * *****.****** *****.**

Novavax F         251 MLTNSELLSLINDMPITNDQKKLMSNNVQIVRQQSYSIMSIIKEEVLAYV 300
RSV F S2          251 MLTNSELLSLINDMPITNDQKKLMSNNVQIVRQQSYSIMSIIKEEVLAYV 300
RSV F B unident   251 MLTNSELLSLINDMPITNDQKKLMSSNVQIVRQQSYSIMSIIKEEVLAYV 300
RSV FB            251 MLTNSELLSLINDMPITNDQKKLMSSNVQIVRQQSYSIMSIIKEEVLAYV 300
RSV F NP56863     251 MLTNSELLSLINDMPITNDQKKLMSSNVQIVRQQSYSIMSIIKEEVLAYV 300
RSV F B1 cp       251 MLTNSELLSLINDMPITNDQKKLMSSNVQIVRQQSYSIMSIIKEEVLAYV 300
RSV F B1          251 MLTNSELLSLINDMPITNDQKKLMSSNVQIVRQQSYSIMSIIKEEVLAYV 300
RSV F A2cp        251 MLTNSELLSLINDMPITNDQKKLMSNNVQIVRQQSYSIMSIIKEEVLAYV 300
RSV F A2          251 MLTNSELLSLINDMPITNDQKKLMSNNVQIVRQQSYSIMSIIKEEVLAYV 300
RSV F Pringle     251 MLTNSELLSLINDMPITNDQKKLMSNNVQIVRQQSYSIMSIIKEEVLAYV 300
RSV F 9320        251 MLTNSELLSLINDMPITNDQKKLMSSNVQIVRQQSYSIMSIIKEEVLAYV 300
synthetic const   251 MLTNSELLSLINDMPITNDQKKLMSNNVQIVRQQSYSIMSIIKEEVLAYV 300
synthetic CAA01   251 MLTNSELLSLINDMPITNDQKKLMSNNVQIVRQQSYSIMSIIKEEVLAYV 300
                      ************************ *************************
```

Figure 1 (B)

```
Novavax F           301 VQLPLYGVIDTPCWKLHTSPLCTTNTKEGSNICLTRTDRGWYCDNAGSVS 350
RSV F S2            301 VQLPLYGVIDTPCWKLHTSPLCTTNTKEGSNICLTRTDRGWYCDNAGSVS 350
RSV F B unident     301 VQLPIYGVIDTPCWKLHTSPLCTTNIKEGSNICLTRTDRGWYCDNAGSVS 350
RSV FB              301 VQLPIYGVIDTPCWKLHTSPLCTTNIKEGSNICLTRTDRGWYCDNAGSVS 350
RSV F NP56863       301 VQLPIYGVIDTPCWKLHTSPLCTTNIKEGSNICLTRTDRGWYCDNAGSVS 350
RSV F B1 cp         301 VQLPIYGVIDTPCWKLHTSPLCTTNIKEGSNICLTRTDRGWYCDNAGSVS 350
RSV F B1            301 VQLPIYGVIDTPCWKLHTSPLCTTNIKEGSNICLTRTDRGWYCDNAGSVS 350
RSV F A2cp          301 VQLPLYGVIDTPCWKLHTSPLCTTNTKEGSNICLTRTDRGWYCDNAGSVS 350
RSV F A2            301 VQLPLYGVIDTPCWKLHTSPLCTTNTKEGSNICLTRTDRGWYCDNAGSVS 350
RSV F Pringle       301 VQLPLYGVIDTPCWKLHTSPLCTTNTKEGSNICLTRTDRGWYCDNAGSVS 350
RSV F 9320          301 VQLPIYGVIDTPCWKLHTSPLCTTNIKEGSNICLTRTDRGWYCDNAGSVS 350
synthetic const     301 VQLPLYGVIDTPCWKLHTSPLCTTNTKEGSNICLTRTDRGWYCDNAGSVS 350
synthetic CAA01     301 VQLPLYGVIDTPCWKLHTSPLCTTNTKEGSNICLTRTDRGWYCDNAGSVS 350
                        ****.******************** ************************

Novavax F           351 FFPQAETCKVQSNRVFCDTMNSLTLPSEINLCNVDIFNPKYDCKIMTSKT 400
RSV F S2            351 FFPLAETCKVQSNRVFCDTMNSLTLPSEVNLCNIDIFNPKYDCKIMTSKT 400
RSV F B unident     351 FFPQADTCKVQSNRVFCDTMNSLTLPSEVSLCNTDIFNSKYDCKIMTSKT 400
RSV FB              351 FFPQADTCKVQSNRVFCDTMNSLTLPSEVSLCNTDIFNSKYDCKIMTSKT 400
RSV F NP56863       351 FFPQADTCKVQSNRVFCDTMNSLTLPSEVSLCNTDIFNSKYDCKIMTSKT 400
RSV F B1 cp         351 FFPQADTCKVQSNRVFCDTMNSLTLPSEVSLCNTDIFNSKYDCKIMTSKT 400
RSV F B1            351 FFPQADTCKVQSNRVFCDTMNSLTLPSEVSLCNTDIFNSKYDCKIMTSKT 400
RSV F A2cp          351 FFPQAETCKVQSNRVFCDTMNSLTLPSEVNLCNVDIFNPKYDCKIMTSKT 400
RSV F A2            351 FFPQAETCKVQSNRVFCDTMNSLTLPSEVNLCNVDIFNPKYDCKIMTSKT 400
RSV F Pringle       351 FFPLAETCKVQSNRVFCDTMNSLTLPSEVNLCNIDIFNPKYDCKIMTSKT 400
RSV F 9320          351 FFPQADTCKVQSNRVFCDTMNSLTLPSEVSLCNTDIFNSKYDCKIMTSKT 400
synthetic const     351 FFPQAETCKVQSNRVFCDTMNSLTLPSEVNLCNVDIFNPKYDCKIMTSKT 400
synthetic CAA01     351 FFPQAETCKVQSNRVFCDTMNSLTLPSEVNLCNVDIFNPKYDCKIMTSKT 400
                        *** *.**********************. *** **** ***********

Novavax F           401 DVSSSVITSLGAIVSCYGKTKCTASNKNRGIIKTFSNGCDYVSNKGMDTV 450
RSV F S2            401 DVSSSVITSLGAIVSCYGKTKCTASNKNRGIIKTFSNGCDYVSNKGVDTV 450
RSV F B unident     401 DISSSVITSLGAIVSCYGKTKCTASNKNRGIIKTFSNGCDYVSNKGVDTV 450
RSV FB              401 DISSSVITSLGAIVSCYGKTKCTASNKNRGIIKTFSNGCDYVSNKGVDTV 450
RSV F NP56863       401 DISSSVITSLGAIVSCYGKTKCTASNKNRGIIKTFSNGCDYVSNKGVDTV 450
RSV F B1 cp         401 DISSSVITSLGAIVSCYGKTKCTASNKNRGIIKTFSNGCDYVSNKGVDTV 450
RSV F B1            401 DISSSVITSLGAIVSCYGKTKCTASNKNRGIIKTFSNGCDYVSNKGVDTV 450
RSV F A2cp          401 DVSSSVITSLGAIVSCYGKTKCTASNKNRGIIKTFSNGCDYVSNKGVDTV 450
RSV F A2            401 DVSSSVITSLGAIVSCYGKTKCTASNKNRGIIKTFSNGCDYVSNKGVDTV 450
RSV F Pringle       401 DVSSSVITSLGAIVSCYGKTKCTASNKDRGIIKTFSNGCDYVSNKGVDTV 450
RSV F 9320          401 DISSSVITSLGAIVSCYGKTKCTASNKNRGIIKTFSNGCDYVSNKGVDTV 450
synthetic const     401 DVSSSVITSLGAIVSCYGKTKCTASNKNRGIIKTFSNGCDYVSNKGVDTV 450
synthetic CAA01     401 DVSSSVITSLGAIVSCYGKTKCTASNKNRGIIKTFSNGCDYVSNKGVDTV 450
                        *.************************* ******************.***
```

Figure 1 (C)

```
Novavax F           451 SVGNTLYYVNKQEGKSLYVKGEPIINFYDPLVFPSDEFDASISQVNEKIN 500
RSV F S2            451 SVGNTLYYVNKQEGKSLYVKGEPIINFYDPLVFPSDEFDASISQVNEKIN 500
RSV F B unident     451 SVGNTLYYVNKLEGKNLYVKGEPIINYYDPLVFPSDEFDASISQVNEKIN 500
RSV FB              451 SVGNTLYYVNKLEGKNLYVKGEPIINYYDPLVFPSDEFDASISQVNEKIN 500
RSV F NP56863       451 SVGNTLYYVNKLEGKNLYVKGEPIINYYDPLVFPSDEFDASISQVNEKIN 500
RSV F B1 cp         451 SVGNTLYYVNKLEGKNLYVKGEPIINYYDPLVFPSDEFDASISQVNEKIN 500
RSV F B1            451 SVGNTLYYVNKLEGKNLYVKGEPIINYYDPLVFPSDEFDASISQVNEKIN 500
RSV F A2cp          451 SVGNTLYYVNKQEGKSLYVKGEPIINFYDPLVFPSDEFDASISQVNEKIN 500
RSV F A2            451 SVGNTLYYVNKQEGKSLYVKGEPIINFYDPLVFPSDEFDASISQVNEKIN 500
RSV F Pringle       451 SVGNTLYYVNKQEGKSLYVKGEPIINFYDPLVFPSDEFDASISQVNEKIN 500
RSV F 9320          451 SVGNTLYYVNKLEGKNLYVKGEPIINYYDPLVFPSDEFDASISQVNEKIN 500
synthetic const     451 SVGNTLYYVNKQEGKSLYVKGEPIINFYDPLVFPSDEFDASISQVNEKIN 500
synthetic CAA01     451 SVGNTLYYVNKQEGKSLYVKGEPIINFYDPLVFPSDEFDASISQVNEKIN 500
                        *********** *** **********.***********************

Novavax F           501 QSLAFIRKSDELLHNVNAGKSTTNIMITTIIIVIIVILLSLIAVGLLLYC 550
RSV F S2            501 QSLAFIRKSDELLHNVNAGKSTTNIMITTIIIVIIVILLSLIAVGLLLYC 550
RSV F B unident     501 QSLAFIRRSDELLHNVNTGKSTTNIMITTIIIVIIVVLLSLIAIGLLLYC 550
RSV FB              501 QSLAFIRRSDELLHNVNTGKSTTNIMITTIIIVIIVVLLSLIAIGLLLYC 550
RSV F NP56863       501 QSLAFIRRSDELLHNVNTGKSTTNIMITTIIIVIIVVLLSLIAIGLLLYC 550
RSV F B1 cp         501 QSLAFIRRSDELLHNVNTGKSTTNIMITTIIIVIIVVLLSLIAIGLLLYC 550
RSV F B1            501 QSLAFIRRSDELLHNVNTGKSTTNIMITTIIIVIIVVLLSLIAIGLLLYC 550
RSV F A2cp          501 QSLAFIRKSDELLHNVNAGKSTINIMITTIIIVIIVILLSLIAVGLLLYC 550
RSV F A2            501 QSLAFIRKSDELLHNVNAGKSTINIMITTIIIVIIVILLSLIAVGLLLYC 550
RSV F Pringle       501 QSLAFIRKSDELLHNVNAGKSTTNIMITTIIIVIIVILLSLIAVGLLLYC 550
RSV F 9320          501 QSLAFIRRSDELLHNVNTGKSTTNIMITTIIIVIIVVLLSLIAIGLLLYC 550
synthetic const     501 QSLAFIRKSDELLHNVNAGKSTTNIMITTIIIVIIVILLSLIAVGLLLYC 550
synthetic CAA01     501 QSLAFIRKSDELLHNVNAGKSTTNIMITTIIIEIIVILLSLIAVGLLLYC 550
                        *******.*********.**** ********* ***.******.******

Novavax F           551 KARSTPVTLSKDQLSGINNIAFSN 574
RSV F S2            551 KARSTPVTLSKDQLSGINNIAFSN 574
RSV F B unident     551 KAKNTPVTLSKDQLSGINNIAFSK 574
RSV FB              551 KAKNTPVTLSKDQLSGINNIAFSK 574
RSV F NP56863       551 KAKNTPVTLSKDQLSGINNIAFSK 574
RSV F B1 cp         551 KAKNTPVTLSKDQLSGINNIAFSK 574
RSV F B1            551 KAKNTPVTLSKDQLSGINNIAFSK 574
RSV F A2cp          551 KARSTPVTLSKDQLSGINNIAFSN 574
RSV F A2            551 KARSTPVTLSKDQLSGINNIAFSN 574
RSV F Pringle       551 KARSTPVTLSKDQLSGINNIAFSN 574
RSV F 9320          551 KAKNTPVTLSKDQLSGINNIAFSK 574
synthetic const     551 KARSTPVTLSKDQLSGINNIAFSN 574
synthetic CAA01     551 KARSTPVTLSKDQLSGINNIAFSN 574
                        **. *******************
```

Figure 1 (D)

MELLILKANAITTILTAVTFCFASGQNITEEFYQSTCSAVSKGYLSALRTGWYTSVITIELSNIKKNKCN
GTDAKVKLIKQELDKYKNAVTELQLLMQSTQATNNRARRELPRFMNYTLNNAKKTNVTLSKKRKRRFLGF
LLGVGSAIASGVAVSKVLHLEGEVNKIKSALLSTNKAVVSLSNGVSVLTSKVLDLKNYIDKQVLPIVNKQ
SCSISNIETVIEFQQKNNRLLEITREFSVNAGVTTPVSTYMLTNSELLSLINDMPITNDQKKLMSNNVQI
VRQQSYSIMSIIKEEVLAYVVQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKTDVSSSVITSLGAIVSCYGKT
KCTASNKNRGIIKTFSNGCDYVSNKGVDTVSVGNTLYYVNKQEGKSLYVKGEPIINFYDPLVFPSDEFDA
SISQVNEKINQSLAFIRKSDELLHNVNAGKSTTNIMITTIIIVIIVILLSLIAVGLLLYCKARSTPVTLS
KDQLSGINNIAFSN

CTCGAGGGCAATATACAATGGAGTTGCTAATCCTCAAAGCAAATGCAATTACCACAATCCTCACTGCAGTC
ACATTTTGTTTTGCTTCTGGTCAAAACATCACTGAAGAATTTTATCAATCAACATGCAGTGCNGTTAGCAA
AGGCTATCTTAGTGCTCTGAGAACTGGTTGGTATACCAGTGTTATAACTATAGAATTAAGTAATATCAAGA
AAAATAAGTGTAATGGAACAGATGCTAAGGTAAAATTGATAAAACAAGAATTAGATAAATATAAAAATGCT
GTAACAGAATTGCAGTTGCTCATGCAAAGCACACAAGCAACAAACAATCGAGCCAGAAGAGAACTACCAAG
GTTTATGAATTATACACTCAACAATGCCAAAAAAACCAATGTAACATTAAGCAAGAAAAGGAAAAGAAGAT
TTCTTGGTTTTTGTTAGGTGTTGGATCTGCAATCGCCAGTGGCGTTGCTGTATCTAAGGTCCTGCACCTA
GAAGGGGAAGTGAACAAGATCAAAAGTGCTCTACTATCCACAAACAAGGCTGTAGTCAGCTTATCAAATGG
AGTTAGTGTCTTAACCAGCAAAGTGTTAGACCTCAAAAACTATATAGATAAACAAGTGTTACCTATTGTGA
ACAAGCAAAGCTGCAGCATATCAAATATAGAAACTGTGATAGAGTTCCAACAAAAGAACAACAGACTACTA
GAGATTACCAGGGAATTTAGTGTTAATGCAGGTGTAACTACACCTGTAAGCACTTACATGTTAACTAATAG
TGAATTATTGTCATTAATCAATGATATGCCTATAACAAATGATCAGAAAAAGTTAATGTCCAACAATGTTC
AAATAGTTAGACAGCAAAGTTACTCTATCATGTCCATAATAAAAGAGGAAGTCTTAGCATATGTAGTACAA
TTACCACTATATGGTGTTATAGATACACCCTGTTGGAAACTACACACATCCCCTCTATGTACAACCAACAC
AAAAGAAGGGTCCAACATCTGTTTAACAAGAACTGACAGAGGATGGTACTGTGACAATGCAGGATCAGTAT
CTTTCTTCCCACAAGCTGAAACATGTAAAGTTCAATCAAATCGAGTATTTTGTGACACAATGAACAGTTTA
ACATTACCAAGTGAAGTAAATCTCTGCAATGTTGACATATTCAACCCCAAATATGATTGTAAAATTATGAC
TTCAAAAACAGATGTAAGCAGCTCCGTTATCACATCTCTAGGAGCCATTGTGTCATGCTATGGCAAAACTA
AATGTACAGCATCCAATAAAAATCGTGGAATCATAAAGACATTTTCTAACGGGTGCGATTATGTATCAAAT
AAAGGGGTGGACACTGTGTCTGTAGGTAACACATTATATTATGTAAATAAGCAAGAAGGTAAAAGTCTCTA
TGTAAAAGGTGAACCAATAATAAATTTCTATGACCCATTAGTATTCCCCTCTGATGAATTTGATGCATCAA
TATCTCAAGTCAACGAGAAGATTAACCAGAGCCTAGCATTTATTCGTAAATCCGATGAATTATTACATAAT
GTAAATGCTGGTAAATCCACCACAAATATCATGATAACTACTATAATTATAGTGATTATAGTAATATTGTT
ATCATTAATTGCTGTTGGACTGCTCTTATACTGTAAGGCCAGAAGCACACCAGTCACACTAAGCAAAGATC
AACTGAGTGGTATAAATAATATTGCATTTAGTAACTAAATAAAAATAGCACCTAATCATGTTCTTACAATG
GTTTACTATCTGGCCA

5' untranslated region

CTCGAGGGCAATATACA

Nucleotide sequence of F-LM ectodomain

ATGGAGTTGCTAATCCTCAAAGCAAATGCAATTACCACAATCCTCACTGCAGTCACATTTTGTTTTGCTTC
TGGTCAAAACATCACTGAAGAATTTTATCAATCAACATGCAGTGCNGTTAGCAAAGGCTATCTTAGTGCTC
TGAGAACTGGTTGGTATACCAGTGTTATAACTATAGAATTAAGTAATATCAAGAAAAATAAGTGTAATGGA
ACAGATGCTAAGGTAAAATTGATAAAACAAGAATTAGATAAATATAAAAATGCTGTAACAGAATTGCAGTT
GCTCATGCAAAGCACACAAGCAACAAACAATCGAGCCAGAAGAGAACTACCAAGGTTTATGAATTATACAC
TCAACAATGCCAAAAAAACCAATGTAACATTAAGCAAGAAAAGGAAAAGAAGATTTCTTGGTTTTTTGTTA
GGTGTTGGATCTGCAATCGCCAGTGGCGTTGCTGTATCTAAGGTCCTGCACCTAGAAGGGGAAGTGAACAA
GATCAAAAGTGCTCTACTATCCACAAACAAGGCTGTAGTCAGCTTATCAAATGGAGTTAGTGTCTTAACCA
GCAAAGTGTTAGACCTCAAAAACTATATAGATAAACAAGTGTTACCTATTGTGAACAAGCAAAGCTGCAGC
ATATCAAATATAGAAACTGTGATAGAGTTCCAACAAAAGAACAACAGACTACTAGAGATTACCAGGGAATT
TAGTGTTAATGCAGGTGTAACTACACCTGTAAGCACTTACATGTTAACTAATAGTGAATTATTGTCATTAA
TCAATGATATGCCTATAACAAATGATCAGAAAAAGTTAATGTCCAACAATGTTCAAATAGTTAGACAGCAA
AGTTACTCTATCATGTCCATAATAAAAGAGGAAGTCTTAGCATATGTAGTACAATTACCACTATATGGTGT
TATAGATACACCCTGTTGGAAACTACACACATCCCCTCTATGTACAACCAACACAAAAGAAGGGTCCAACA
TCTGTTTAACAAGAACTGACAGAGGATGGTACTGTGACAATGCAGGATCAGTATCTTTCTTCCCACAAGCT
GAAACATGTAAAGTTCAATCAAATCGAGTATTTTGTGACACAATGAACAGTTTAACATTACCAAGTGAAGT
AAATCTCTGCAATGTTGACATATTCAACCCCAAATATGATTGTAAAATTATGACTTCAAAAACAGATGTAA
GCAGCTCCGTTATCACATCTCTAGGAGCCATTGTGTCATGCTATGGCAAAACTAAATGTACAGCATCCAAT
AAAAATCGTGGAATCATAAAGACATTTTCTAACGGGTGCGATTATGTATCAAATAAAGGGGTGGACACTGT
GTCTGTAGGTAACACATTATATTATGTAAATAAGCAAGAAGGTAAAAGTCTCTATGTAAAAGGTGAACCAA
TAATAAATTTCTATGACCCATTAGTATTCCCCTCTGATGAATTTGATGCATCAATATCTCAAGTCAACGAG
AAGATTAACCAGAGCCTAGCATTTATTCGTAAATCCGATGAATTATTACATAATGTAAATGCTGGTAAATC
CACCACAAAT

Nucleotide sequence of F-LM TM domain

ATCATGATAACTACTATAATTATAGTGATTATAGTAATATTGTTATCATTAATTGCTGTTGGACTGCTCTT
ATACTG

Nucleotide sequence of F-LM CT domain

TAAGGCCAGAAGCACACCAGTCACACTAAGCAAAGATCAACTGAGTGGTATAAATAATATTGCATTTAGTA
AC

3' untranslated region

TAAATAAAAATAGCACCTAATCATGTTCTTACAATGGTTTACTATCTGGCCA

Figure 3

(A) Ectodomain

MELLILKANAITTILTAVTFCFASGQNITEEFYQSTCSAVSKGYLSALRTGWYTSVITIELSNIKKN
KCNGTDAKVKLIKQELDKYKNAVTELQLLMQSTQATNNRARRELPRFMNYTLNNAKKTNVTLS
KKRKRRFLGFLLGVGSAIASGVAVSKVLHLEGEVNKIKSALLSTNKAVVSLSNGVSVLTSKVLDL
KNYIDKQVLPIVNKQSCSISNIETVIEFQQKNNRLLEITREFSVNAGVTTPVSTYMLTNSELLSLIN
DMPITNDQKKLMSNNVQIVRQQSYSIMSIIKEEVLAYVVQLPLYGVIDTPCWKLHTSPLCTTNTK
EGSNICLTRTDRGWYCDNAGSVSFFPQAETCKVQSNRVFCDTMNSLTLPSEVNLCNVDIFNPK
YDCKIMTSKTDVSSSVITSLGAIVSCYGKTKCTASNKNRGIIKTFSNGCDYVSNKGVDTVSVGNT
LYYVNKQEGKSLYVKGEPIINFYDPLVFPSDEFDASISQVNEKINQSLAFIRKSDELLHNVNAGKS
TTN

(B) TM domain

IMITTIIIVIIVILLSLIAVGLLLYC

C) CT domain

KARSTPVTLSKDQLSGINNIAFSN

Figure 5

| | Ectodomains | TM | CT |
|---|---|---|---|
| NDV F | | | |
| RSV G | | | |
| F/F chimera1 | | | |

NDV F ---TSTSA    LITYIA---
RSV F ---KSTTN    VILWF------
F/F #1 ----KSTTN   LITYIA----

F/F chimera 2        HR2  TM  CT

NDV F    ---NLDISTE    LGNVNNS----
RSV F    -----IRKSDEL   LHNVNT----
F/F #2   -----IRKSDEL   LGNVNNS----

Figure 16: Nucleotide Sequence of F/F chimera 1

F/F CHIMERA #1 (also referred to as F/F chimera)

ATGGAGTTGCTAATCCTCAAAGCAAATGCAATTACCACAATCCTCACTGCAGTCACATTTTG
TTTTGCTTCTGGTCAAAACATCACTGAAGAATTTTATCAATCAACATGCAGTGCNGTTAGCA
AAGGCTATCTTAGTGCTCTGAGAACTGGTTGGTATACCAGTGTTATAACTATAGAATTAAGT
AATATCAAGAAAAATAAGTGTAATGGAACAGATGCTAAGGTAAAATTGATAAAACAAGAATT
AGATAAATATAAAAATGCTGTAACAGAATTGCAGTTGCTCATGCAAAGCACACAAGCAACAA
ACAATCGAGCCAGAAGAGAACTACCAAGGTTTATGAATTATACACTCAACAATGCCAAAAAA
ACCAATGTAACATTAAGCAAGAAAAGGAAAAGAAGATTTCTTGGTTTTTTGTTAGGTGTTGG
ATCTGCAATCGCCAGTGGCGTTGCTGTATCTAAGGTCCTGCACCTAGAAGGGGAAGTGAA
CAAGATCAAAAGTGCTCTACTATCCACAAACAAGGCTGTAGTCAGCTTATCAAATGGAGTTA
GTGTCTTAACCAGCAAAGTGTTAGACCTCAAAAACTATATAGATAAACAAGTGTTACCTATT
GTGAACAAGCAAAGCTGCAGCATATCAAATATAGAAACTGTGATAGAGTTCCAACAAAAGA
ACAACAGACTACTAGAGATTACCAGGGAATTTAGTGTTAATGCAGGTGTAACTACACCTGTA
AGCACTTACATGTTAACTAATAGTGAATTATTGTCATTAATCAATGATATGCCTATAACAAAT
GATCAGAAAAAGTTAATGTCCAACAATGTTCAAATAGTTAGACAGCAAAGTTACTCTATCAT
GTCCATAATAAAAGAGGAAGTCTTAGCATATGTAGTACAATTACCACTATATGGTGTTATAG
ATACACCCTGTTGGAAACTACACACATCCCCTCTATGTACAACCAACACAAAAGAAGGGTC
CAACATCTGTTTAACAAGAACTGACAGAGGATGGTACTGTGACAATGCAGGATCAGTATCT
TTCTTCCCACAAGCTGAAACATGTAAAGTTCAATCAAATCGAGTATTTTGTGACACAATGAA
CAGTTTAACATTACCAAGTGAAGTAAATCTCTGCAATGTTGACATATTCAACCCCAAATATG
ATTGTAAAATTATGACTTCAAAAACAGATGTAAGCAGCTCCGTTATCACATCTCTAGGAGCC
ATTGTGTCATGCTATGGCAAAACTAAATGTACAGCATCCAATAAAAATCGTGGAATCATAAA
GACATTTTCTAACGGGTGCGATTATGTATCAAATAAAGGGGTGGACACTGTGTCTGTAGGT
AACACATTATATTATGTAAATAAGCAAGAAGGTAAAAGTCTCTATGTAAAAGGTGAACCAAT
AATAAATTTCTATGACCCATTAGTATTCCCCTCTGATGAATTTGATGCATCAATATCTCAAGT
CAACGAGAAGATTAACCAGAGCCTAGCATTTATTCGTAAATCCGATGAATTATTACATAATG
TAAACGCCGGGAAGAGTACTACTAATCTCATTACCTATATCGCTTTAACTGCCATATCTCTT
GTTTGCGGTATACTTAGTCTGGTTCTAGCATGCTACCTAATGTACAAGCAAAAGGCGCAAC
AAAAGACCTTGTTATGGCTTGGGAATAATACCCTGGGTCAGATGAGAGCCACTACAAAAAT
GTGA

RSV F sequence from base 1 to 1572
NDV F sequence from base 1573 to 1731

Figure 17: Nucleotide Sequence of F/HR2F

F/HR2F chimera (also referred to as F/F chimera #2)

ATGGAGTTGCTAATCCTCAAAGCAAATGCAATTACCACAATCCTCACTGCAGTCACATTTTG
TTTTGCTTCTGGTCAAAACATCACTGAAGAATTTTATCAATCAACATGCAGTGCNGTTAGCA
AAGGCTATCTTAGTGCTCTGAGAACTGGTTGGTATACCAGTGTTATAACTATAGAATTAAGT
AATATCAAGAAAAATAAGTGTAATGGAACAGATGCTAAGGTAAAATTGATAAAACAAGAATT
AGATAAATATAAAAATGCTGTAACAGAATTGCAGTTGCTCATGCAAAGCACACAAGCAACAA
ACAATCGAGCCAGAAGAGAACTACCAAGGTTTATGAATTATACACTCAACAATGCCAAAAAA
ACCAATGTAACATTAAGCAAGAAAAGGAAAAGAAGATTTCTTGGTTTTTTGTTAGGTGTTGG
ATCTGCAATCGCCAGTGGCGTTGCTGTATCTAAGGTCCTGCACCTAGAAGGGGAAGTGAA
CAAGATCAAAAGTGCTCTACTATCCACAAACAAGGCTGTAGTCAGCTTATCAAATGGAGTTA
GTGTCTTAACCAGCAAAGTGTTAGACCTCAAAAACTATATAGATAAACAAGTGTTACCTATT
GTGAACAAGCAAAGCTGCAGCATATCAAATATAGAAACTGTGATAGAGTTCCAACAAAAGA
ACAACAGACTACTAGAGATTACCAGGGAATTTAGTGTTAATGCAGGTGTAACTACACCTGTA
AGCACTTACATGTTAACTAATAGTGAATTATTGTCATTAATCAATGATATGCCTATAACAAAT
GATCAGAAAAAGTTAATGTCCAACAATGTTCAAATAGTTAGACAGCAAAGTTACTCTATCAT
GTCCATAATAAAAGAGGAAGTCTTAGCATATGTAGTACAATTACCACTATATGGTGTTATAG
ATACACCCTGTTGGAAACTACACACATCCCCTCTATGTACAACCAACACAAAAGAAGGGTC
CAACATCTGTTTAACAAGAACTGACAGAGGATGGTACTGTGACAATGCAGGATCAGTATCT
TTCTTCCCACAAGCTGAAACATGTAAAGTTCAATCAAATCGAGTATTTTGTGACACAATGAA
CAGTTTAACATTACCAAGTGAAGTAAATCTCTGCAATGTTGACATATTCAACCCCAAATATG
ATTGTAAAATTATGACTTCAAAAACAGATGTAAGCAGCTCCGTTATCACATCTCTAGGAGCC
ATTGTGTCATGCTATGGCAAAACTAAATGTACAGCATCCAATAAAAATCGTGGAATCATAAA
GACATTTTCTAACGGGTGCGATTATGTATCAAATAAAGGGGTGGACACTGTGTCTGTAGGT
AACACATTATATTATGTAAATAAGCAAGAAGGTAAAAGTCTCTATGTAAAAGGTGAACCAAT
AATAAATTTCTATGACCCATTAGTATTCCCCTCTGATGAATTTGATGCATCAATATCTCAAGT
CAACGAGAAGATTAACCAGAGCCTAGCATTTATTCGTAAATCCGATGAATTACTTGGGAAC
GTCAACAACTCGATAAGTAATGCTTTGGATAAGTTAGAGGAAAGCAACAGCAAACTAGACA
AAGTCAATGTCAAACTGACCAGCACATCTGCTCTCATTACCTATATCGCTTTAACTGCCATA
TCTCTTGTTTGCGGTATACTTAGTCTGGTTCTAGCATGCTACCTAATGTACAAGCAAAAGGC
GCAACAAAAGACCTTGTTATGGCTTGGGAATAATACCCTGGGTCAGATGAGAGCCACTACA
AAAATGTGA

Underlined sequence is the NDV HR2 domain.
RSV sequence is from base 1 to 1536.
NDV sequence is from base 1537 to 1797

Figure 18 (A): Amino acid sequences of the RSV F/NDV F chimera protein

F/F chimera 1 amino acid sequence

MELLILKANAITTILTAVTFCFASGQNITEEFYQSTCSAVSKGYLSALRTGWYTSVITIELS
NIKKNKCNGTDAKVKLIKQELDKYKNAVTELQLLMQSTQATNNRARRELPRFMNYTLNNAKKT
NVTLSKKRKRRFLGFLLGVGSAIASGVAVSKVLHLEGEVNKIKSALLSTNKAVVSLSNGVSVLTS
KVLDLKNYIDKQVLPIVNKQSCSISNIETVIEFQQKNNRLLEITREFSVNAGVTTPVSTYMLTNSEL
LSLINDMPITNDQKKLMSNNVQIVRQQSYSIMSIIKEEVLAYVVQLPLYGVIDTPCWKLHTSPLCT
TNTKEGSNICLTRTDRGWYCDNAGSVSFFPQAETCKVQSNRVFCDTMNSLTLPSEVNLCNVDI
FNPKYDCKIMTSKTDVSSSVITSLGAIVSCYGKTKCTASNKNRGIIKTFSNGCDYVSNKGVDTVS
VGNTLYYVNKQEGKSLYVKGEPIINFYDPLVFPSDEFDASISQVNEKINQSLAFIRKSDELLHNVN
AGKSTTNLITYIALTAISLVCGILSLVLACYLMYKQKAQQKTLLWLGNNTLGQMRATTKM*

RSV sequence from amino acid 1-525
NDV sequence from amino acid 526-578

Figure 18 (B): Amino acid sequences of the F/HR2F chimera protein

F/HR2F (F/F chimera 2) amino acid sequence

MELLILKANAITTILTAVTFCFASGQNITEEFYQSTCSAVSKGYLSALRTGWYTSVITIELS
NIKKNKCNGTDAKVKLIKQELDKYKNAVTELQLLMQSTQATNNRARRELPRFMNYTLNNAKKT
NVTLSKKRKRRFLGFLLGVGSAIASGVAVSKVLHLEGEVNKIKSALLSTNKAVVSLSNGVSVLTS
KVLDLKNYIDKQVLPIVNKQSCSISNIETVIEFQQKNNRLLEITREFSVNAGVTTPVSTYMLTNSEL
LSLINDMPITNDQKKLMSNNVQIVRQQSYSIMSIIKEEVLAYVVQLPLYGVIDTPCWKLHTSPLCT
TNTKEGSNICLTRTDRGWYCDNAGSVSFFPQAETCKVQSNRVFCDTMNSLTLPSEVNLCNVDI
FNPKYDCKIMTSKTDVSSSVITSLGAIVSCYGKTKCTASNKNRGIIKTFSNGCDYVSNKGVDTVS
VGNTLYYVNKQEGKSLYVKGEPIINFYDPLVFPSDEFDASISQVNEKINQSLAFIRKSDELLGNV
NNSISNALDKLEESNSKLDKVNVKLTSTSALITYIALTAISLVCGILSLVLACYLMYKQKAQQKTLL
WLGNNTLGQMRATTKM*

F/F chimera 2: underlined sequence is the NDV HR2 domain

RSV sequence from amino acid 1-513
NDV sequence from amino acid 514-600

| | V | F/F #1 | F/F #2 | F/F #1 | F/F #2 | M |
|---|---|---|---|---|---|---|
| WB: RSV F | | | | | | |
| RSV G | | | | | | |
| | 1 | 2 | 3 | 4 | 5 | 6 | 7 |

VLPs with RSV F ectodomain

+NP+M+H/Ga    +NP+M

Figure 20 (A): nucleic acid sequence of H/G

ATGAACCGCGCAGTTTGCCAAGTTGCGCTAGAGAATGATGAAAGGGAAGCGAAGAATACA
TGGCGCTTGGTATTCCGGATCGCAATCTTACTTTTAACAGTAATGACCTTAGCCATCTCTGC
GGCCGCCCTGGCATATAGTGCGAATCATAAGGTCACACCCACGACCGCAATCATTCAGGA
CGCTACTAGCCAAATCAAAAACACAACCCCTACGTATTTGACTCAGAACCCACAACTGGGT
ATTTCACCGTCGAATCCCAGTGAAATCACCTCCCAGATCACAACTATTCTTGCCTCTACCAC
GCCTGGCGTTAAGAGCACACTCCAATCAACTACCGTAAAGACGAAAAACACAACTACCACC
CAGACGCAGCCATCCAAGCCGACAACTAAACAAAGGCAGAACAAGCCCCCTTCGAAGCCA
AATAACGATTTCCACTTCGAGGTGTTTAACTTCGTCCCGTGTAGTATCTGCTCTAATAACCC
CACCTGTTGGGCTATTTGCAAAAGAATCCCTAACAAGAAGCCAGGAAAAAAGACGACAACT
AAACCCACCAAGAAGCCTACGTTGAAAACAACTAAGAAGGACCCGAAACCACAAACCACGA
AGAGCAAAGAAGTTCCCACAACTAAGCCTACCGAGGAACCGACGATCAATACAACTAAGAC
CAACATTATCACGACACTGCTCACTTCAAATACCACTGGTAACCCAGAGCTGACCTCCCAG
ATGGAAACCTTCCATTCGACGAGTTCTGAGGGCAACCCCAGCCCTTCCCAAGTATCAACAA
CTTCGGAATACCCATCTCAGCCCAGTAGCCCTCCGAATACCCCACGACAATAA

NDV HN sequences from base 1-141
RSV G sequences from base 142-845

Figure 20 (B) : Amino acid sequence of H/G

MNRAVCQVALENDEREAKNTWRLVFRIAILLLTVMTLAISAAALAYSANHK
VTPTTAIIQDATSQIKNTTPTYLTQNPQLGISPSNPSEITSQITTILASTTPGV
KSTLQSTTVKTKNTTTTQTQPSKPTTKQRQNKPPSKPNNDFHFEVFNFVP
CSICSNNPTCWAICKRIPNKKPGKKTTTKPTKKPTLKTTKKDPKPQTTKSK
EVPTTKPTEEPTINTTKTNIITTLLTSNTTGNPELTSQMETFHSTSSEGNPS
PSQVSTTSEYPSQPSSPPNTPRQ*

NDV HN sequence from amino acid 1-48
RSV G sequence from amino acid 49-282

SEQUENCE LISTING

```
<160> NUMBER OF SEQ ID NOS: 29

<210> SEQ ID NO 1
<211> LENGTH: 574
<212> TYPE: PRT
<213> ORGANISM: Artificial Sequence
<220> FEATURE:
<223> OTHER INFORMATION: Synthetic

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

```
Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 2
<211> LENGTH: 574
<212> TYPE: PRT
<213> ORGANISM: Artificial Sequence
<220> FEATURE:
<223> OTHER INFORMATION: Synthetic

<400> SEQUENCE: 2

Met Glu Leu Pro Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

-continued

```
Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Leu Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495
```

-continued

```
Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 3
<211> LENGTH: 574
<212> TYPE: PRT
<213> ORGANISM: Artificial Sequence
<220> FEATURE:
<223> OTHER INFORMATION: Synthetic

<400> SEQUENCE: 3

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Arg Leu Leu Pro Ile Val Asn
        195                 200                 205

Gln Gln Ser Cys Arg Ile Ser Asn Ile Glu Thr Val Ile Glu Phe Gln
    210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285
```

Met Ser Ile Ile Lys Glu Glu Val Leu Ala Tyr Val Val Gln Leu Pro
290 295 300

Ile Tyr Gly Val Ile Asp Thr Pro Cys Trp Lys Leu His Thr Ser Pro
305 310 315 320

Leu Cys Thr Thr Asn Ile Lys Glu Gly Ser Asn Ile Cys Leu Thr Arg
325 330 335

Thr Asp Arg Gly Trp Tyr Cys Asp Asn Ala Gly Ser Val Ser Phe Phe
340 345 350

Pro Gln Ala Asp Thr Cys Lys Val Gln Ser Asn Arg Val Phe Cys Asp
355 360 365

Thr Met Asn Ser Leu Thr Leu Pro Ser Glu Val Ser Leu Cys Asn Thr
370 375 380

Asp Ile Phe Asn Ser Lys Tyr Asp Cys Lys Ile Met Thr Ser Lys Thr
385 390 395 400

Asp Ile Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Leu Glu Gly
450 455 460

Lys Asn Leu Tyr Val Lys Gly Glu Pro Ile Ile Asn Tyr Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Arg Ser Asp Glu Leu
500 505 510

Leu His Asn Val Asn Thr Gly Lys Ser Thr Thr Asn Ile Met Ile Thr
515 520 525

Thr Ile Ile Ile Val Ile Ile Val Val Leu Leu Ser Leu Ile Ala Ile
530 535 540

Gly Leu Leu Leu Tyr Cys Lys Ala Lys Asn Thr Pro Val Thr Leu Ser
545 550 555 560

Lys Asp Gln Leu Ser Gly Ile Asn Asn Ile Ala Phe Ser Lys
565 570

<210> SEQ ID NO 4
<211> LENGTH: 574
<212> TYPE: PRT
<213> ORGANISM: Artificial Sequence
<220> FEATURE:
<223> OTHER INFORMATION: Synthetic

<400> SEQUENCE: 4

Met Glu Leu Leu Ile His Arg Ser Ser Ala Ile Phe Leu Thr Leu Ala
1 5 10 15

Ile Asn Ala Leu Tyr Leu Thr Ser Ser Gln Asn Ile Thr Glu Glu Phe
20 25 30

Tyr Gln Ser Thr Cys Ser Ala Val Ser Arg Gly Tyr Phe Ser Ala Leu
35 40 45

Arg Thr Gly Trp Tyr Thr Ser Val Ile Thr Ile Glu Leu Ser Asn Ile
50 55 60

Lys Glu Thr Lys Cys Asn Gly Thr Asp Thr Lys Val Lys Leu Ile Lys
65 70 75 80

Gln Glu Leu Asp Lys Tyr Lys Asn Ala Val Thr Glu Leu Gln Leu Leu

-continued

```
                85                  90                  95

Thr Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Ser Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510
```

```
Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 5
<211> LENGTH: 574
<212> TYPE: PRT
<213> ORGANISM: Artificial Sequence
<220> FEATURE:
<223> OTHER INFORMATION: Synthetic

<400> SEQUENCE: 5

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
```

```
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 6
<211> LENGTH: 574
<212> TYPE: PRT
<213> ORGANISM: Artificial Sequence
<220> FEATURE:
<223> OTHER INFORMATION: Synthetic

<400> SEQUENCE: 6

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110
```

```
Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Gly Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
```

```
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 7
<211> LENGTH: 574
<212> TYPE: PRT
<213> ORGANISM: Artificial Sequence
<220> FEATURE:
<223> OTHER INFORMATION: Synthetic

<400> SEQUENCE: 7

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 8
<211> LENGTH: 574
<212> TYPE: PRT
<213> ORGANISM: Artificial Sequence
<220> FEATURE:
<223> OTHER INFORMATION: Synthetic

<400> SEQUENCE: 8

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125
```

```
Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560
```

```
Lys Asp Gln Leu Ser Gly Ile Asn Asn Ile Ala Phe Ser Asn
                565                 570


<210> SEQ ID NO 9
<211> LENGTH: 574
<212> TYPE: PRT
<213> ORGANISM: Artificial Sequence
<220> FEATURE:
<223> OTHER INFORMATION: Synthetic

<400> SEQUENCE: 9

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

```
Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 10
<211> LENGTH: 574
<212> TYPE: PRT
<213> ORGANISM: Artificial Sequence
<220> FEATURE:
<223> OTHER INFORMATION: Synthetic

<400> SEQUENCE: 10

Met Glu Leu Pro Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
```

-continued

```
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Leu Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asp Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 11
<211> LENGTH: 573
<212> TYPE: PRT
<213> ORGANISM: Artificial Sequence
<220> FEATURE:
<223> OTHER INFORMATION: Synthetic

<400> SEQUENCE: 11

Met Glu Leu Leu Ile His Arg Ser Ser Ala Ile Phe Leu Thr Leu Ala
1 5 10 15

Ile Asn Ala Leu Tyr Leu Thr Ser Ser Gln Asn Ile Thr Glu Glu Phe
20 25 30

Tyr Gln Ser Thr Cys Ser Ala Val Ser Arg Gly Tyr Phe Ser Ala Leu
35 40 45

Arg Thr Gly Trp Tyr Thr Ser Val Ile Thr Ile Glu Leu Ser Asn Ile
50 55 60

Lys Glu Thr Lys Cys Asn Gly Thr Asp Thr Lys Val Lys Leu Ile Lys
65 70 75 80

Gln Glu Leu Asp Lys Tyr Lys Asn Ala Val Thr Glu Leu Gln Leu Leu
85 90 95

Thr Gln Asn Pro Ala Ala Asn Asn Arg Ala Arg Arg Glu Ala Pro Gln
100 105 110

Tyr Met Asn Tyr Thr Ile Asn Thr Thr Lys Asn Leu Asn Val Ser Ile
115 120 125

Ser Lys Lys Arg Lys Arg Arg Phe Leu Gly Phe Leu Leu Gly Val Gly
130 135 140

Ser Ala Ile Ala Ser Gly Ile Ala Val Ser Lys Val Leu His Leu Glu
145 150 155 160

Gly Glu Val Asn Lys Ile Lys Asn Ala Leu Leu Ser Thr Asn Lys Ala
165 170 175

Val Val Ser Leu Ser Asn Gly Val Ser Val Leu Thr Ser Lys Val Leu
180 185 190

Asp Leu Lys Ser Tyr Ile Asn Asn Gln Leu Leu Pro Ile Val Asn Gln
195 200 205

Gln Ser Cys Arg Ile Ser Asn Ile Glu Thr Val Ile Glu Phe Gln Gln
210 215 220

Lys Asn Ser Arg Leu Leu Glu Ile Thr Arg Glu Phe Ser Val Asn Ala
225 230 235 240

Gly Val Thr Thr Pro Leu Ser Thr Tyr Met Leu Thr Asn Ser Glu Leu
245 250 255

Leu Ser Leu Ile Asn Asp Met Pro Ile Thr Asn Asp Gln Lys Lys Leu
260 265 270

Met Ser Ser Asn Val Gln Ile Val Arg Gln Gln Ser Tyr Ser Ile Met
275 280 285

Ser Ile Ile Lys Glu Glu Val Leu Ala Tyr Val Val Gln Leu Pro Ile
290 295 300

Tyr Gly Val Ile Asp Thr Pro Cys Trp Lys Leu His Thr Ser Pro Leu
305 310 315 320

Cys Thr Thr Asn Ile Lys Glu Gly Ser Asn Ile Cys Leu Thr Arg Thr
325 330 335

Asp Arg Gly Trp Tyr Cys Asp Asn Ala Gly Ser Val Ser Phe Phe Pro
340 345 350

Gln Ala Asp Thr Cys Lys Val Gln Ser Asn Arg Val Phe Cys Asp Thr
355 360 365

Met Asn Ser Leu Thr Leu Pro Ser Glu Val Ser Leu Cys Asn Thr Asp 370 375 380

Ile Phe Asn Ser Lys Tyr Asp Cys Lys Ile Met Thr Ser Lys Thr Asp
385 390 395 400

Ile Ser Ser Ser Val Ile Thr Ser Leu Gly Ala Ile Val Ser Cys Tyr
405 410 415

Gly Lys Thr Lys Cys Thr Ala Ser Asn Lys Asn Arg Gly Ile Ile Lys
420 425 430

Thr Phe Ser Asn Gly Cys Asp Tyr Val Ser Asn Lys Gly Val Asp Thr
435 440 445

Val Ser Val Gly Asn Thr Leu Tyr Tyr Val Asn Lys Leu Glu Gly Lys
450 455 460

Asn Leu Tyr Val Lys Gly Glu Pro Ile Ile Asn Tyr Tyr Asp Pro Leu
465 470 475 480

Val Phe Pro Ser Asp Glu Phe Asp Ala Ser Ile Ser Gln Val Asn Glu
485 490 495

Lys Ile Asn Gln Ser Leu Ala Phe Ile Arg Arg Ser Asp Glu Leu Leu
500 505 510

His Asn Val Asn Thr Gly Lys Ser Thr Thr Asn Ile Met Ile Thr Thr
515 520 525

Ile Ile Ile Val Ile Ile Val Val Leu Leu Ser Leu Ile Ala Ile Gly
530 535 540

Leu Leu Leu Tyr Cys Lys Ala Lys Asn Thr Pro Val Thr Leu Ser Lys
545 550 555 560

Asp Gln Leu Ser Gly Ile Asn Asn Ile Ala Phe Ser Lys
565 570

<210> SEQ ID NO 12
<211> LENGTH: 574
<212> TYPE: PRT
<213> ORGANISM: Artificial Sequence
<220> FEATURE:
<223> OTHER INFORMATION: Synthetic

<400> SEQUENCE: 12

Met Glu Leu Pro Ile Leu Lys Ala Asn Ala Ile Thr Thr Ile Leu Ala
1 5 10 15

Ala Val Thr Phe Cys Phe Ala Ser Ser Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Met Lys
65 70 75 80

Gln Glu Leu Asp Lys Tyr Lys Asn Ala Val Thr Glu Leu Gln Leu Leu
85 90 95

Met Gln Ser Thr Pro Ala Ala Asn Asn Arg Ala Arg Arg Glu Leu Pro
100 105 110

Arg Phe Met Asn Tyr Thr Leu Asn Asn Thr Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Ile Ala Val Ser Lys Val Leu His Leu
145 150 155 160

Glu Gly Glu Val Asn Lys Ile Lys Ser Ala Leu Leu Ser Thr Asn Lys
165 170 175

```
Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Val Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 13
<211> LENGTH: 574
<212> TYPE: PRT

<213> ORGANISM: Artificial Sequence
<220> FEATURE:
<223> OTHER INFORMATION: Synthetic

<400> SEQUENCE: 13

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Arg Ser Cys Arg Ile Ser Asn Ile Glu Thr Val Ile Glu Phe Gln
    210                 215                 220

His Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400
```

```
Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Glu Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 14
<211> LENGTH: 574
<212> TYPE: PRT
<213> ORGANISM: Artificial Sequence
<220> FEATURE:
<223> OTHER INFORMATION: Synthetic

<400> SEQUENCE: 14

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190
```

-continued

```
Leu Asp Leu Lys Asn Tyr Ile Asp Lys Gln Val Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 15
<211> LENGTH: 1791
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<222> LOCATION: (134)..(134)
<223> OTHER INFORMATION: n is a, c, g, or t

<400> SEQUENCE: 15

```
ctcgagggca atatacaatg gagttgctaa tcctcaaagc aaatgcaatt accacaatcc     60

tcactgcagt cacattttgt tttgcttctg gtcaaaacat cactgaagaa ttttatcaat    120

caacatgcag tgcngttagc aaaggctatc ttagtgctct gagaactggt tggtatacca    180

gtgttataac tatagaatta agtaatatca agaaaaataa gtgtaatgga acagatgcta    240

aggtaaaatt gataaaacaa gaattagata aatataaaaa tgctgtaaca gaattgcagt    300

tgctcatgca aagcacacaa gcaacaaaca atcgagccag aagagaacta ccaaggttta    360

tgaattatac actcaacaat gccaaaaaaa ccaatgtaac attaagcaag aaaaggaaaa    420

gaagatttct tggtttttg ttaggtgttg gatctgcaat cgccagtggc gttgctgtat    480

ctaaggtcct gcacctagaa ggggaagtga acaagatcaa aagtgctcta ctatccacaa    540

acaaggctgt agtcagctta tcaaatggag ttagtgtctt aaccagcaaa gtgttagacc    600

tcaaaaacta tatagataaa caagtgttac ctattgtgaa caagcaaagc tgcagcatat    660

caaatataga aactgtgata gagttccaac aaaagaacaa cagactacta gagattacca    720

gggaatttag tgttaatgca ggtgtaacta cacctgtaag cacttacatg ttaactaata    780

gtgaattatt gtcattaatc aatgatatgc ctataacaaa tgatcagaaa aagttaatgt    840

ccaacaatgt tcaaatagtt agacagcaaa gttactctat catgtccata ataaaagagg    900

aagtcttagc atatgtagta caattaccac tatatggtgt tatagataca ccctgttgga    960

aactacacac atcccctcta tgtacaacca acacaaaaga agggtccaac atctgtttaa   1020

caagaactga cagaggatgg tactgtgaca atgcaggatc agtatctttc ttcccacaag   1080

ctgaaacatg taaagttcaa tcaaatcgag tattttgtga cacaatgaac agtttaacat   1140

taccaagtga agtaaatctc tgcaatgttg acatattcaa ccccaaatat gattgtaaaa   1200

ttatgacttc aaaaacagat gtaagcagct ccgttatcac atctctagga gccattgtgt   1260

catgctatgg caaaactaaa tgtacagcat ccaataaaaa tcgtggaatc ataaagacat   1320

tttctaacgg gtgcgattat gtatcaaata aaggggtgga cactgtgtct gtaggtaaca   1380

cattatatta tgtaaataag caagaaggta aaagtctcta tgtaaaaggt gaaccaataa   1440

taaatttcta tgacccatta gtattcccct ctgatgaatt tgatgcatca atatctcaag   1500

tcaacgagaa gattaaccag agcctagcat ttattcgtaa atccgatgaa ttattacata   1560

atgtaaatgc tggtaaatcc accacaaata tcatgataac tactataatt atagtgatta   1620

tagtaatatt gttatcatta attgctgttg gactgctctt atactgtaag gccagaagca   1680

caccagtcac actaagcaaa gatcaactga gtggtataaa taatattgca tttagtaact   1740

aaataaaaat agcacctaat catgttctta caatggttta ctatctggcc a             1791
```

<210> SEQ ID NO 16
<211> LENGTH: 524
<212> TYPE: PRT
<213> ORGANISM: Artificial Sequence
<220> FEATURE:
<223> OTHER INFORMATION: Synthetic

<400> SEQUENCE: 16

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
```

-continued

```
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Val Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445
```

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Ala Gly Lys Ser Thr Thr Asn
515 520

<210> SEQ ID NO 17
<211> LENGTH: 26
<212> TYPE: PRT
<213> ORGANISM: Artificial Sequence
<220> FEATURE:
<223> OTHER INFORMATION: Synthetic

<400> SEQUENCE: 17

Ile Met Ile Thr Thr Ile Ile Ile Val Ile Ile Val Ile Leu Leu Ser
1 5 10 15

Leu Ile Ala Val Gly Leu Leu Leu Tyr Cys
20 25

<210> SEQ ID NO 18
<211> LENGTH: 24
<212> TYPE: PRT
<213> ORGANISM: Artificial Sequence
<220> FEATURE:
<223> OTHER INFORMATION: Synthetic

<400> SEQUENCE: 18

Lys Ala Arg Ser Thr Pro Val Thr Leu Ser Lys Asp Gln Leu Ser Gly
1 5 10 15

Ile Asn Asn Ile Ala Phe Ser Asn
20

<210> SEQ ID NO 19
<211> LENGTH: 17
<212> TYPE: DNA
<213> ORGANISM: Artificial Sequence
<220> FEATURE:
<223> OTHER INFORMATION: Synthetic

<400> SEQUENCE: 19
ctcgagggca atataca 17

<210> SEQ ID NO 20
<211> LENGTH: 1572
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (117)..(117)
<223> OTHER INFORMATION: n is a, c, g, or t

<400> SEQUENCE: 20
atggagttgc taatcctcaa agcaaatgca attaccacaa tcctcactgc agtcacattt 60
tgttttgctt ctggtcaaaa catcactgaa gaattttatc aatcaacatg cagtgcngtt 120
agcaaaggct atcttagtgc tctgagaact ggttggtata ccagtgttat aactatagaa 180
ttaagtaata tcaagaaaaa taagtgtaat ggaacagatg ctaaggtaaa attgataaaa 240
caagaattag ataaatataa aaatgctgta acagaattgc agttgctcat gcaaagcaca 300
caagcaacaa acaatcgagc cagaagagaa ctaccaaggt ttatgaatta tacactcaac 360
aatgccaaaa aaaccaatgt aacattaagc aagaaaagga aaagaagatt tcttggtttt 420
ttgttaggtg ttggatctgc aatcgccagt ggcgttgctg tatctaaggt cctgcaccta 480
gaaggggaag tgaacaagat caaaagtgct ctactatcca caaacaaggc tgtagtcagc 540
ttatcaaatg gagttagtgt cttaaccagc aaagtgttag acctcaaaaa ctatatagat 600
aaacaagtgt tacctattgt gaacaagcaa agctgcagca tatcaaatat agaaactgtg 660
atagagttcc aacaaaagaa caacagacta ctagagatta ccagggaatt tagtgttaat 720
gcaggtgtaa ctacacctgt aagcacttac atgttaacta atagtgaatt attgtcatta 780
atcaatgata tgcctataac aaatgatcag aaaaagttaa tgtccaacaa tgttcaaata 840
gttagacagc aaagttactc tatcatgtcc ataataaaag aggaagtctt agcatatgta 900
gtacaattac cactatatgg tgttatagat acaccctgtt ggaaactaca cacatcccct 960
ctatgtacaa ccaacacaaa agaagggtcc aacatctgtt taacaagaac tgacagagga 1020
tggtactgtg acaatgcagg atcagtatct ttcttcccac aagctgaaac atgtaaagtt 1080
caatcaaatc gagtattttg tgacacaatg aacagtttaa cattaccaag tgaagtaaat 1140
ctctgcaatg ttgacatatt caaccccaaa tatgattgta aaattatgac ttcaaaaaca 1200
gatgtaagca gctccgttat cacatctcta ggagccattg tgtcatgcta tggcaaaact 1260
aaatgtacag catccaataa aaatcgtgga atcataaaga cattttctaa cgggtgcgat 1320
tatgtatcaa ataaaggggt ggacactgtg tctgtaggta acacattata ttatgtaaat 1380
aagcaagaag gtaaaagtct ctatgtaaaa ggtgaaccaa taataaattt ctatgaccca 1440
ttagtattcc cctctgatga atttgatgca tcaatatctc aagtcaacga gaagattaac 1500
cagagcctag catttattcg taaatccgat gaattattac ataatgtaaa tgctggtaaa 1560
tccaccacaa at 1572

<210> SEQ ID NO 21
<211> LENGTH: 77
<212> TYPE: DNA
<213> ORGANISM: Artificial Sequence
<220> FEATURE:
<223> OTHER INFORMATION: Synthetic

<400> SEQUENCE: 21
atcatgataa ctactataat tatagtgatt atagtaatat tgttatcatt aattgctgtt 60
ggactgctct tatactg 77

<210> SEQ ID NO 22
<211> LENGTH: 73
<212> TYPE: DNA
<213> ORGANISM: Artificial Sequence
<220> FEATURE:
<223> OTHER INFORMATION: Synthetic

<400> SEQUENCE: 22
taaggccaga agcacaccag tcacactaag caaagatcaa ctgagtggta taaataatat 60
tgcatttagt aac 73

<210> SEQ ID NO 23
<211> LENGTH: 52
<212> TYPE: DNA
<213> ORGANISM: Artificial Sequence
<220> FEATURE:
<223> OTHER INFORMATION: Synthetic

<400> SEQUENCE: 23
taaataaaaa tagcacctaa tcatgttctt acaatggttt actatctggc ca 52

<210> SEQ ID NO 24
<211> LENGTH: 1734
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1572)
<223> OTHER INFORMATION: RSV F sequence
<220> FEATURE:
<221> NAME/KEY: misc_feature
<222> LOCATION: (1573)..(1731)
<223> OTHER INFORMATION: NDV F sequence

<400> SEQUENCE: 24
atggagttgc taatcctcaa agcaaatgca attaccacaa tcctcactgc agtcacattt 60
tgttttgctt ctggtcaaaa catcactgaa gaattttatc aatcaacatg cagtgcngtt 120
agcaaaggct atcttagtgc tctgagaact ggttggtata ccagtgttat aactatagaa 180
ttaagtaata tcaagaaaaa taagtgtaat ggaacagatg ctaaggtaaa attgataaaa 240
caagaattag ataaatataa aaatgctgta acagaattgc agttgctcat gcaaagcaca 300
caagcaacaa acaatcgagc cagaagagaa ctaccaaggt ttatgaatta tacactcaac 360
aatgccaaaa aaaccaatgt aacattaagc aagaaaagga aaagaagatt tcttggtttt 420
ttgttaggtg ttggatctgc aatcgccagt ggcgttgctg tatctaaggt cctgcaccta 480
gaaggggaag tgaacaagat caaaagtgct ctactatcca caaacaaggc tgtagtcagc 540
ttatcaaatg gagttagtgt cttaaccagc aaagtgttag acctcaaaaa ctatatagat 600
aaacaagtgt tacctattgt gaacaagcaa agctgcagca tatcaaatat agaaactgtg 660
atagagttcc aacaaaagaa caacagacta ctagagatta ccagggaatt tagtgttaat 720
gcaggtgtaa ctacacctgt aagcacttac atgttaacta atagtgaatt attgtcatta 780
atcaatgata tgcctataac aaatgatcag aaaaagttaa tgtccaacaa tgttcaaata 840
gttagacagc aaagttactc tatcatgtcc ataataaaag aggaagtctt agcatatgta 900
gtacaattac cactatatgg tgttatagat acaccctgtt ggaaactaca cacatcccct 960
ctatgtacaa ccaacacaaa agaagggtcc aacatctgtt taacaagaac tgacagagga 1020
tggtactgtg acaatgcagg atcagtatct ttcttcccac aagctgaaac atgtaaagtt 1080
caatcaaatc gagtattttg tgacacaatg aacagtttaa cattaccaag tgaagtaaat 1140
ctctgcaatg ttgacatatt caaccccaaa tatgattgta aaattatgac ttcaaaaaca 1200
gatgtaagca gctccgttat cacatctcta ggagccattg tgtcatgcta tggcaaaact 1260
aaatgtacag catccaataa aaatcgtgga atcataaaga cattttctaa cgggtgcgat 1320
tatgtatcaa ataaaggggt ggacactgtg tctgtaggta acacattata ttatgtaaat 1380
aagcaagaag gtaaaagtct ctatgtaaaa ggtgaaccaa taataaattt ctatgaccca 1440
ttagtattcc cctctgatga atttgatgca tcaatatctc aagtcaacga gaagattaac 1500
cagagcctag catttattcg taaatccgat gaattattac ataatgtaaa cgccgggaag 1560
agtactacta atctcattac ctatatcgct ttaactgcca tatctcttgt ttgcggtata 1620
cttagtctgg ttctagcatg ctacctaatg tacaagcaaa aggcgcaaca aaagaccttg 1680
ttatggcttg ggaataatac cctgggtcag atgagagcca ctacaaaaat gtga 1734

<210> SEQ ID NO 25
<211> LENGTH: 1800
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1536)
<223> OTHER INFORMATION: RSV sequence
<220> FEATURE:
<221> NAME/KEY: misc_feature
<222> LOCATION: (1537)..(1623)
<223> OTHER INFORMATION: NDV HR2 domain
<220> FEATURE:
<221> NAME/KEY: misc_feature
<222> LOCATION: (1537)..(1797)
<223> OTHER INFORMATION: NDV sequence

<400> SEQUENCE: 25
atggagttgc taatcctcaa agcaaatgca attaccacaa tcctcactgc agtcacattt 60
tgttttgctt ctggtcaaaa catcactgaa gaattttatc aatcaacatg cagtgcngtt 120
agcaaaggct atcttagtgc tctgagaact ggttggtata ccagtgttat aactatagaa 180
ttaagtaata tcaagaaaaa taagtgtaat ggaacagatg ctaaggtaaa attgataaaa 240
caagaattag ataaatataa aaatgctgta acagaattgc agttgctcat gcaaagcaca 300
caagcaacaa acaatcgagc cagaagagaa ctaccaaggt ttatgaatta tacactcaac 360
aatgccaaaa aaaccaatgt aacattaagc aagaaaagga aaagaagatt tcttggtttt 420
ttgttaggtg ttggatctgc aatcgccagt ggcgttgctg tatctaaggt cctgcaccta 480
gaaggggaag tgaacaagat caaaagtgct ctactatcca caaacaaggc tgtagtcagc 540
ttatcaaatg gagttagtgt cttaaccagc aaagtgttag acctcaaaaa ctatatagat 600
aaacaagtgt tacctattgt gaacaagcaa agctgcagca tatcaaatat agaaactgtg 660
atagagttcc aacaaaagaa caacagacta ctagagatta ccagggaatt tagtgttaat 720
gcaggtgtaa ctacacctgt aagcacttac atgttaacta atagtgaatt attgtcatta 780
atcaatgata tgcctataac aaatgatcag aaaaagttaa tgtccaacaa tgttcaaata 840
gttagacagc aaagttactc tatcatgtcc ataataaaag aggaagtctt agcatatgta 900
gtacaattac cactatatgg tgttatagat acaccctgtt ggaaactaca cacatcccct 960
ctatgtacaa ccaacacaaa agaagggtcc aacatctgtt taacaagaac tgacagagga 1020
tggtactgtg acaatgcagg atcagtatct ttcttcccac aagctgaaac atgtaaagtt 1080
caatcaaatc gagtattttg tgacacaatg aacagtttaa cattaccaag tgaagtaaat 1140
ctctgcaatg ttgacatatt caaccccaaa tatgattgta aaattatgac ttcaaaaaca 1200
gatgtaagca gctccgttat cacatctcta ggagccattg tgtcatgcta tggcaaaact 1260
aaatgtacag catccaataa aaatcgtgga atcataaaga cattttctaa cgggtgcgat 1320
tatgtatcaa ataaaggggt ggacactgtg tctgtaggta acacattata ttatgtaaat 1380
aagcaagaag gtaaaagtct ctatgtaaaa ggtgaaccaa taataaattt ctatgaccca 1440
ttagtattcc cctctgatga atttgatgca tcaatatctc aagtcaacga gaagattaac 1500
cagagcctag catttattcg taaatccgat gaattacttg ggaacgtcaa caactcgata 1560
agtaatgctt tggataagtt agaggaaagc aacagcaaac tagacaaagt caatgtcaaa 1620
ctgaccagca catctgctct cattacctat atcgctttaa ctgccatatc tcttgtttgc 1680
ggtatactta gtctggttct agcatgctac ctaatgtaca agcaaaaggc gcaacaaaag 1740
accttgttat ggcttgggaa taataccctg ggtcagatga gagccactac aaaaatgtga 1800

<210> SEQ ID NO 26
<211> LENGTH: 578
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(525)
<223> OTHER INFORMATION: RSV sequence
<220> FEATURE:
<221> NAME/KEY: MISC_FEATURE
<222> LOCATION: (526)..(578)
<223> OTHER INFORMATION: NDV sequence
<220> FEATURE:
<221> NAME/KEY: MISC_FEATURE
<222> LOCATION: (578)..(578)
<223> OTHER INFORMATION: The residue at this position can be any amino acid.

<400> SEQUENCE: 26

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Lys Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Gln Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Gln Val Leu Pro Ile Val Asn
195 200 205

Lys Gln Ser Cys Ser Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile

-continued

```
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Leu Ile Thr Tyr
        515                 520                 525

Ile Ala Leu Thr Ala Ile Ser Leu Val Cys Gly Ile Leu Ser Leu Val
    530                 535                 540

Leu Ala Cys Tyr Leu Met Tyr Lys Gln Lys Ala Gln Gln Lys Thr Leu
545                 550                 555                 560

Leu Trp Leu Gly Asn Asn Thr Leu Gly Gln Met Arg Ala Thr Thr Lys
                565                 570                 575

Met Xaa
```

<210> SEQ ID NO 27
<211> LENGTH: 600
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(513)
<223> OTHER INFORMATION: RSV sequence
<220> FEATURE:
<221> NAME/KEY: MISC_FEATURE
<222> LOCATION: (510)..(542)
<223> OTHER INFORMATION: NDV HR2 domain
<220> FEATURE:
<221> NAME/KEY: MISC_FEATURE
<222> LOCATION: (514)..(600)
<223> OTHER INFORMATION: NDV sequence
<220> FEATURE:
<221> NAME/KEY: MISC_FEATURE
<222> LOCATION: (600)..(600)

<223> OTHER INFORMATION: The residue at this position can be any amino acid.

<400> SEQUENCE: 27

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Val Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400
```

```
Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Gly Asn Val Asn Asn Ser Ile Ser Asn Ala Leu Asp Lys Leu Glu
        515                 520                 525

Glu Ser Asn Ser Lys Leu Asp Lys Val Asn Val Lys Leu Thr Ser Thr
    530                 535                 540

Ser Ala Leu Ile Thr Tyr Ile Ala Leu Thr Ala Ile Ser Leu Val Cys
545                 550                 555                 560

Gly Ile Leu Ser Leu Val Leu Ala Cys Tyr Leu Met Tyr Lys Gln Lys
                565                 570                 575

Ala Gln Gln Lys Thr Leu Leu Trp Leu Gly Asn Asn Thr Leu Gly Gln
580                 585                 590

Met Arg Ala Thr Thr Lys Met Xaa
595                 600
```

<210> SEQ ID NO 28
<211> LENGTH: 846
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(141)
<223> OTHER INFORMATION: NDV HN sequences
<220> FEATURE:
<221> NAME/KEY: misc_feature
<222> LOCATION: (142)..(845)
<223> OTHER INFORMATION: RSV G sequences

<400> SEQUENCE: 28

```
atgaaccgcg cagtttgcca agttgcgcta gagaatgatg aaagggaagc gaagaataca      60

tggcgcttgg tattccggat cgcaatctta cttttaacag taatgacctt agccatctct     120

gcggccgccc tggcatatag tgcgaatcat aaggtcacac ccacgaccgc aatcattcag     180

gacgctacta gccaaatcaa aaacacaacc cctacgtatt tgactcagaa cccacaactg     240

ggtatttcac cgtcgaatcc cagtgaaatc acctcccaga tcacaactat tcttgcctct     300

accacgcctg gcgttaagag cacactccaa tcaactaccg taaagacgaa aaacacaact     360

accacccaga cgcagcccatc caagccgaca actaaacaaa ggcagaacaa gcccccttcg     420

aagccaaata acgatttcca cttcgaggtg tttaacttcg tcccgtgtag tatctgctct     480

aataacccca cctgttgggc tatttgcaaa agaatcccta acaagaagcc aggaaaaaag     540

acgacaacta aacccaccaa gaagcctacg ttgaaaacaa ctaagaagga cccgaaacca     600

caaaccacga agagcaaaga agttcccaca actaagccta ccgaggaacc gacgatcaat     660

acaactaaga ccaacattat cacgacactg ctcacttcaa ataccactgg taacccagag     720
```

```
ctgacctccc agatggaaac cttccattcg acgagttctg agggcaaccc cagcccttcc    780

caagtatcaa caacttcgga atacccatct cagcccagta gccctccgaa taccccacga    840

caataa                                                               846


<210> SEQ ID NO 29
<211> LENGTH: 283
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(48)
<223> OTHER INFORMATION: NDV HN sequence
<220> FEATURE:
<221> NAME/KEY: MISC_FEATURE
<222> LOCATION: (49)..(282)
<223> OTHER INFORMATION: RSV G sequence

<400> SEQUENCE: 29

Met Asn Arg Ala Val Cys Gln Val Ala Leu Glu Asn Asp Glu Arg Glu
1               5                   10                  15

Ala Lys Asn Thr Trp Arg Leu Val Phe Arg Ile Ala Ile Leu Leu Leu
            20                  25                  30

Thr Val Met Thr Leu Ala Ile Ser Ala Ala Ala Leu Ala Tyr Ser Ala
        35                  40                  45

Asn His Lys Val Thr Pro Thr Thr Ala Ile Ile Gln Asp Ala Thr Ser
    50                  55                  60

Gln Lys Ile Lys Asn Thr Thr Pro Thr Tyr Leu Thr Gln Asn Pro Gln
65                  70                  75                  80

Leu Gly Ile Ser Pro Ser Asn Pro Ser Glu Ile Thr Ser Gln Ile Thr
                85                  90                  95

Thr Ile Leu Ala Ser Thr Thr Pro Gly Val Lys Ser Thr Leu Gln Ser
            100                 105                 110

Thr Thr Val Lys Thr Lys Asn Thr Thr Thr Thr Gln Thr Gln Pro Ser
        115                 120                 125

Lys Pro Thr Thr Lys Gln Arg Gln Asn Lys Pro Pro Ser Lys Pro Asn
    130                 135                 140

Asn Asp Phe His Phe Glu Val Phe Asn Phe Val Pro Cys Ser Ile Cys
145                 150                 155                 160

Ser Asn Asn Pro Thr Cys Trp Ala Ile Cys Lys Arg Ile Pro Asn Lys
                165                 170                 175

Lys Pro Gly Lys Lys Thr Thr Thr Lys Pro Thr Lys Lys Pro Thr Leu
            180                 185                 190

Lys Thr Thr Lys Lys Asp Pro Lys Pro Gln Thr Thr Lys Ser Lys Glu
        195                 200                 205

Val Pro Thr Thr Lys Pro Thr Glu Glu Pro Thr Ile Asn Thr Thr Lys
    210                 215                 220

Thr Asn Ile Ile Thr Thr Leu Leu Thr Ser Asn Thr Thr Gly Asn Pro
225                 230                 235                 240

Glu Leu Thr Ser Gln Met Glu Thr Phe His Ser Thr Ser Ser Glu Gly
                245                 250                 255

Asn Pro Ser Pro Ser Gln Val Ser Thr Thr Ser Glu Tyr Pro Ser Gln
            260                 265                 270

Pro Ser Ser Pro Pro Asn Thr Pro Arg Gln Asn
        275                 280
```

RESPIRATORY SYNCTIAL VIRUS (RSV) SEQUENCES FOR PROTEIN EXPRESSION AND VACCINES

This application is the U.S. national stage filing of co-pending PCT application No. PCT/US2009/05383, filed on Sep. 30, 2009, which claims priority to U.S. provisional Application Ser. No. 61/101,340, filed Sep. 30, 2008, which is herein incorporated by reference in its entirety for all purposes.

FIELD OF THE INVENTION

The invention provides RSV fusion (F) protein ectodomain polypeptide sequences and nucleotide sequences encoding them, as well as cells containing the invention's polypeptide and nucleotide sequences. The invention further provides virus-like particles (VLPs) that contain the invention's polypeptides, and methods for using the VLPs for protein expression and vaccine formulation. Also provided are methods for distinguishing between subjects immunized with the invention's compositions and subjects infected with RSV.

BACKGROUND OF THE INVENTION

Human Respiratory Syncytial virus (RSV) is the leading cause of severe lower respiratory tract disease in infants and young children, and may repeatedly cause infection in the same individual. RSV also causes disease in immune-compromised adults and in the elderly. To date, there is no safe and effective vaccine against RSV and against other infective agents (virus, bacteria, etc.). Thus, there remains a need for vaccines against RSV and vaccines against other infective agents.

SUMMARY OF THE INVENTION

The invention provides in one embodiment the discovery of a Respiratory Syncytial Virus Fusion (F) protein (RSV F-LM) ectodomain polypeptide SEQ ID NO:16. The invention also provides in one embodiment the discovery that RSV F-LM ectodomain sequence in each of the chimeric protein RSV F/HR2 and chimeric protein RSV F/F is expressed in cells, and incorporated into VLPs. These VLPs are released from cells at high efficiency and are immunogenic and protective against RSV infection. The invention also provides in one embodiment the discovery that expressing RSV H/G together with the chimeric protein RSV F/HR2 and/or chimeric protein RSV F/F results in a significant increase in the level of expression of the chimeric protein RSV F/HR2 and/or chimeric protein RSV F/F, and in the increased efficiency of extracellular release of VLPs (VLP-H/G+F/HR2F and VLP-H/G+F/F). Moreover, the invention provides in one embodiment the discovery that the released VLP-H/G+F/HR2F and VLP-H/G+F/F are immunogenic and protective against RSV infection. The invention additionally provides in one embodiment a virus-like particle (VLP) comprising any one or more of the polypeptides disclosed herein, including the RSV F-LM ectodomain sequence. In one embodiment the VLP is purified. In another embodiment, the VLP is immunogenic. In a further embodiment, the VLP is comprised in a vaccine. In one embodiment, the VLP is a Newcastle disease VLP (ND VLP) comprising any one or more of the polypeptides disclosed herein, as exemplified by, but not limited to, the RSV F-LM ectodomain sequence.

Thus, in one embodiment, the invention provides a recombinant polypeptide sequence comprising a first polypeptide having at least 95% identity to RSV F-LM ectodomain polypeptide SEQ ID NO:16. In a particular embodiment, the first polypeptide having at least 95% identity to RSV F-LM ectodomain polypeptide SEQ ID NO:16 is not a wild type RSV F ectodomain. In another embodiment, the first polypeptide comprises at least one of (a) alanine at a position corresponding to alanine$^{102}$ of SEQ ID NO:14, (b) valine at a position corresponding to valine$^{379}$ of SEQ ID NO:14, and (c) valine at a position corresponding to valine$^{447}$ of SEQ ID NO:14. In an alternative embodiment, the first polypeptide sequence comprises RSV F-LM protein ectodomain SEQ ID NO:16. In a further embodiment, the first polypeptide sequence comprises RSV F-LM protein full-length sequence SEQ ID NO:14. In a particular embodiment, the first polypeptide sequence comprises RSV F-LM protein encoded by the nucleotide sequence SEQ ID NO:15.

In one embodiment the recombinant polypeptide sequence is chimeric comprising the first polypeptide operably linked to a second polypeptide. In a particular embodiment, the second polypeptide comprises one or more RSV protein. The RSV protein may be selected from the group consisting of transmembrane domain, cytoplasmic domain, M protein, N protein, G protein, group A protein, and group B protein. In an alternate embodiment, the RSV protein comprises RSV F-LM transmembrane domain having at least 95% identity to SEQ ID NO:17. In a further alternate embodiment, the RSV protein comprises RSV F-LM cytoplasmic domain having at least 95% identity to SEQ ID NO:18. In a particularly preferred embodiment, the RSV protein comprises RSV F/HR2 polypeptide sequence (Example 8). In a further embodiment, the RSV F/HR2 polypeptide sequence comprises SEQ ID NO:27. In another embodiment, the second polypeptide further comprises RSV H/G polypeptide sequence, as exemplified by VLP-H/G+F/HR2F that contains RSV F/HR2 and additionally RSV H/G. In a particular embodiment, the RSV H/G polypeptide sequence comprises a sequence having at least 95% identity to SEQ ID NO:29.

In another particularly preferred embodiment, the RSV protein comprises RSV F/F polypeptide sequence (Examples 4-7 and 10). In one embodiment, the RSV F/F polypeptide sequence comprises SEQ ID NO:26. In a more preferred embodiment, the second polypeptide further comprises RSV H/G polypeptide sequence, as exemplified by VLP-H/G+F/F that contains RSV F/F and additionally RSV H/G. The data in Example 4 show that RSV F protein chimera (F/F) is incorporated into ND VLPs in the presence of RSV H/G chimera protein with significantly higher efficiency (greater than 10 fold) than in the absence of H/G (see lanes 4 and 5, lanes 10 and 11, and lanes 16 and 17 of FIG. 6). Also the data in Example 4 also show that incorporation of H/G and F/F into ND VLPs is significantly increased over incorporation of intact G and F proteins into VLPs formed with RSV proteins alone (see arrows). In a particular embodiment, the RSV H/G polypeptide sequence comprises a sequence having at least 95% identity to SEQ ID NO:29.

In one embodiment the recombinant polypeptide sequence is chimeric comprising the first polypeptide operably linked to a second polypeptide, wherein said second polypeptide is a polypeptide of interest. In a particular embodiment, the second polypeptide comprises one or more NDV protein. In one embodiment, the NDV protein comprises a cytoplasmic domain of an NDV protein selected from the group consisting of Matrix (M) protein, Fusion (F) protein, Nucleocapsid (NP) protein, and heamagglutinin-neuraminidase (HN or G) protein. In an alternative embodiment, the NDV protein comprises at least a portion of a transmembrane domain of an NDV protein selected from the group consisting of Matrix (M) protein, Fusion (F) protein, Nucleocapsid (NP) protein, and heamagglutinin-neuraminidase (HN or G) protein. In a particularly preferred embodiment, the NDV protein comprises RSV F/HR2 polypeptide sequence (Example 8). In a further embodiment, the RSV F/HR2 polypeptide sequence comprises SEQ ID NO:27. In a more preferred embodiment, the second polypeptide further comprises RSV H/G polypeptide sequence, as exemplified by VLP-H/G+F/HR2F, which contains RSV F/HR2 and additionally RSV H/G. In a particular embodiment, the RSV H/G polypeptide sequence comprises a sequence having at least 95% identity to SEQ ID NO:29.

In an alternative preferred embodiment, the NDV protein comprises RSV F/F polypeptide sequence (Examples 4-7 and 10). In one embodiment, the RSV F/F polypeptide sequence comprises SEQ ID NO:26. In a more preferred embodiment, the second polypeptide further comprises RSV H/G polypeptide sequence, as exemplified by VLP-H/G+F/F, which contains RSV F/F and additionally RSV H/G. Example 4 shows that RSV F protein chimera (F/F) is incorporated into ND VLPs in the presence of RSV H/G chimera protein with significantly higher efficiency (greater than 10 fold) than in the absence of H/G (see lanes 4 and 5, lanes 10 and 11, and lanes 16 and 17 of FIG. 6). Also the data in Example 4 also show that incorporation of H/G and F/F into ND VLPs is significantly increased over incorporation of intact G and F proteins into VLPs formed with RSV proteins alone (see arrows). In a particularly preferred embodiment, the RSV H/G sequence comprises a sequence having at least 95% identity to SEQ ID NO:29.

In one embodiment, one or more of the recombinant polypeptide sequences described herein is comprised in a virus like particle (VLP).

The invention also provides in one embodiment a recombinant polypeptide sequence comprising a first polypeptide having at least 95% identity to RSV F protein ectodomain polypeptide SEQ ID NO:16, wherein the first polypeptide comprises at least one of (a) lysine at a position corresponding to amino acid 66 of SEQ ID NO:16, (b) glutamine at a position corresponding to amino acid 101 of SEQ ID NO:16, and (c) valine at a position corresponding to amino acid 203 of SEQ ID NO:16. In one embodiment, the first polypeptide having at least 95% identity to RSV F protein ectodomain polypeptide SEQ ID NO:16 is not a wild-type RSV F protein ectodomain. In one preferred embodiment, the first polypeptide comprises RSV F-LM protein ectodomain SEQ ID NO:16. In an alternative embodiment, the first polypeptide comprises a conservative amino acid substitution of one or more of the lysine, the glutamine and the valine. In another alternative embodiment, the first polypeptide is encoded by a recombinant nucleotide sequence comprising SEQ ID NO:20 that encodes RSV F-LM protein ectodomain. Preferably, the recombinant nucleotide sequence comprises SEQ ID NO:15 that encodes full length RSV F-LM protein. Alternatively, the recombinant nucleotide sequence comprises a polyadenylation sequence that contains a mutation to AATTAA.

The invention additionally provides in one embodiment a recombinant nucleotide sequence that encodes any one or more of the polypeptides disclosed herein. In one embodiment, the nucleotide sequence comprises SEQ ID NO:20 that encodes RSV F-LM protein ectodomain. In another embodiment, the nucleotide sequence comprises SEQ ID NO:15 that encodes full length RSV F-LM. In a further embodiment, the nucleotide sequence comprises a polyadenylation sequence that contains a mutation to AATTAA.

The invention also provides in one embodiment an expression vector comprising any one or more of the nucleotide sequences disclosed herein.

The invention in one embodiment contemplates within its scope a cell comprising one or more of the nucleotide sequences disclosed herein. The invention also provides in one embodiment a cell comprising any one or more of the polypeptide sequences disclosed herein. In one embodiment, the cell is selected from avian cell, insect cell, and mammalian cell. In another embodiment, the avian cell is an ELL-0 cell (East Lansing Strain of Chicken embryo fibroblast) or an egg cell. In a further embodiment, the insect cell is selected from the group exemplified by *Trichoplusia ni* (Tn5) cell and SF9 cell. In a further embodiment, the mammalian cell is selected from the group exemplified by Chinese hamster ovary CHO-K1 cells, bovine mammary epithelial cells, monkey COS-7 cells, human embryonic kidney 293 cells, baby hamster kidney (BHK) cells, mouse sertoli TM4 cells, monkey kidney CV1 cells, African green monkey kidney VERO-76 cells, human cervical carcinoma HELA cells, canine kidney MDCK cells, buffalo rat liver BRL 3A cells, human lung W138 cells, human liver Hep G2 cells, mouse mammary tumor (MMT) cells, TRI cells, MRC 5 cells, FS4 cells, rat fibroblasts 208F cells, an bovine kidney MDBK cells. In a particular embodiment, the cell is an avian cell; The data in Example 4 additionally show that the efficiency of incorporation of F/F chimera into ND VLPs is significantly higher (from 5 to 8 fold) in VLPs released from avian cells as compared to other cell types. The cell may be in vitro or in vivo. In one embodiment, the cell expresses the polypeptide sequence on the cell's outer surface.

The invention additionally provides in one embodiment a virus-like particle (VLP) comprising any one or more of the polypeptides disclosed herein. In one embodiment the VLP is purified. In another embodiment, the VLP is immunogenic. In a further embodiment, the VLP is comprised in a vaccine. In one embodiment, the VLP is a Newcastle disease VLP (ND VLP).

The invention also provides in one embodiment a vaccine comprising any one or more of the VLPs disclosed herein, and at least one composition selected from adjuvant, diluent and excipient.

The invention further provides in one embodiment a method for producing a VLP, comprising a) providing i) one or more expression vector encoding any one or more of the polypeptides disclosed herein, and ii) a host cell, and b) transfecting the host cell with the vector to produce a VLP. In a particular embodiment, the VLP is produced by extracellular release from the host cell at an efficiency of at least 30%, including any numerical value from 30% to 100%, such as, without limitation, from 40% to 80%, from 50% to 90%, from 30% to 95%, from 30% to 90%, from 30% to 85%, from 30% to 80%, from 30% to 75%, from 30% to 70%, from 30% to 65%, from 30% to 60%, from 30% to 55%, from 30% to 50%, from 30% to 45%, from 30% to 40%, and from 30% to 35%. The data in Example 4 show that RSV F protein chimera (F/F) is incorporated into ND VLPs in the presence of RSV H/G chimera protein with significantly higher efficiency (greater than 10 fold) than in the absence of H/G (see lanes 4 and 5, lanes 10 and 11, and lanes 16 and 17 of FIG. 6). The data in Example 4 also show that incorporation of H/G and F/F into ND VLPs is significantly increased over incorporation of intact G and F proteins into VLPs formed with RSV proteins alone (see arrows). The data in Example 4 additionally show that the efficiency of incorporation of F/F chimera into ND VLPs is significantly higher (from 5 to 8 fold) in VLPs released from avian cells as compared to other cell types. In one embodiment, the method further comprises c) purifying the VLP. In another embodiment, the polypeptide is expressed on the VLP's outer surface.

The invention also provides in one embodiment a VLP produced by any of the methods disclosed herein The invention additionally provides in one embodiment a method for immunizing an animal against Respiratory Syncytial virus (RSV), comprising a) providing i) a composition comprising a vaccine as disclosed herein, and ii) an animal, and b) administering an immunologically effective amount of the vaccine to the animal to produce an immune response. In one embodiment, the method further comprises detecting the immune response, wherein the immune response comprises antibody that specifically binds to the polypeptide. The data in Example 5 show that anti-F protein antibody responses (i.e., the amount of titer log 10) after VLP immunization were robust and comparable to responses to live virus. The data in Example 5 further show that anti-F protein responses (i.e., the amount of titer log 10) using smaller doses of antigen (10 micrograms) were quite robust. The data in Example 5 show that anti-F protein responses (i.e., the amount of titer log 10) were increasing at time and boost immunization enhanced responses. FIG. 8 shows that anti-F protein antibody responses (i.e., the amount of titer log 10) were increasing at 43 days post immunization. A boost significantly enhanced responses (i.e., the amount of titer log 10). FIG. 9 shows that sera from VLP immunized mice were as effective in virus neutralization as sera from mice infected with live RSV. Example 6 shows that mice immunized with VLP-H/G+F/F and, without a boost, that were challenged with live RSV, were completely protected from RSV replication in lungs. The level of RSV titer log 10 in lung tissue in mice immunized with VLP-H/G+F/F is substantially the same as control mice immunized with "No Ag" (i.e., no antigen) and challenged with live RSV. Example 7 shows that VLP-H/G+F/F immunized mice had reduced levels of inflammation compared to RSV immunized mice. FIG. 12 shows that mice immunized with VLP-H/G+F/HR2F generated anti-F protein antibody titers (using an exemplary ELISA assay) that were substantially the same as those obtained from sera from mice infected with live RSV (at 66 days and even 80 days after immunization). FIG. 13 shows that surprisingly, sera from VLP-H/G+F/HR2F immunized mice were more effective in virus neutralization (using an in vitro assay) than sera from mice infected with live RSV. In a further embodiment, the immune response comprises T lymphocytes that specifically bind to the polypeptide.

The invention also provides in one embodiment a method for detecting the presence of an RSV sequence in a sample, comprising detecting at least one of A) a polypeptide sequence comprising a first polypeptide having at least 95% identity to RSV F protein ectodomain polypeptide SEQ ID NO:16, wherein the first polypeptide comprises at least one of (a) lysine at a position corresponding to amino acid 66 of SEQ ID NO:16, (b) glutamine at a position corresponding to amino acid 101 of SEQ ID NO:16, and (c) valine at a position corresponding to amino acid 203 of SEQ ID NO:16, and B) a nucleotide sequence encoding the polypeptide.

The invention provides in one embodiment a recombinant polypeptide sequence comprising RSV F-LM ectodomain polypeptide SEQ ID NO:16. In one embodiment, the polypeptide sequence is purified. In yet further embodiments, the polypeptide sequence comprises RSV F-LM protein SEQ ID NO:14 or a RSV F-LM protein encoded by the nucleotide sequence SEQ ID NO:15.

The invention also provides in one embodiment a recombinant polypeptide sequence comprising an RSV F protein ectodomain that contains one or more of lysine at a position corresponding to amino acid 66 of SEQ ID NO:16, glutamine at a position corresponding to amino acid 101 of SEQ ID NO:16, and valine at a position corresponding to amino acid 203 of SEQ ID NO:16. In some embodiments, the RSV F ectodomain comprises a conservative amino acid substitution of one or more of the lysine, the glutamine and the valine.

In another embodiment, the invention provides a chimeric polypeptide (including in one embodiment, a purified chimeric polypeptide) comprising the recombinant polypeptide sequences described herein, operably linked to a polypeptide of interest (as well as a vector comprising nucleic acid coding for the chimeric polypeptide). While not intending to limit the type or source of the polypeptide of interest, in one embodiment, the polypeptide of interest is from RSV. Thus, in particular embodiments, the polypeptide of interest comprises one or more RSV protein selected from the group of transmembrane domain, cytoplasmic domain, M protein, N protein, G protein, group A protein, and group B protein, or portion thereof. In other embodiments, the polypeptide of interest comprises an RSV transmembrane domain such as, without limitation, SEQ ID NO:17. In yet further embodiments, the polypeptide of interest comprises an RSV cytoplasmic domain such as, without limitation, SEQ ID NO:18. In other embodiments, the protein of interest is from a source other than RSV.

In yet further embodiments, the polypeptide of interest comprises a protein sequence selected from membrane protein, soluble protein, and epitope. In particular embodiments, the membrane protein is selected from the group of ectodomain of a membrane protein, type 1 protein, ectodomain of a type 1 protein, type 2 protein, ectodomain of a type 2 protein, and type 3 protein. In a preferred embodiment, the polypeptide of interest comprises an epitope.

In some embodiments, the polypeptide of interest comprises a Newcastle Disease Virus (NDV) protein, exemplified by, but not limited to Matrix (M) protein, Fusion (F) protein, Nucleocapsid (NP) protein, and heamagglutinin-neuraminidase (I-IN or G) protein.

The invention also provides in one embodiment a recombinant nucleotide sequence that encodes the polypeptides of described herein. Thus, in one embodiment, the invention provides a nucleotide sequence that comprises SEQ ID NO:20 that encodes RSV F ectodomain polypeptide SEQ ID NO:16. In another embodiment, the invention provides a nucleotide sequence that encodes a polypeptide sequence comprising an RSV F protein ectodomain that contains one or more of lysine at a position corresponding to amino acid 66 of SEQ ID NO:16, glutamine at a position corresponding to amino acid 101 of SEQ ID NO:16, and valine at a position corresponding to amino acid 203 of SEQ ID NO:16.

In particular embodiments, the nucleotide sequence comprises SEQ ID NO:15. In more particular embodiments, the nucleotide sequence comprises a mutation of a poly-adenylation sequence, such as AATAAA of the ectodomain-encoding SEQ ID NO:20, and of the portion of RSV F-LM SEQ ID NO:15, to AATTAA.

Also provided herein in one embodiment is an expression vector comprising one or more of the nucleotide sequences described. The invention additionally provides in one embodiment a cell comprising any of the polypeptide sequences and/or nucleotide sequences described herein. In particular embodiments, the cell expresses the polypeptide sequence on the cell's surface. Exemplary cells include, without limitation, avian cell, insect cell, and mammalian cell.

The invention also provides in one embodiment a virus-like particle (VLP) comprising one or more of the polypeptides described herein. Particularly preferred are chimeric VLPs comprising the chimeric polypeptides described herein. In some embodiments, the VLP is purified. In other embodiments, the VLP is immunogenic. In yet other embodiments, the VLP is comprised in a vaccine. The vaccines may contain at least one adjuvant, at least one diluent and/or at least one excipient.

The invention also provides in one embodiment a method for producing a VLP, comprising (a) providing (i) an expression vector encoding any one or more of the invention's polypeptides, and (ii) a host cell, and (b) transfecting the host cell with the vector to produce a VLP. In some embodiments, the method further comprises c) purifying the VLP. In embodiments where the methods use a chimeric polypeptide that additionally contains a polypeptide of interest, the polypeptide of interest is expressed on the VLP's surface.

In yet another embodiment, the invention provides a method for immunizing an animal, comprising (a) providing (i) any one or more of the vaccines disclosed herein, and (ii) an animal, and (b) administering an immunologically effective amount of the vaccine to the animal to produce an immune response. In particular embodiments, the immune response comprises antibody that specifically binds to the polypeptide of interest. In other embodiments, the immune response comprises T lymphocytes that specifically bind to the polypeptide of interest.

Also provided by the invention in one embodiment is a method for detecting the presence of an RSV sequence in a sample, comprising detecting either or both (a) one or more of invention's polypeptides described herein and (b) one or more of the nucleotide sequences encoding these polypeptide. These methods may be used to distinguish subjects that are immunized with the invention's recombinant vaccines, from individuals infected with wild type RSV.

BRIEF DESCRIPTION OF THE DRAWINGS

FIG. 1A-D: Comparison of the Amino Acid Sequences of RSV F protein from different sources (From NCI data base), including Novavax F (SEQ ID NO:1), RSV F S2 (SEQ ID NO:2), RSV F B unident (SEQ ID NO:3), RSV FB (SEQ ID NO:4), RSV F NP56863 (SEQ ID NO:5), RSV F B1 cp (SEQ ID NO:6), RSV F B1 (SEQ ID NO:7), RSV F A2 cp (SEQ ID NO:8), RSV F A2 (SEQ ID NO:9), RSV F Pringle (SEQ ID NO:10), RSV F 9320 (SEQ ID NO:11), synthetic const (SEQ ID NO:12), synthetic CAA01 (SEQ ID NO:13).

FIG. 2: Amino Acid Sequence of RSV F-LM (SEQ ID NO:14).

FIG. 3: (A) Nucleotide sequence of RSV F-LM (SEQ ID NO:15), including the coding region and the 5' and 3' untranslated region. (B) Nucleotide sequence of RSV F-LM 5' untranslated region (SEQ ID NO:19), RSV F-LM ectodomain (SEQ ID NO:20), RSV F-LM transmembrane (TM) domain (SEQ ID NO:21), RSV F-LM cytoplasmic (CT) domain (SEQ ID NO:22), and RSV F-LM 3' untranslated region (SEQ ID NO:23).

FIG. 5: RSV F-LM Protein sequence of (A) Ectodomain (SEQ ID NO:16), (B) transmembrane (TM) domain (SEQ ID NO:17), and (C) cytoplasmic (CT) domain (SEQ ID NO:18).

FIG. 16: Nucleotide Sequence of F/F chimera #1 (also referred to as F/F chimera) (SEQ ID NO:24). RSV F sequence from base 1 to 1572. NDV F sequence from base 1573 to 1731.

FIG. 17: Nucleotide Sequence of F/HR2F. F/HR2F chimera (also referred to as F/F chimera #2) (SEQ ID NO:25). Underlined sequence is the NDV HR2 domain. RSV sequence is from base 1 to 1536. NDV sequence is from base 1537 to 1797.

FIG. 18(A): Amino acid sequences of the RSV F/NDV F chimera protein, F/F chimera 1 amino acid sequence (SEQ ID NO:26). F/F chimera 2 amino acid sequence (SEQ ID NO:27). RSV sequence from amino acid 1 to 525, NDV sequence from amino acid 526 to 578. FIG. 18(B): Amino acid sequences of the F/HR2F chimera protein, F/HR2F (F/F chimera 2) amino acid sequence. F/F chimera 2: underlined sequence is the NDV HR2 domain. RSV sequence from amino acid 1 to 513, NDV sequence from amino acid 514 to 600.

FIG. 20: (A) Nucleic acid sequence of H/G (SEQ ID NO:28). NDV HN sequences from base 1 to 141, RSV G sequences from base 142 to 845. (B) Amino acid sequence of H/G (a sequence having at least 95% identity to SEQ ID NO:29). NDV HN sequence from amino acid 1 to 48, RSV G sequence from amino acid 49 to 282.

DEFINITIONS

Figure 4:
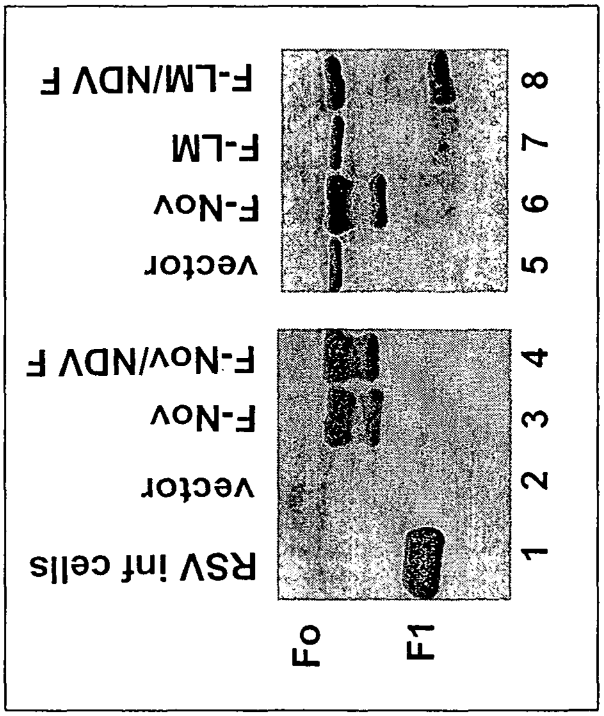
FIG. 4: Expression of different clones of the RSV F protein gene.

To facilitate understanding of the invention, a number of terms are defined below.

The term "corresponding" when in reference to the position of a first amino acid in a first polypeptide sequence as compared to a second amino acid in a second polypeptide sequence means that the positions of the first and second amino acids are aligned when the first and second amino acid sequences are aligned. This is exemplified by the aligned amino acid sequences of FIG. 1. Thus, reference to "glutamine at a position corresponding to amino acid 101 of SEQ ID NO:16," means that when a first amino acid sequence is aligned with SEQ ID NO:16, amino acid position 101 of SEQ ID NO:16 aligns with glutamine in the first amino acid sequence.

The terms "purified" and "isolated" and grammatical equivalents thereof as used herein in reference to a molecule of interest (e.g., polypeptide sequence of interest, nucleic acid sequence of interest, VLP of interest, etc.), refer to the reduction in the amount of at least one undesirable contaminant (such as protein and/or nucleic acid sequence) from a sample containing the molecule of interest. Thus, purification results in "enrichment," i.e., an increase in the amount of polypeptide sequence of interest, nucleic acid sequence of interest and/or VLP of interest, in the sample.

The term "protein of interest" refers to any protein (or portion thereof) that one of ordinary skill in the art may wish to use for any reason (e.g. immunization), including, without limitation, endogenous and heterologous proteins. The terms "endogenous" and "wild type" refer to a sequence that is naturally found in the cell, virus, or virus-like particle into which it is introduced so long as it does not contain some modification relative to the naturally occurring sequence. The term "heterologous" refers to a sequence, which is not endogenous to the cell, virus, or virus-like particle into which it is introduced. For example, heterologous DNA includes a nucleotide sequence, which is ligated to, or is manipulated to become ligated to, a nucleic acid sequence to which it is not ligated in nature, or to which it is ligated at a different location in nature. Heterologous DNA also includes a nucleotide sequence, which is naturally found in the cell or VLP into which it is introduced and which contains some modification relative to the naturally occurring sequence. Generally, although not necessarily, heterologous DNA encodes heterologous RNA and protein of interest that are not normally produced by the cell, virus, or virus-like particle into which it is introduced.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule, which is expressed using a recombinant DNA molecule.

The terms "vector" and "vehicle" are used interchangeably in reference to nucleic acid molecules that transfer DNA segment(s) from one cell to another. The term "expression vector" as used herein refers to a recombinant DNA molecule containing a desired coding sequence and appropriate nucleic acid sequences necessary for the expression (i.e., transcription and/or translation) of the operably linked coding sequence in a particular host organism. Expression vectors are exemplified by, but not limited to, plasmid, phagemid, shuttle vector, cosmid, virus, chromosome, mitochondrial DNA, plastid DNA, and nucleic acid fragments, that may be used for expression of a desired sequence in a cell, such as a human cell, avian cell and/or insect cell. For example, a baculovirus vector may be used to transfect various *Lepidoptera* species. Nucleic acid sequences used for expression in prokaryotes include a promoter, optionally an operator sequence, a ribosome-binding site and possibly other sequences. Eukaryotic cells are known to utilize promoters, enhancers, and termination and polyadenylation signals.

The term "transfect" or "transfecting" as used herein, refers to any mechanism by which a vector may be incorporated into a host cell. A successful transfection results in the capability of the host cell to express any operative genes carried by the vector. Transfections may be stable or transient. One example of a transient transfection comprises vector expression within a cell, wherein the vector is not integrated within the host cell genome. Alternatively, a stable transfection comprises vector expression within a cell, wherein the vector is integrated within the host cell genome.

The term "virus-like particle" as used herein, refers to a non-infective viral subunit either with, or without, viral proteins. For example, a virus-like particle may completely lack the DNA or RNA genome. Further, a virus-like particle comprising viral capsid proteins may undergo spontaneous self-assembly. Preparations of virus-like particles are contemplated in one embodiment, where the preparation is purified free of infectious virions (or at least substantially free, such that the preparation has insufficient numbers to be infectious). Thus, the term "virus-like particle" and "VLP" includes a non-replicating viral shell that resembles live virus in external conformation. In one embodiment, Virus like particles (VLPs) contain proteins that form a virus' outer shell and the surface proteins, without the RNA required for replication. In some embodiments, these proteins are embedded within a lipid bilayer. These particles resemble the virus from which they were derived but lack viral nucleic acid, meaning that they are not infectious. Methods for producing and characterizing recombinantly produced VLPs have been described for VLPs from several viruses, including human papilloma virus type 1 (Hagnesee et al. (1991) J. Virol. 67:315), human papilloma virus type 16 (Kirnbauer et al. Proc. Natl. Acad. Sci. (1992)89:12180), HIV-1 (Haffer et al., (1990) J. Virol. 64:2653), hepatitis A (Winokur (1991) 65:5029), and Newcastle Disease virus (Pantua et al. (2006) J. Virol. 80:11062-11073). Methods for making and purifying RSV VLPs are known in the art (e.g., Morrison et al., U.S. Patent Publication 2007/0178120, Smith et al., WO/2008/061243) and described herein (Example 3)).

The term "F-LM" refers to Respiratory Syncytial Virus Fusion (F) protein that contains alanine$^{102}$, valine$^{379}$, and valine$^{447}$, and is illustrated by SEQ ID NO:14.

The term "Subject" and "animal" interchangeably refer to a multicellular animal (including mammals (e.g., humans, non-Human primates, murines, ovines, bovines, ruminants, lagomorphs, porcines, caprines, equines, canines, felines, ayes, etc.), avians (e.g., chicken), amphibians (e.g. *Xenopus*), reptiles, and insects (e.g. *Drosophila*). "Animal" includes guinea pig, hamster, ferret, chinchilla, mouse and cotton rat.

The terms "operably linked" and "in operable combination" when in reference to the relationship between nucleic acid sequences and/or amino acid sequences refers to linking the sequences such that they perform their intended function. For example, operably linking a promoter sequence to a nucleotide sequence of interest refers to linking them in a manner such that the promoter sequence is capable of directing the transcription of the nucleotide sequence of interest and/or the synthesis of a polypeptide encoded by the nucleotide sequence of interest.

The terms "endogenous" and "wild type" when in reference to a sequence interchangeably refer to a naturally occurring sequence, such as that found in a cell, virus, etc. "Wild type" sequences include sequences that have not been altered by recombinant procedures.

"Alignment" of 2 or more sequences (e.g., DNA, RNA, and/or protein sequences) refers to arranging the 2 or more sequences to identify regions of similarity (e.g., regions of similarity of nucleotides in the DNA and RNA sequences, and regions of similarity of amino acids in the protein sequences).

"Identity" when in reference to 2 or more sequences (e.g., DNA, RNA, and/or protein sequences) refers to the degree of similarity the 2 or more sequences, and is generally expressed as a percentage. Identity in amino acid or nucleotide sequences can be determined using Karlin and Altschul's BLAST algorithm (Proc. Natl. Acad. Sci. USA, 1990, 87, 2264-2268; Karlin, S. & Altschul, SF., Proc. Natl. Acad. Sci. USA, 1993, 90, 5873). Programs called BLASTN and BLASTX have been developed using the BLAST algorithm as a base (Altschul, SF. et al., J. Mol. Biol., 1990, 215, 403). When using BLASTN to analyze nucleotide sequences, the parameters can be set at, for example, score=100 and word length=12. In addition, when using BLASTX to analyze amino acid sequences, the parameters can be set at, for example, score=50 and word length=3. When using BLAST and the Gapped BLAST program, the default parameters for each program are used. Specific techniques for these analysis methods are the well known, e.g., on the website of the National Center for Biotechnology Information Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc. In another example, the term "at least 95%" includes each numerical value (including fractional numbers and whole numbers) from 95% to 100%, including, for example, 95%, 96%, 97%, 98%, 99% and 100%.

"Respiratory Syncytial Virus" and "RSV" refer to a negative-sense, single-stranded RNA virus of the family Paramyxoviridae that causes a respiratory disease, especially in children. RSV is a member of the paramyxovirus subfamily Pneumovirinae. Its name comes from the fact that F proteins on the surface of the virus cause the cell membranes on nearby cells to merge, forming syncytia.

"Newcastle Disease Virus" and "NDV" refer to a negative-sense single-stranded RNA virus of the family Paramyxoviridae that causes a highly contagious zoonotic bird disease affecting many domestic and wild avian species.

"ND VLP" and "Newcastle Disease virus like particle" interchangeably refer to a virus like particle containing at least one Newcastle Disease Virus protein, preferably, at least NDV matrix protein.

"Efficiency" of release of an organism (e.g., virus and/or virus like particle) refers to the ratio of the organism that is released extracellularly from a cell relative to the total amount of intracellular organism and extracellular organism. Efficiency is usually expressed as a percentage. Efficiency of release of VLPs may be determined using methods known in the art and disclosed herein.

The terms "matrix protein", "membrane protein", and "M protein" as used herein interchangeably mean any protein localized between the envelope and the nucleocapsid core and facilitates the organization and maintenance of the virion structure and budding processes.

The term "fusion protein" or "F protein" as used herein, means any protein that projects from the envelope surface and mediates host cell entry by inducing fusion between the viral envelope and the cell membrane. However, it is not intended that the present invention be limited to functional F proteins. For example, an F protein may be encoded by a mutant F gene such as, but not limited to, Newcastle Disease virus (NDV) F-K115Q. F-K115Q is believed to eliminate the normal cleavage and subsequent activation of the fusion protein. F-K115Q mimics naturally occurring F-protein mutations in avirulent NDV strains, and in cell culture, eliminates any potential side effects of cell-cell fusion on the release of VLPs. Exemplary NDV F protein sequences include those in FIG. 10 of WO 2009/105152, comprising ATCC M21881, and ATCC AAG36978, and the following ATCC Accession numbers: AAA46642 (strain Texas GB), CAA00288 (strain Chambers), ABO65262 (strain JL01), AAS00690 (strain F48E9), AAA46642 (strain Texas GB), CAF32456 (strain La Sota), AAC62244 (strain DB5), AAC62243 (strain DB3), AAC28467 (strain F48E9), ABY41269 (strain D58), ABV60351 (strain SNV-5074), AAL18935 (strain ZJ1), and AAY43057 (strain FM1/03).

The term "nucleocapsid protein" or "NP protein" as used herein, means any protein that associates with genomic RNA (i.e., for example, one molecule per hexamer) and protects the RNA from nuclease digestion. Exemplary NP protein sequences from NDV include those in WO 2009/105152, such as the sequences of FIG. 8 of WO 2009/105152 (ATCC No. AB124608), FIG. 24 of WO 2009/105152 (ATCC No. AF060483), and the following ATCC Accession Nos. PO9459 (strain Beaudette C), Q99FY3 (strain AF2240), NP_071466 (strain B1), ABG35929 (strain chicken/China/Guangxi1/2000), AA276405 (strain PNY-LMV42), CAB51322 (strain clone 30), ABO32476 (strain F), AAW30676 (strain LaSota), AAO4779 (strainV4), BAD16677 (strainAPMV1/Quail/Japan/Chiba/2001), and BAD16672 (strain APMV1/chicken/Japan/Niiga/89).

The term "haemagglutinin-neuraminidase protein", "HN protein", or "G protein" as used herein, means any protein that spans the viral envelope and projects from the surface as spikes to facilitate cell attachment and entry (i.e., for example, by binding to sialic acid on a cell surface). These proteins possess both haemagglutination and neuraminidase activity. Exemplary NDV HN protein sequences include those in WO 2009/105152, such as those in FIG. 9, FIG. 20, and FIG. 21 of WO 2009/105152, and the following ATCC Accession Numbers: CAB69409 (strain Texas GB), CAA00289 (strain Chambers), ABW34443 (strain JS-1/06/wd), ABW89770 (strain B1), CAA77272 (strain LaSota type), CAF32450 (strain LaSota), ABI16058 (strain PB9601), ABG35963 (strain Chicken/China/Guangxi5/2000), U371189 (strain clone 30), U371190 (strain vineland), U371191 (strain VGGA), and U371193 (strain B1(SEDRL)).

"RSV F/F" refers to a chimeric polypeptide containing Respiratory Syncytial Virus F-LM protein ectodomain operably linked to Newcastle Disease Virus Fusion (F) protein cytoplasmic domain and transmembrane domain (Examples 4-7 and 10). RSV F/F sequence is exemplified by chimera #1 SEQ ID NO:26 of FIG. 18(A), encoded by the DNA SEQ ID NO:24 of FIG. 16.

"RSV H/G" and "RSV H/Ga" interchangeably refer to a chimeric polypeptide containing Respiratory Syncytial Virus G protein ectodomain operably linked to Newcastle Disease Virus HN protein cytoplasmic domain and transmembrane domain (Example 4). RSV H/G sequence is exemplified by the amino acid sequence SEQ ID NO:29 of FIG. 20(B), which is encoded by the DNA sequence SEQ ID NO:28 of FIG. 20(A).

"RSV F/HR2F" refers to a chimeric polypeptide containing Respiratory Syncytial Virus F-LM protein ectodomain operably linked to Newcastle Disease Virus HR2 portion of the F protein ectodomain, the NDV TM domain, and the NDV CT domain (Example 8). RSV F/HR2F sequence is exemplified by the amino acid sequence SEQ ID NO:27 of FIG. 18(B), which is encoded by the DNA sequence SEQ ID NO:25 of FIG. 17.

"VLP-H/G+F/F" refers to a virus-like particle containing RSV H/G and RSV F/F (Examples 5-7 and 10).

"VLP-H/G+F/HR2F" refers to a virus-like particle containing RSV H/G and RSV F/HR2F (Example 8).

The term "ectodomain" when in reference to a membrane protein refers to a protein sequence, and portions thereof, that is exposed on the extracellular side of a lipid bilayer of a cell, virus and the like. Methods for determining the ectodomain of a protein are known in the art (Singer (1990); High et al. (1993), and McVector software, Oxford Molecular).

The terms "cytoplasmic domain," "cytoplasmic tail," and "CT" are used interchangeably to refer to a protein sequence, and portions thereof, that is on the cytoplasmic side of the lipid bilayer of a cell, virus and the like. Methods for determining the CT of a protein are known in the art (Elofsson et al. (2007) and Bernsel et al. (2005)).

The terms "transmembrane domain" and "TM" are used interchangeably to refer to a protein sequence, and portions thereof, that spans the lipid bilayer of a cell, virus and the like. Methods for determining the TM of a protein are known in the art (Elofsson et al. (2007) Annu. Rev. Biochem. 76:125-140; Bernsel et al. (2005) Protein Science 14:1723-1728).

DESCRIPTION OF THE INVENTION

The invention provides, in one embodiment, RSV fusion (F) protein ectodomain polypeptide sequences and nucleotide sequences encoding them, as well as cells containing the invention's polypeptide and nucleotide sequences. The invention further provides in one embodiment VLPs that contain the invention's polypeptides, and methods for using the VLPs for protein expression and vaccine formulation. Also provided in one embodiment are methods for distinguishing between subjects immunized with the invention's compositions and subjects infected with RSV. The invention is further described under (A) RSV Polypeptide Sequences, (B) Nucleotide Sequences, Expression Vectors, and Cells, and (C) Virus-Like Particles (VLPs).

A. RSV Polypeptide Sequences

Respiratory Syncytial Virus (RSV) is a paramyxovirus, in the pneumovirus subfamily. The virus encodes 10 proteins. The virion contains two glycoproteins important for the entry of the virus into cells: the glycoprotein G is classified as an attachment protein and the fusion or F protein mediates the fusion of the viral membrane with the cell membrane, an essential step to begin the infectious cycle of the virus. Paramyxovirus F proteins are synthesized as a precursor, Fo. This precursor must be cleaved into F1 and F2 to activate the fusion activity of the virus. The RSV F protein is unique among paramyxoviruses in that two cleavages within the F2 region of the molecule are required. Thus three forms of the F protein can be detected in infected cells, the uncleaved Fo, the F protein with one cleavage and the F protein with both cleavages. These cleavages occur in the Golgi membranes of the infected cell and are mediated by host cell proteases.

The invention provides recombinant polypeptide sequences that may be used for expression of RSV VLPs. RSV VLPs are useful for protein expression, and particularly for expression of antigenic proteins that may be used in vaccines. In one embodiment, the invention provides recombinant polypeptide sequences comprising RSV F-LM ectodomain polypeptide SEQ ID NO:16. SEQ ID NO:16 is distinguished from Novavax RSV F protein ectodomain in F-Nov by having alanine instead of proline at amino acid 102, having valine instead of isoleucine at amino acid 379, and having valine instead of methionine at amino acid 447. The invention is premised, in part, on data herein that shows enhanced protein expression when using the invention's sequences as compared to prior art RSV F protein sequences. In particular, in contrast to prior art sequences, the invention's sequences resulted in expression of F1, the fully cleaved form of the F protein (Examples 1 and 2). Thus, a codon optimized RSV F protein sequence from Novavax Company (termed F-Nov) showed very low levels of expression on eukaryotic cells (Example 1). An analysis of all RSV F sequences in the data base indicated that the codon optimized cDNA encoded a protein with three amino acid changes in the protein sequence that were not present in any of the other published F protein sequences (shown in FIG. 1). These changes were at amino acid residues 102, 379, and 447. Comparisons of over 10 published sequences indicated that there was significant variation between all sequences in other positions as well (FIG. 1). Analysis of the nucleotide sequences of the published F protein genes showed a great deal of variation. In contrast, the invention's sequences showed enhanced expression on the surface of eukaryotic cells, including in the presence of chimeric proteins from sources other than RSV (e.g., from New Castle Disease Virus, NDV).

In a further embodiment, the invention also provides recombinant polypeptide sequences comprising an RSV F protein ectodomain that contains one or more of lysine at a position corresponding to amino acid 66 of SEQ ID NO:16, glutamine at a position corresponding to amino acid 101 of SEQ ID NO:16, and valine at a position corresponding to amino acid 203 of SEQ ID NO:16. This invention is premised, in part on the discovery that RSV F-LM ectodomains that resulted in enhanced protein and VLP expression were distinguished from all known RSV F protein ectodomains by containing lysine[66] instead of glutamic acid[66], glutamine[101] instead of proline[101], and valine[203] instead of leucine[203].

In one embodiment, the invention's RSV F ectodomain comprises a conservative amino acid substitution of one or more of the lysine, the glutamine and the valine that correspond to lysine[66] of SEQ ID NO:16, glutamine[101] of SEQ ID NO:16, and valine[203] of SEQ ID NO:16. A "conservative substitution" of an amino acid refers to the replacement of that amino acid with another amino acid that has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains that may be conservatively substituted one for the other include phenylalanine, tyrosine, and tryptophan. Cysteine and methionine are sulphur-containing amino acids that may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. "Non-conservative substitution" is a substitution other than a conservative substitution.

In a further embodiment the invention provides a chimeric polypeptide comprising one or more of the invention's RSV sequences operably linked to one or more polypeptide of interest. A "chimeric" polypeptide refers to a polypeptide that contains at least two amino acid sequences that are covalently linked together. The two amino acid sequences may be derived from different sources (e.g., different organisms, different tissues, different cells, etc.) or may be different sequences from the same source. In one embodiment, the chimeric polypeptide is a fusion polypeptide wherein at least two different amino acid sequences are recombinantly expressed together.

In one embodiment, the chimeric polypeptide may contain the invention's RSV polypeptide sequence operably linked to one or more additional sequences from RSV, such as RSV transmembrane (TM) domain, RSV cytoplasmic (CT) domain, RSV M protein, RSV N protein, RSV G protein, RSV group A protein, and RSV group B protein. RSV transmembrane (TM) domains are exemplified by the RSV TM domains in FIG. 1 from RSV F Novavax, RSV F S2, RSV F B unident, RSV FB, RSV F (NP56863), RSV F B1 cp, RSV F B1, RSV F A2 cp, RSV F A2, RSV F Pringle, RSV F 9320, synthetic construct, synthetic CAA01, and SEQ ID NO:17. RSV cytoplasmic (CT) domain, as exemplified by the RSV CT domains in FIG. 1 from RSV F Novavax, RSV F S2, RSV F B unident, RSV FB, RSV F (NP56863), RSV F B1 cp, RSV F B1, RSV F A2 cp, RSV F A2, RSV F Pringle, RSV F 9320, synthetic construct, synthetic CAA01, and SEQ ID NO:18. RSV M protein, RSV N protein, RSV G protein, RSV group A protein, and RSV group B protein are exemplified by those described in Smith et al., WO/2008/061243.

In another embodiment, the chimeric polypeptide may contain the invention's RSV polypeptide sequence operably linked to one or more polypeptide of interest that is from a source other than RSV.

Examples of proteins of interest include proteins, and portions thereof, that are expressed as glycoproteins, membrane proteins and portions thereof, soluble proteins and portions thereof, epitopes and portions thereof, and the like. Where it is desirable to simultaneously express more than one protein of interest, the invention contemplates that the simultaneously expressed proteins may be of the same type (e.g., type 1 protein, type 2 protein, type 3 protein, soluble protein, epitope). Alternatively, the simultaneously expressed proteins may be of different types (for example, type 1 protein combined with type 2 protein, type 1 protein combined with type 3 protein, etc.). Simultaneously expressed proteins may be encoded by nucleotide sequences that are on the same, or different, vectors.

In one embodiment, the protein of interest comprises a membrane protein. A "membrane protein" refers to a protein that is at least partially embedded in the lipid bilayer of a cell, virus and the like. Membrane proteins include type 1 proteins, type 2 proteins, and type 3 proteins. Methods for determining the type of membrane protein are known (for example, Singer (1990) Ann. Rev. Cell Biol. 6:247-296 and High et al. (1993) J. Cell Biol. 121:743-750), including commercially available software, such as McVector software, Oxford Molecular.

In another embodiment, the protein of interest comprises an ectodomain of a membrane protein. The term "ectodomain" when in reference to a membrane protein refers to the portion of the protein that is exposed on the cytoplasmic side of a lipid bilayer of a cell, virus and the like. Methods for determining the ectodomain of a protein are known in the art (Singer (1990); High et al. (1993), and McVector software, Oxford Molecular). Exemplary ectodomains include, but are not limited to those described in U.S. Pat. Nos. 7,262,270; 7,253,254; 7,250,171; 7,223,390; 7,189,403; 7,122,347; 7,119,165; 7,101,556; 7,067,110; 7,060,276; 7,029,685; 7,022,324; 6,946,543; 6,939,952; 6,713,066; 6,699,476; 6,689,367; 6,566,074; 6,531,295; 6,417,341; 6,248,327; 6,140,059; 5,851,993; 5,847,096; 5,837,816; 5,674,753; and 5,344,760. Additional examples of ectodomains include ectodomains of membrane type 1 proteins, type 2 proteins, and type 3 proteins, as further described below.

In one embodiment, the protein of interest comprises a type 1 protein. The term "type 1 protein" refers to a membrane protein that contains one transmembrane domain (TM) sequence, which is embedded in the lipid bilayer of a cell, virus and the like. The portion of the protein on the $NH_2$-terminal side of the TM domain is exposed on the exterior side of the membrane, and the COOH-terminal portion is exposed on the cytoplasmic side. Exemplary type 1 proteins include, without limitation, Fujian Strain of Influenza HA, Canine Distemper Virus Fusion Protein, Cytomegalovirus (CMV) gH glycoprotein, Cytomegalovirus gH Glycoprotein, Ebola virus Glycoprotein precursor, Human Immunodeficiency Virus (HIV) envelope protein, Herpes Simplex virus (HSV) gH glycoprotein, Herpes Simplex virus (HSV) gL Glycoprotein, Influenza virus HA-type H1, Influenza virus HA from influenza B Malaysia, Influenza virus HA representative H1, Influenza virus HA, representative H3, Influenza virus HA representative H5 HA, Influenza virus HA representative H7 HA, Influenza virus HA representative H9 HA, Nipah virus F protein, SARS virus surface spike glycoprotein, Varicella Zoster Virus gB glycoprotein, Varicella Zoster Virus gE glycoprotein, and Varicella Zoster Virus gI glycoprotein.

In another embodiment, the protein of interest comprises an ectodomain of a type 1 protein. The term "ectodomain" of a type 1 protein refers to at least a portion of the type 1 protein on the $NH_2$-terminal side of the TM domain that is exposed on the exterior side of the membrane. Exemplary type 1 protein ectodomains include, without limitation, Influenza Virus Fujian strain HA protein, CMV gB protein, CMV gH protein, Ebola G protein, Influenza virus HA H1 protein, Influenza virus B HA protein, Influenza virus H3 HA protein, HIV envelope protein, HSV gH protein, Influenza virus H7 HA protein, Influenza virus H9 protein, Influenza Virus H5 protein, Nipah virus F protein, SARS virus S glycoprotein, Varicella Zoster Virus gB protein, Varicella Zoster Virus gE protein, and Varicella Zoster Virus gI protein.

In a further embodiment, the protein of interest comprises a type 2 protein. The term "type 2 protein" refers to a membrane protein that contains one transmembrane domain (TM) sequence, which is embedded in the lipid bilayer of a cell, virus and the like. In contrast to type 1 proteins, in type 2 proteins the portion of the protein on the $NH_2$-terminal side of the TM domain is exposed on the cytoplasmic side of the membrane, and the COOH-terminal portion is exposed on the exterior side. Exemplary type 2 proteins include, without limitation, Fujian Influenza NA, Canine Distemper Virus H Glycoprotein, Avian Metapneumovirus G Protein, Human Metapneumovirus G Glycoprotein, Human Respiratory Syncytial Virus G Glycoprotein, Influenza Virus B NA Glycoprotein, Influenza Virus N1 NA from H5N1 Virus, Influenza Virus NA N2, Influenza Virus NA N3 type, Measles Virus HA Protein, Mumps Virus HN, Nipah Virus G Protein, Parainfluenza Virus Type 2 HN Protein, Parainfluenza Virus 3 HN Glycoprotein, Respiratory Syncytial Virus G Protein, and Vaccinia Virus Surface Antigen.

In a particular embodiment, the protein of interest comprises an ectodomain of a type 2 protein. The term "ectodomain" of a type 2 protein refers to at least a portion of the type 2 protein on the COOH-terminal side of the TM domain that is exposed on the exterior side of the membrane. Examples of type 2 protein ectodomains include, without limitation, Influenza Virus Fujian strain NA protein, Metapneumovirus G protein, Influenza Virus B NA protein, Human Metapneumovirus G protein, Human respiratory Syncytial virus G protein, Influenza virus N1 NA protein, Influenza virus N3 NA protein, Influenza virus N2 NA protein, Measles virus HA protein, Mumps virus HN protein, Nipah virus G protein, Parainfluenza 2 virus HN protein, Parainfluenza virus 3 HN protein, and Vaccinia virus surface protein.

In yet another embodiment, the protein of interest comprises a type 3 protein. the term "type 3 protein" refers to a membrane protein that contains more than one transmembrane domain (TM) sequence containing hydrophobic amino acids, which are embedded in the lipid bilayer of a cell, virus and the like. The portion of the protein on the $NH_2$-terminal side of the TM domain may be exposed on either the cytoplasmic side or the exterior side of the membrane. Conversely, the portion of the protein on the COOH-terminal side of the TM domain may be exposed on either the cytoplasmic side or the exterior side of the membrane. Exemplary type 3 proteins include, without limitation, Epstein Barr Virus (EBV) LMP2A protein, Glut 1 HTLV receptor protein, Glutamate Receptor protein, Hepatitis B virus L form of S glycoprotein, Prion Protein, and Presenilin (human) protein.

In a particular embodiment, the protein of interest comprises an ectodomain of a type 3 protein. The term "ectodomain" of a type 3 protein refers to at least a portion of the type 3 protein of either the $NH_2$-terminal or the COOH-terminal side of the TM domain that is exposed on the exterior side of the membrane. Some examples of type 3 protein ectodomains include, without limitation, Prion protein, Prion protein, Glut-1 protein, Glut-1 protein, Glut-1 protein, LMP2A protein, LMP2A protein, Presenilin protein, and Hepatitis B virus L form of HBsAg protein.

In one embodiment, the protein of interest comprises a soluble protein. The term "soluble protein" refers to a protein that is not embedded in the lipid bilayer of a cell, virus and the like. Examples of soluble proteins include, without limitation, Hepatitis A Virus VP1, Human Parvovirus VP (B19 Virus), Norovirus VP1, Human Rhinovirus VP1, and Human Rotavirus (strain K8) VP4.

In one embodiment, the protein of interest comprises an antigen. The terms "antigen," "immunogen," "antigenic," "immunogenic," "antigenically active," and "immunologically active" when made in reference to a molecule, refer to any substance that is capable of inducing a specific humoral and/or cell-mediated immune response.

In one embodiment, the antigen comprises an epitope. The terms "epitope" and "antigenic determinant" refer to a structure on an antigen. While not intending to limit the invention in any way to a particular mechanism, it is believed that such a structure interacts with the binding site of an antibody or T cell receptor as a result of molecular complementarity. An epitope may compete with the intact antigen, from which it is derived, for binding to an antibody. Generally, secreted antibodies and their corresponding membrane-bound forms are capable of recognizing a wide variety of substances as antigens, whereas T cell receptors are capable of recognizing only fragments of proteins which are complexed with MHC molecules on cell surfaces. Antigens recognized by immunoglobulin receptors on B cells are subdivided into three categories: T-cell dependent antigens, type 1 T cell-independent antigens; and type 2 T cell-independent antigens. Also, for example, when a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

Exemplary epitopes include, without limitation, EphrinA2 epitopes from renal cell carcinoma and prostate cancer (U.S. Pat. No. 7,297,337), hepatitis C virus epitopes (U.S. Pat. Nos. 7,238,356 and 7,220,420), vaccinia virus epitopes (U.S. Pat. No. 7,217,526), dog dander epitopes (U.S. Pat. No. 7,166,291), human papilloma virus (HPV) epitopes (U.S. Pat. Nos. 7,153,659 and 6,900,035), *Mycobacterium tuberculosis* epitopes (U.S. Pat. Nos. 7,037,510 and 6,991,797), bacterial meningitis epitopes (U.S. Pat. No. 7,018,637), malaria epitopes (U.S. Pat. No. 6,942,866), and type 1 diabetes mellitus epitopes (U.S. Pat. No. 6,930,181).

In a particular embodiment, the polypeptide of interest comprises a Newcastle Disease Virus (NDV) protein, as exemplified by, but not limited to, NDV Matrix (M) protein, NDV Fusion (F) protein, NDV Nucleocapsid (NP) protein, and NDV heamagglutinin-neuraminidase (RN or G) protein. For example, FIG. 4 shows enhanced expression when using chimeras containing the ectodomain of F-LM and NDV F.

Exemplary NP protein sequences from NDV include those obtainable from GenBank (AF309418, AB124608 and AF060483), ATCC No. AB124608, ATCC No. AF060483, and the following ATCC Accession Nos. PO9459 (strain Beaudette C), Q99FY3 (strain AF2240), NP_071466 (strain B1), ABG35929 (strain chicken/China/Guangxi1/2000), AA276405 (strain PNY-LMV42), CAB51322 (strain clone 30), ABO32476 (strain F), AAW30676 (strain LaSota), AAO4779 (strainV4), BAD16677 (strainAPMV1/Quail/Japan/Chiba/2001), and BAD16672 (strain APMV1/chicken/Japan/Niiga/89).

Exemplary NDV F protein sequences include those obtainable from GenBank (AF309418, Y18728, M21881, AAG36978) and the following ATCC Accession numbers: M21881, AAG36978, AAA46642 (strain Texas GB), CAA00288 (strain Chambers), ABO65262 (strain JL01), AAS00690 (strain F48E9), AAA46642 (strain Texas GB), CAF32456 (strain La Sota), AAC62244 (strain DB5), AAC62243 (strain DB3), AAC28467 (strain F48E9), ABY41269 (strain D58), ABV60351 (strain SNV-5074), AAL18935 (strain ZJ1), and AAY43057 (strain FM1/03).

Exemplary NDV HN protein sequences include those obtainable from GenBank (AF309418, AY288990, M22110, U37193), and the following ATCC Accession Numbers: CAB69409 (strain Texas GB), CAA00289 (strain Chambers), ABW34443 (strain JS-1/06/wd), ABW89770 (strain B1), CAA77272 (strain LaSota type), CAF32450 (strain LaSota), AB116058 (strain PB9601), ABG35963 (strain Chicken/China/Guangxi5/2000), U371189 (strain clone 30), U371190 (strain vineland), U371191 (strain VGGA), and U371193 (strain B1(SEDRL)).

Exemplary NDV M protein sequences include those obtainable from GenBank AF309418, AY728363, M16622, U25828, AY728363, M16622, U25828, AF431744, NC_002617, AY562986, AY562989, AY562988, AY562990, AY845400, AJ880277, EU293914, AF431744, and AY562991.

B. Nucleotide Sequences, Expression Vectors, and Cells

The invention also provides in one embodiment nucleotide sequences encoding the invention's polypeptide sequences. In one embodiment, the nucleotide sequence is a recombinant nucleotide sequence comprising SEQ ID NO:20 (FIG. 3B) that encodes RSV ectodomain. The invention's RSV F-LM sequences were derived by RT-PCR of RSV virion RNA obtained by extraction of the RNA from purified virus.

The invention's nucleotide sequences are used in one embodiment for expression of RSV VLPs that are useful for protein expression, and particularly for expression of antigenic proteins that may be used in vaccines. Exemplary nucleotide sequences that encode the invention's RSV ectodomain include the DNA sequence of F-LM (SEQ ID NO:15). In one embodiment, nucleotide sequence contains a mutation of the poly-adenylation sequence AATAAA to AATTAA. This mutation eliminates the poly-A addition signal and increases the levels of mRNA.

The invention's nucleotide sequences in one embodiment may be expressed using any expression vector, particularly baculovirus vectors, using methods known in the art (e.g., Smith et al., WO/2008/061243) and methods described herein (Example 3).

The invention also provides in one embodiment a "host cell" comprising any of the vectors disclosed herein. In one embodiment, the cell is selected from avian cell, insect cell, and mammalian cell. In one embodiment, the cells are in vitro.

In another embodiment, the avian cell is an ELL-0 cell (East Lansing Strain of Chicken embryo fibroblast) or an egg cell. In a further embodiment, the insect cell is selected from the group exemplified by *Trichoplusia ni* (Tn5) cell and SF9 cell. In a further embodiment, the mammalian cell is selected from the group exemplified by Chinese hamster ovary CHO-K1 cells, bovine mammary epithelial cells, monkey COS-7 cells, human embryonic kidney 293 cells, baby hamster kidney (BHK) cells, mouse sertoli TM4 cells, monkey kidney CV1 cells, African green monkey kidney VERO-76 cells, human cervical carcinoma HELA cells, canine kidney MDCK cells, buffalo rat liver BRL 3A cells, human lung W138 cells, human liver Hep G2 cells, mouse mammary tumor (MMT) cells, TRI cells, MRC 5 cells, FS4 cells, rat fibroblasts 208F cells, an bovine kidney MDBK cells. The cell may be in vitro or in vivo.

In particular embodiments, the cell expresses the invention's polypeptide sequences on the cell's surface. Data herein shows (Examples 1 and 2) that the invention's sequences, in contrast to prior art sequences, are expressed on the surface of exemplary avian cells and COS-7 cells.

C. Virus-Like Particles (VLPs)

The invention also provides in one embodiment RSV virus-like particles (VLPs) comprising any one or more of the polypeptides of the invention. Methods for making and purifying RSV VLPs are known in the art (e.g., Morrison et al., U.S. Patent Publication 2007/0178120, Smith et al., WO/2008/061243) and described herein (Example 3).

In one embodiment, the virus-like particle (VLP) is purified. In another embodiment, the invention's VLPs express the protein of interest on the outside surface of the virus-like particle (VLP), thereby making the protein available for eliciting an immune response upon introduction of the VLP into a host.

Methods for determining that proteins are expressed on the outer surface of a VLP are known in the art for biotinylation of cell surface proteins that are expressed by cells that harbor constructs for VLP expression (Morrison et al., U.S. Patent Publication 2007/0178120; McGinnes et al. (2006) J. Virol. 80:2894-2903). In addition, expression of the protein of interest on the outer surface of VLPs may also be determined by using the VLPs to produce antibodies, such as in an animal, egg cell, or tissue culture. The production of an antibody that specifically binds to the protein of interest indicates that the protein of interest is expressed on the outside surface of the VLP.

In one embodiment, the virus-like particles (VLPs) of the invention are comprised in a vaccine. The term "vaccine" refers to a preparation that may be administered to a host to induce a cellular and/or antibody immune response. Vaccines may contain adjuvants, pharmaceutically acceptable carriers, diluents or excipients.

In one embodiment, the efficiency of producing the invention's virus-like particles (VLPs) is at least 2 fold greater, at least 5 fold greater, at least 10 fold greater, at least 20 fold greater, and/or at least 30 fold greater when using the invention's sequences compared to corresponding prior art sequences (Example 2). The term "efficiency" when in reference to production of VLPs by a cell refers to the number of VLPs produced by a cell, such as following expression of an expression vector by those cells. The number of VLPs may be determined directly or indirectly by, for example, quantifying the amount of protein expressed in the VLPs, such as RSV ectodomain protein, The dosage of the vaccine can be determined by, for example, first identifying doses effective to elicit a prophylactic and/or therapeutic immune response. This may be accomplished by measuring the serum titer of virus specific immunoglobulins and/or by measuring the inhibitory ratio of antibodies in serum samples, urine samples, and/or mucosal secretions. The dosages can be determined from animal studies, including animals that are not natural hosts to RSV. For example, the animals can be dosed with a vaccine candidate, e.g. VLPs of the invention, to partially characterize the immune response induced, and/or to determine if any neutralizing antibodies have been produced. In addition, routine human clinical studies can be performed to determine the effective dose for humans. Effective doses may be extrapolated from dose-response curves derived from in vitro and/or in vivo animal models.

Vaccines may in one embodiment contain an adjuvant. The term "adjuvant" as used herein refers to any compound which, when injected together with an antigen, non-specifically enhances the immune response to that antigen. Exemplary adjuvants include Complete Freund's Adjuvant, Incomplete Freund's Adjuvant, Gerbu adjuvant (GMDP; C.C. Biotech Corp.), RIBI fowl adjuvant (MPL; RIBI Immunochemical Research, Inc.), potassium alum, aluminum phosphate, aluminum hydroxide, QS21 (Cambridge Biotech), Titer Max adjuvant (CytRx), and Quil A adjuvant. Other compounds that may have adjuvant properties include binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

Vaccines may in one embodiment be formulated using a diluent. Exemplary "diluents" include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose. Exemplary "carriers" include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

Vaccines may in one embodiment contain an excipient. The term "excipient" refers herein to any inert substance (e.g., gum arabic, syrup, lanolin, starch, etc.) that forms a vehicle for delivery of an antigen. The term excipient includes substances that, in the presence of sufficient liquid, impart to a composition the adhesive quality needed for the preparation of pills or tablets.

In one embodiment, the virus-like particle (VLP) is immunogenic. The term "immunogenic" refers to a molecule that is capable of eliciting an immune response in a host animal, including producing an antibody response and/or a cell mediated immune response (for example, involving cytotoxic T lymphocytes (CTL)).

In one embodiment, the immune response comprises production of an antibody that specifically binds to the protein of interest that is expressed on the VLP. The terms "specific binding" or "specifically binding" when used in reference to the interaction of an antibody or cell (such as a lymphocyte cell) with another molecule (such as a protein or peptide), means that the interaction is dependent upon the presence of a particular structure (i.e., the antigenic determinant or epitope) on the molecule. For example, if an antibody is specific for epitope "A," the presence of a protein containing epitope A (or free, unlabelled A) in a reaction containing labeled "A" and the antibody will reduce the amount of labeled A that is bound to the antibody. Similarly, if a lymphocyte cell is specific for epitope "A," the presence of a protein containing epitope A (or free, unlabelled A) in a reaction containing labeled "A" and the lymphocyte cell will reduce the amount of labeled A that is bound to the lymphocyte cell.

In another embodiment, the immune response comprises increasing the number of T lymphocytes that specifically bind to the protein of interest. The term "T lymphocytes" includes, but is not limited to, one or more of cytotoxic T cells (CTLs), helper T cells, and suppressor T cells. T lymphocytes express receptors that recognize antigen in the form of peptide fragments complexed with MHC molecules.

The terms "increase," "elevate," "raise," and grammatical equivalents (including "higher," "greater," etc.) when in reference to the level of any molecule (e.g., VLP, amino acid sequence, nucleic acid sequence, etc.) and/or phenomenon (e.g., immune response, binding to a molecule, efficiency of expression of a nucleic acid sequence, efficiency of release of VLP from a cell, etc.) in a first sample relative to a second sample, mean that the quantity of the molecule and/or phenomenon in the first sample is higher than in the second sample by any amount that is statistically significant using any art-accepted statistical method of analysis. In one embodiment, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

The terms "reduce," "inhibit," "diminish," "suppress," "decrease," and grammatical equivalents (including "lower," "smaller," etc.) when in reference to the level of any molecule (e.g., VLP, amino acid sequence, nucleic acid sequence, etc.) and/or phenomenon (e.g., immune response, binding to a molecule, efficiency of expression of a nucleic acid sequence, efficiency of release of VLP from a cell, etc.) in a first sample relative to a second sample, mean that the quantity of molecule and/or phenomenon in the first sample is lower than in the second sample by any amount that is statistically significant using any art-accepted statistical method of analysis. In one embodiment, the quantity of the molecule and/or phenomenon in the first sample is at least 10% lower than, at least 25% lower than, at least 50% lower than, at least 75% lower than, and/or at least 90% lower than the quantity of the same molecule and/or phenomenon in a second sample.

Thus, the invention's VLPs may in one embodiment be incorporated into vaccines, and an immunologically effective amount of the vaccine may be administered to an animal to produce an immune response. As used herein the terms "immunogenically effective amount" and "immunologically effective amount" refer to that amount of a molecule that elicits and/or increases production of an immune response (including production of specific antibodies and/or induction of a TCL response) in a host upon vaccination. It is preferred, though not required, that the immunologically-effective (i.e., immunogenically-effective) amount is a "protective" amount. The terms "protective" and "therapeutic" amount of a composition refer to an amount of the composition that delays, reduces, palliates, ameliorates, stabilizes, and/or reverses one or more symptoms of a disease.

The invention's VLPs and vaccines may be in one embodiment administered prophylactically (i.e., before infection with an infectious agent and/or the observation of disease symptoms) and/or therapeutically (i.e., after infection with an infectious agent and/or the observation of disease symptoms). Administration also may be concomitant with (i.e., at the same time as, or during) manifestation of one or more disease symptoms. Also, the invention's VLPs and vaccines may be administered before, concomitantly with, and/or after administration of another type of drug or therapeutic procedure (e.g., surgery, chemotherapy, radiotherapy, etc.). Methods of administering the invention's compounds include, without limitation, administration in parenteral, oral, intraperitoneal, intranasal, topical (e.g., rectal, and vaginal), and sublingual forms. Parenteral routes of administration include, for example, subcutaneous, intravenous, intramuscular, intrasternal injection, and infusion routes.

The invention also provides in one embodiment methods for distinguishing between an animal that has been immunized with the invention's RSV sequences and an animal that has been infected by RSV. These methods may be based on detecting the invention's polypeptides and/or nucleotide sequences encoding the invention's polypeptides

EXPERIMENTAL

The following examples serve to illustrate certain preferred embodiments and aspects of the present invention and are not to be construed as limiting the scope thereof.

Cell lines were obtained from American Type Culture Collection. Antibodies for detection of RSV F were obtained from several companies (Covalab, Chemicon, Abcam, Biodesign). RSV was obtained from Dr. R. Finberg (Dept of Medicine). Using this virus we prepared our own stocks of the RSV virus.

Example 1

RSV F-Nov Protein is not Expressed on the Cell Surface of Eukaryotic Cells

A codon optimized clone of the Respiratory Syncytial Virus F protein gene was obtained from Novavax Company (termed F-Nov). The sequence was based on the first sequence published for this gene (Collins, et al PNAS 81: 7683-7687, 1984). This DNA was inserted into a eukaryotic expression plasmid and transfected into avian cells as well as COS-7 cells. Very little expression was detected in avian cells. In COS-7 cells, the Fo form was the primary product although a small amount of the intermediate cleavage product was detected. However, the final cleavage product (F1) was not detected. Furthermore, very little of the expressed protein was detected on cell surfaces, a result consistent with the failure to detect efficient cleavage. This phenotype is characteristic of a mutant glycoprotein that is defective in folding and, as a result, is retained in intracellular compartments.

Example 2

RSV F-LM Protein is Expressed on the Cell Surface of Eukaryotic Cells

Cells were transfected with cDNAs encoding the F protein gene from Novavax (codon optimized) (F-Nov). Another plate of cells was transfected with RSV F-LM cDNA clone of FIG. 3. Both clones of the RSV F were also used to construct chimera proteins containing the ectodomain of the RSV F genes and the cytoplasmic tail and transmembrane domain of the NDV F protein (F-Nov/NDV F and F-LM/NDV F). Expression is shown in FIG. 4. FIG. 4 shows that the F protein directed by the F-LM gene is cleaved, in contrast to the F protein directed by the codon optimized F protein cDNA (F-Nov). Furthermore, a chimera constructed with the ectodomain of the F-LM and the NDV transmembrane and cytoplasmic tail domains is also expressed and cleaved.

Example 3

Production of Respiratory Syncytial Virus VLP Vaccine

This example presents a protocol for production of VLP vaccines containing Respiratory Syncytial Virus (RSV) sequences.

Vectors:

RSV cDNA sequences encoding NP (i.e., for example, GenBank # U07233), M (i.e., for example, GenBank # U02470 or, alternatively, M2-1), G (i.e., for example, GenBank # U92104), and the invention's RSV F (such as RSV F-LM) protein are subcloned into the expression vector pCAGGS to generate pCAGGS-NP, pCAGGS-M2-1, pCAGGS-G and pCAGGS-F-R108N/R109N, respectively. In one embodiment, the cDNA encoding the RSV F protein may be mutated to eliminate one of the two furin recognition sites at amino acids 106-109 and 131-136, as previously reported (Gonzalez-Reyes, et al, PNAS 98: 9859). Elimination of cleavage inhibits the ability of the F protein to fuse. The absence of cell-cell fusion may increase the release of VLPs. In one embodiment, a double mutation, R108N/R109N, eliminates one cleavage and inhibits the fusion activity of the protein (Gonzalez-Reyes, et al, PNAS 98: 9859). Additional RSV proteins not found in other paramyxoviruses are NS1, NS2, M2-2, and SH, but all have been shown to be nonessential for virus assembly (reviewed in Collins, et al, Respiratory Syncytial Virus, in Fields Virology, Ed. Knipe, D. and Howley, P. Lippincott Williams and Wilkins, 2001). G protein is also nonessential for assembly but likely contributes to a protective immune response to the virus.

Cell Lines:

RSV grows efficiently in a variety of cell lines from human and animal sources. However, HEp-2 cells (a Hela cell variant) are used since they are the most efficient in production of virus (reviewed in Collins, et al, Respiratory Syncytial Virus, in Fields Virology, Ed. Knipe, D. and Howley, P. Lippincott Williams and Wilkins, 2001). A549 cells (type II alveolar epithelial lung carcinoma cells) are also used as they are reported to be permissive for RSV.

Transfection, Infection and Metabolic Labeling:

Transfections of sub confluent cells is accomplished using Lipofectamine (Invitrogen) as recommended by the manufacturer. The following amounts of plasmid DNA are used per 35 mm dish: 1.0 μg pCAGGS-NP, 1.0 μg pCAGGS-M2-1, 0.75 μg pCAGGS-F-R108N/R109N, and 1.0 μg pCAGGS-G. A total of 3.75 μg of plasmid DNA per 35 mm plate is used in transfection experiments. When only one, two, or three cDNAs are used, the total amount of transfected DNA is kept constant by adding vector pCAGGS DNA. For each transfection, a mixture of DNA and 5 μl of Lipofectamine in OptiMEM media (Gibco/Invitrogen) is incubated at room temperature for 45 minutes, and added to cells previously washed with OptiMEM. The cells are incubated for 5 hours, the Lipofectamine-DNA complexes removed, and 2 ml of supplemented DMEM added. After 36 hours, the medium is replaced with 0.7 ml DMEM without cysteine and methionine and supplemented with 100 μCi of $^{35}$S-methionine and $^{35}$S-cysteine mixture (NEG-772 EASYTAG™ Express Protein Labeling Mix, $^{35}$S, Perkin Elmer Life Sciences Inc.). After 4 hours of pulse label, one set of transfected plates is lysed, while in another set the medium is replaced with 1.0 ml of supplemented DMEM with 0.1 mM cold methionine (Nutritional Biochemicals Corporation). After 8 hours of chase, the medium is collected. In addition, the cells are sonicated to release cell associated VLPs. The resulting cell supernatants are combined. The cells are lysed in 0.5 ml lysis buffer (10 mM NaCl, 1.5 mM $MgCl_2$, 10 mM Tris-HCl, pH 7.4) containing Triton-DOC (1% Triton, 1% sodium deoxycholate) and 1.25 mg N-ethylmaleimide (NEM). Cells are harvested with a cell scraper and homogenized by passing through a 26-gauge needle 10 to 15 times.

To determine if the VPS pathway is involved in VLP budding, sub confluent HEp-2 cells are simultaneously transfected with pCAGGS-M2-1 and different concentrations of either pBJ5-Vps4-E228Q-Flag or pDsRed2-N1-CHMP3. Corresponding empty vectors are used as control. Cells are incubated for 36 hours and the same pulse-chase protocol was performed as described above. To generate virus particles for controls, cells are infected at an MOI of 10 pfu for 30 hours and labeled with $^{35}$S-methionine and $^{35}$S-cysteine mixture for 4 hours, and chased in nonradioactive medium for 8 hours as described above. Cell supernatant are harvested and virions purified as described below. Cells are lysed and homogenized.

Virus and VLP Purification:

VLPs as well as virions are purified from cell supernatants in protocols previously developed for virus purification. The cell supernatants are clarified by centrifugation at 5000 rpm for 5 min at 4° C., overlaid on top of a step gradient consisting of 3.5 ml 20% and 0.5 ml 65% sucrose solutions in TNE buffer (25 mM Tris-HCl pH 7.4, 150 mM NaCl, 5 mM EDTA), and centrifuged at 40,000 rpm for 12 hours at 4° C. using a SW50.1 rotor (Beckman). The interface (containing concentrated particles) is collected in 0.5 ml, mixed with 2.0 ml of 80% sucrose, and overlaid on top of 1.0 ml 80% sucrose cushion. Additional layers of sucrose (1.0 ml of 50% and 0.5 ml of 10% sucrose) are layered on top of the sample. The gradient is centrifuged at 38,000 rpm for 20 h at 4° C. The gradient is collected from the bottom into one 1 ml fraction and eight 0.5 ml fractions using a polystaltic pump. Densities of each fraction are determined using a refractometer. VLPs derived from expression of all combinations of proteins are prepared in a single experiment, thus enabling direct comparison of results.

Immunoprecipitation and Polyacrylamide Gel Electrophoresis:

Immunoprecipitation is accomplished by combining one volume of cell lysate or sucrose gradient fraction with two volumes of TNE buffer. Samples are incubated with RSV specific polyclonal antibodies for 16 hours at 4° C. Antiserum to be used is commercially available from several sources. Immune complexes (ICs) are adsorbed to Protein A (Pansorbin Cells, CALBIOCHEM) for 2 hours at 4° C., pelleted, and then washed three times in immunoprecipitation (IP) wash buffer (phosphate buffer saline (PBS) containing 0.5% Tween-20 and 0.4% sodium dodecyl sulfate (SDS)). ICs are resuspended in SDS-polyacrylamide gel electrophoresis sample buffer (125 mM Tris-HCl, pH 6.8, 2% SDS, 10% glycerol, 0.4% Bromphenol blue) with 1 M β-mercaptoethanol (BME) and boiled. Proteins are separated on 8% polyacrylamide-SDS gel and subjected to autoradiography. Quantification of resulting autoradiographs is accomplished using a Fluor-S™ MultiImager (BioRad).

Example 4

Figure 6:
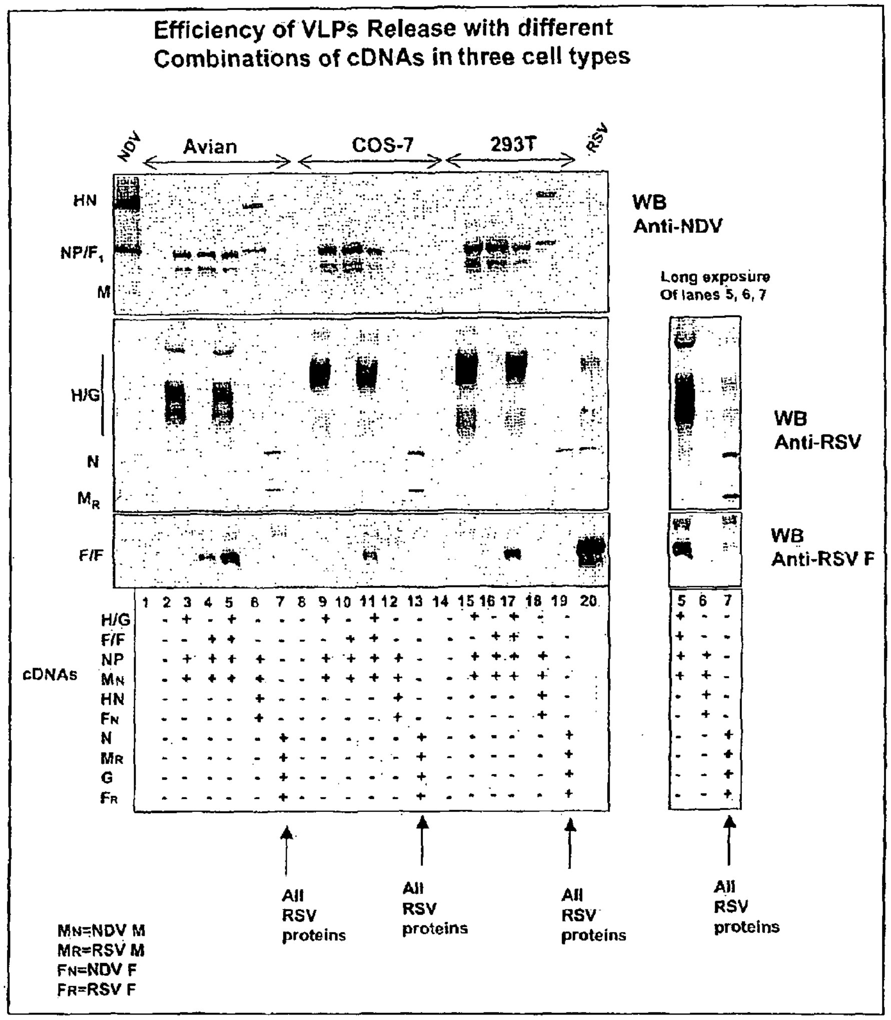
FIG. 6: Efficiency of VLP Release from different cells with different combinations of expressed proteins. Different combinations of cDNA were transfected into avian, COS-7, or 293T cell monolayers in parallel. VLPs were purified and proteins in the VLPs were detected by Western Blots. The top panel shows NDV proteins (antibody detects only NDV NP and HN protein but levels of NP indicate efficiency of formation of particles), the middle panel shows results with anti-RSV antibody (which detects RSV G, NP, and M), and the bottom panel shows results with an anti-RSV F protein antibody.

Efficiency of VLP Release from Different Cells with Different Combinations of Expressed Proteins To compare efficiency of release from different cell types and with different combinations of cDNAs, avian, COS-7 and 293T cell monolayers were transfected, in parallel, with different combinations of cDNAs, indicated at the bottom of FIG. 6. VLPs were purified and proteins in the VLPs were detected by Western Blots. The top panel shows NDV proteins (antibody detects only NDV NP and HN protein but levels of NP indicate efficiency of formation of particles), the middle panel shows results with anti-RSV antibody (which detects RSV G, NP, and M), and the bottom panel shows results with an anti-RSV F protein antibody.

The data show that RSV F protein chimera (F/F) is incorporated into ND VLPs in the presence of RSV H/G chimera protein with significantly higher efficiency (greater than 10 fold) than in the absence of H/G (see lanes 4 and 5, lanes 10 and 11, and lanes 16 and 17 of FIG. 6).

The data also show that incorporation of H/G and F/F into ND VLPs is significantly increased over incorporation of intact G and F proteins into VLPs formed with RSV proteins alone (see arrows).

The data additionally show that the efficiency of incorporation of F/F chimera into ND VLPs is significantly higher (from 5 to 8 fold) in VLPs released from avian cells as compared to other cell types.

Example 5

Figure 7:
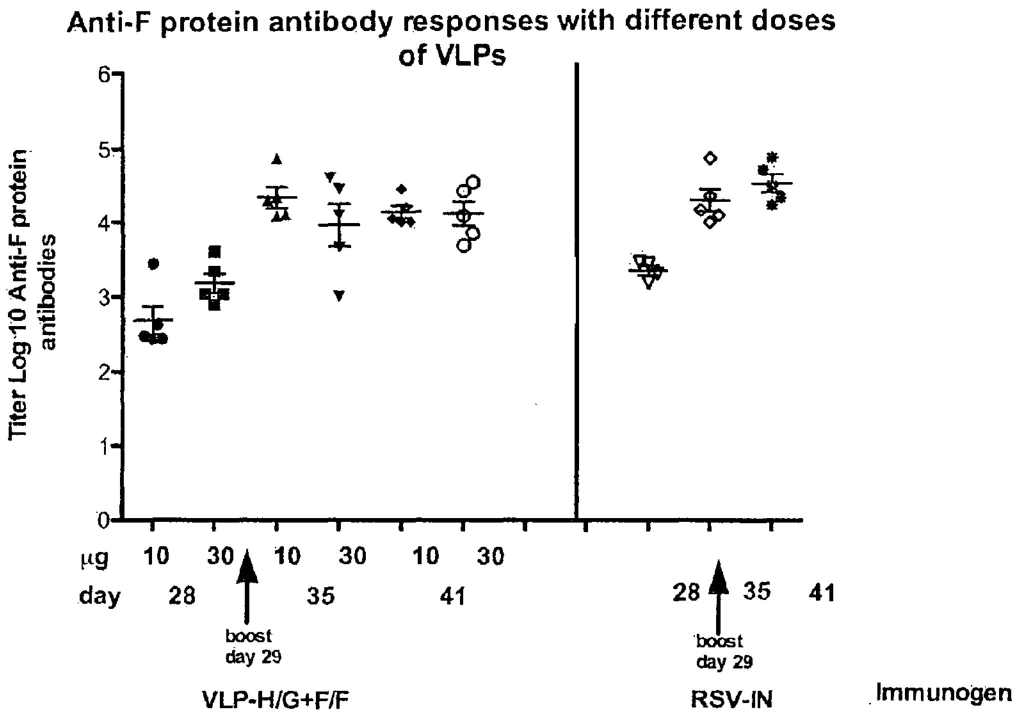
FIG. 7: Anti-F protein antibody titers with two different doses of VLP-H/G+F/F and different times after immunization. Responses after RSV infection were determined in parallel as a positive control.

Immunization with VLPS Containing Both the H/G and F/F Chimera Proteins a. Antibody Responses Mice were immunized with different amounts of VLP-H/G+F/F. ELISA, using purified F protein as target antigen, determined anti-F protein antibody responses with time after immunization. FIG. 7 shows antibody titers with time after immunization and with two different doses of VLPs. Responses after RSV infection were determined in parallel as a positive control.

The data show that anti-F protein antibody responses (i.e., the amount of titer log 10) after VLP immunization were robust and comparable to responses to live virus.

The data further show that anti-F protein responses (i.e., the amount of titer log 10) using smaller doses of antigen (10 micrograms) were quite robust.

The data additional show that anti-F protein responses (i.e., the amount of titer log 10) were increasing at time and boost immunization enhanced responses.

Figure 8:
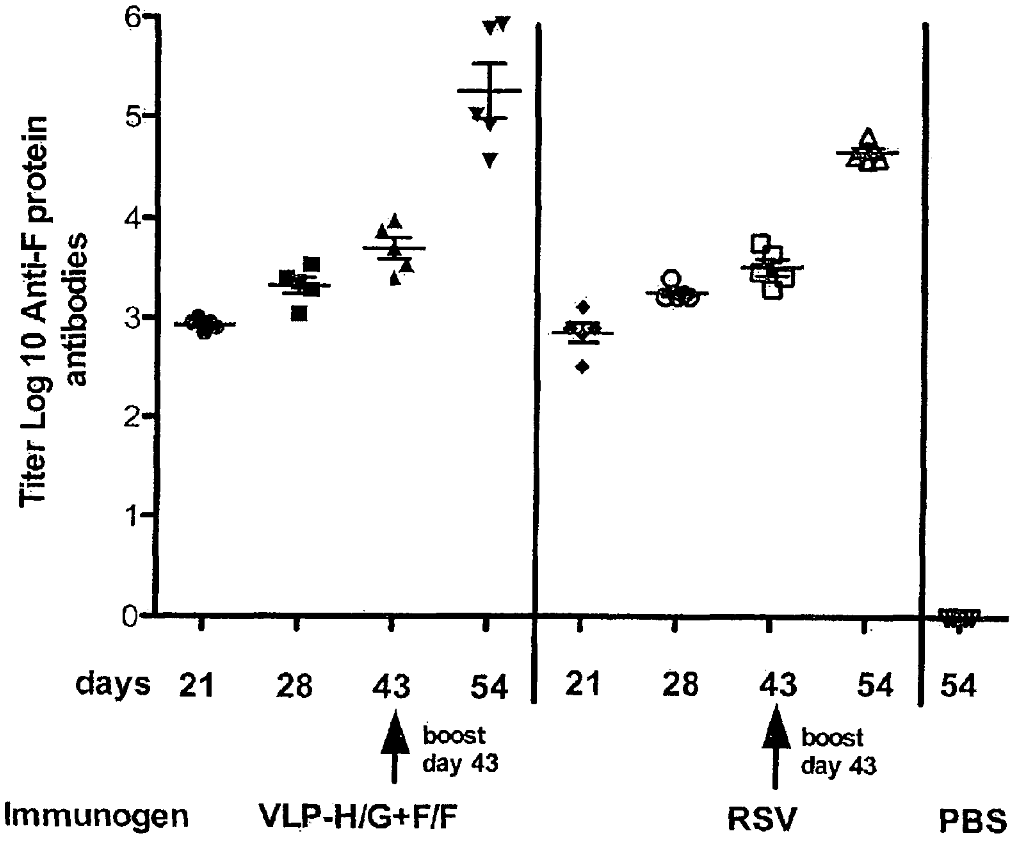
FIG. 8: Anti-F protein antibody titers over time following immunization with VLP-H/G+F/F. Responses after RSV infection were determined in parallel as a positive control, and after treatment with PBS as negative control.

FIG. 8 shows a separate experiment in which durability of antibody responses (i.e., the amount of titer log 10) was investigated. FIG. 8 shows that anti-F protein antibody responses (i.e., the amount of titer log 10) were increasing at 43 days post immunization. A boost significantly enhanced responses (i.e., the amount of titer log 10).

b. Neutralizing Antibody Responses

Figure 9:
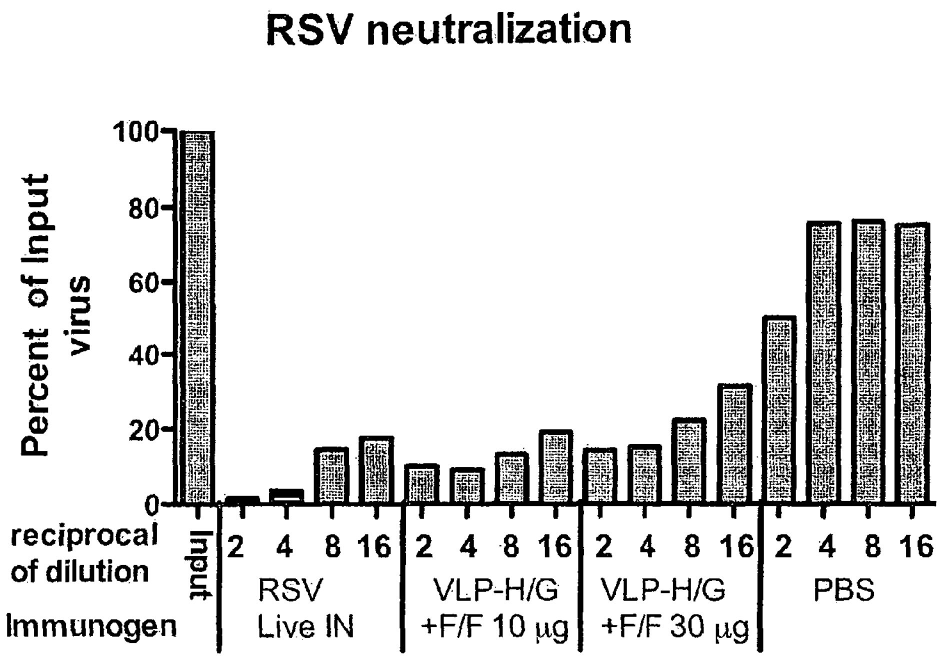
FIG. 9: RSV neutralization in an in vitro plaque reduction assay. Mice were immunized with VLP-H/G+F/F or live RSV (positive control). Sera from immunized mice were tested for their ability to neutralize infectious RSV virus. The reduction of virus titer with each dilution is shown.

To determine if the antibody responses to VLP-H/G+F/F were neutralizing, the ability of sera from immunized mice to neutralize virus in an in vitro plaque reduction assay was determined. FIG. 9 shows results of an exemplary experiment. Sera from mice were pooled and increasing dilutions of the pooled sera were incubated with infectious virus. The reduction of virus titer with each dilution is shown. Sera from VLP immunized mice were as effective in virus neutralization as sera from mice infected with live RSV.

Example 6

Protection of VLP-H/G+F/F Immunized Mice from RSV Challenge

Figure 10:
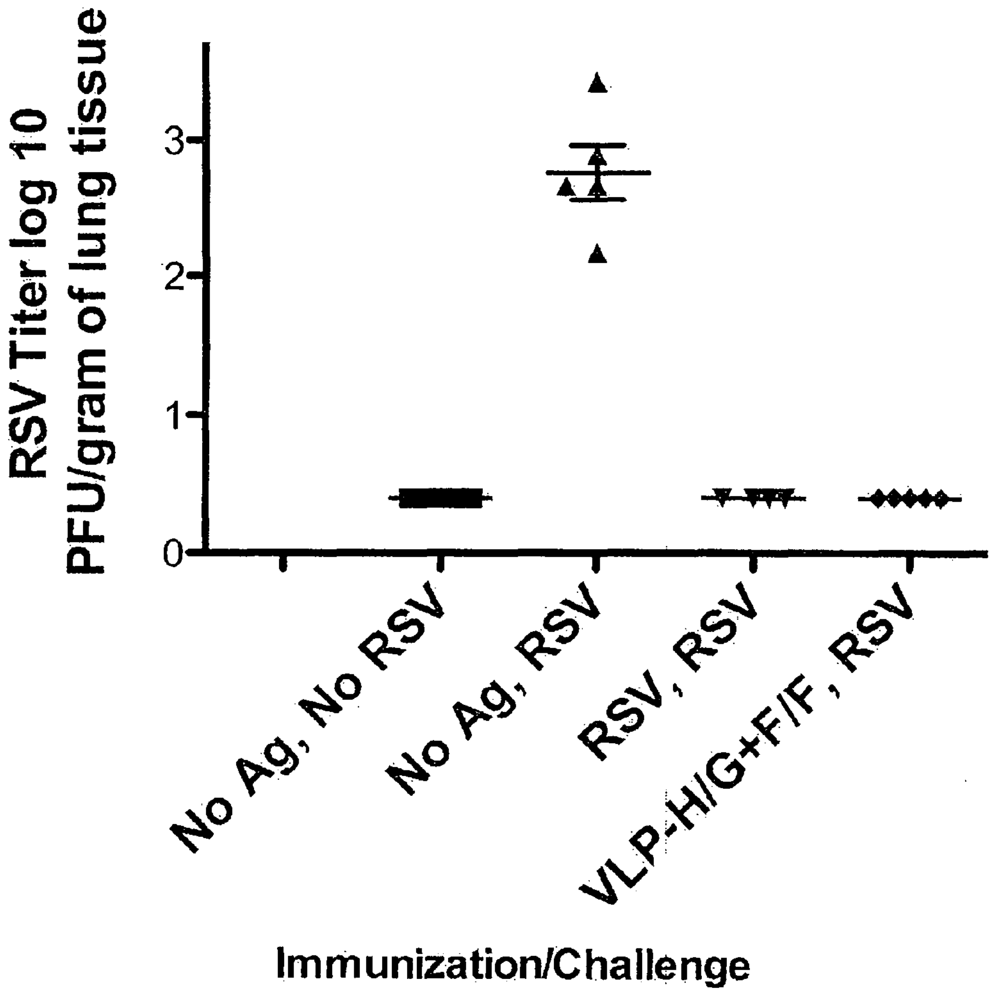
FIG. 10: Virus titer in lungs of control mice and mice immunized with VLP-H/G+F/F.

Mice were immunized with VLP-H/G+F/F and, without a boost, were challenged with live RSV. FIG. 10 shows virus titer in lungs of control and immunized mice. The data show that the VLP immunized mice were completely protected from RSV replication in lungs.

Example 7

Figure 11:
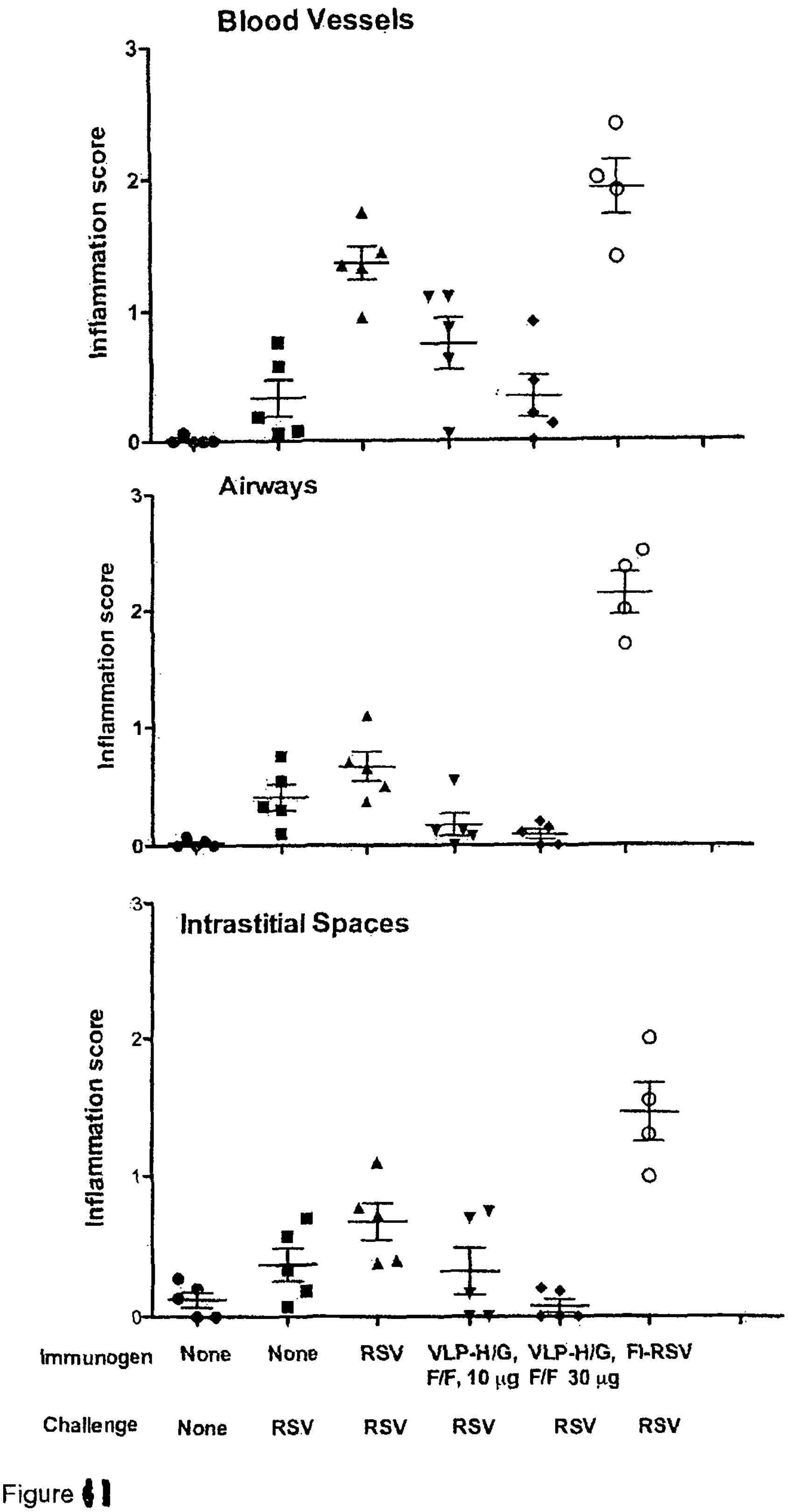
FIG. 11: Immunopathology, groups of mice were immunized with two different doses of VLP-H/G+F/F (10 and 30 micrograms), boosted with 10 micrograms of VLPs and then challenged with infectious RSV. After 6 days, the lungs of mice were removed, sectioned, stained with H and E, and examined for inflammation typical of the enhanced pathology seen in lungs of FI-RSV immunized mice.

Absence of Enhanced Pathology in VLP-H/G+F/F Vaccinated Mice after RSV Challenge A vaccine for RSV preferably shows evidence of reduced (preferably absent) immunopathology that is typical of that observed with the formaldehyde treated RSV (FI-RSV) tested many years ago. To assay for immunopathology, groups of mice were immunized with two different doses of VLP-H/G+F/F (10 and 30 micrograms), boosted with 10 micrograms of VLPs and then challenged with infectious RSV. After 6 days, the lungs of mice were removed, sectioned, stained with H and E, and examined for inflammation typical of the enhanced pathology seen in lungs of FI-RSV immunized mice. FIG. 11 shows results of blind scoring of the lung sections.

The data show that VLP-H/G+F/F immunized mice showed no evidence of immunopathology. Indeed, inflammation in immunized mice was reduced over RSV immunized mice and the reduction in inflammation was enhanced at higher doses of VLPs. The positive control mice, immunized with FI-RSV, showed the expected pathology.

Example 8

Immunization with an Alternate VLP Construction

VLP-H/G+F/HR2F a. Antibody Responses Measured by ELISA

Figure 12:
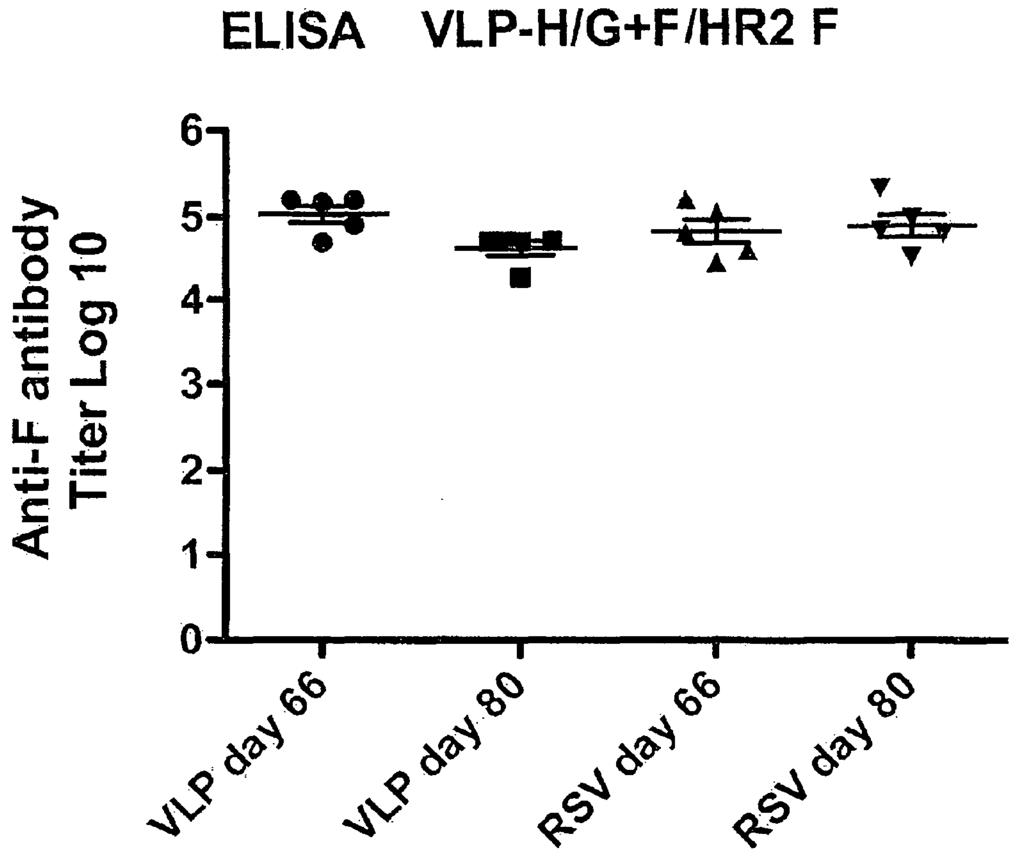
FIG. 12: Anti-F antibody titers measured by ELISA. Mice were immunized with infectious RSV or with 30 micrograms total VLP-H/G+F/HR2F protein and then boosted with 10 micrograms total VLP-H/G+F/HR2F protein at day 52. Sera were collected at day 66 and day 80 and anti-F protein antibody responses were determined by ELISA using purified F protein as target antigen.

Mice were immunized with 30 micrograms total VLP-H/G+F/HR2F protein and then boosted with 10 micrograms total VLP-H/G+F/HR2F protein at day 52. Sera were collected at day 66 and day 80 and anti-F protein antibody responses were determined by ELISA using purified F protein as target antigen. FIG. 12 shows that anti-F protein antibody titers were quite robust and comparable to those obtained from sera from mice infected with live RSV, even at 80 days. These results suggest that responses were quite durable.

b. Neutralizing Antibody Responses

Figure 13:
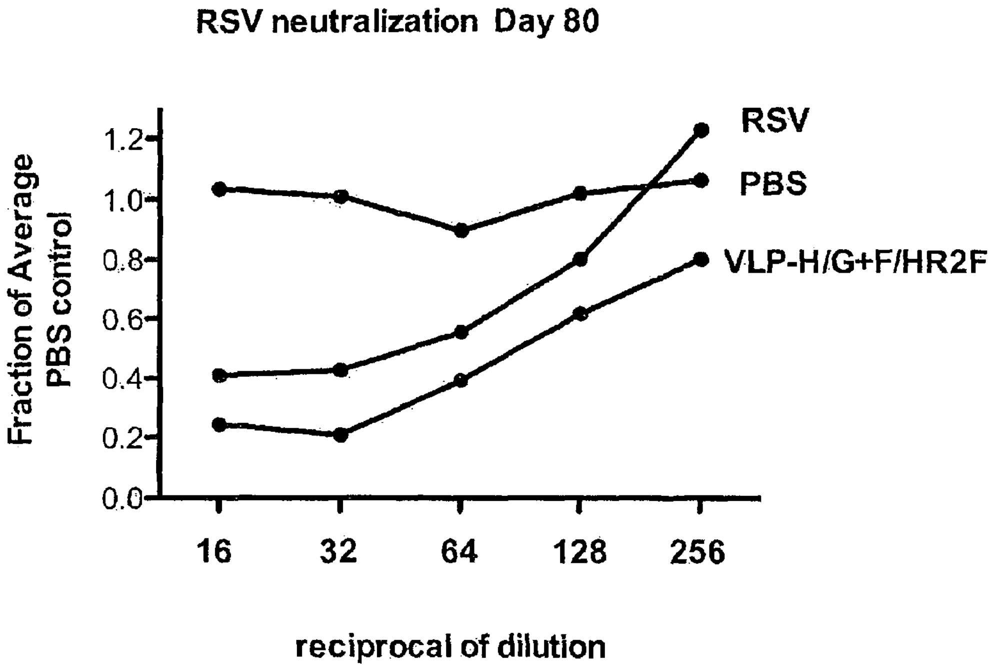
FIG. 13: Neutralizing antibody responses against RSV in an in vitro plaque reduction assay. Mice were immunized with infectious RSV or with 30 micrograms total VLP-H/G+F/HR2F protein and then boosted with 10 micrograms total VLP-H/G+F/HR2F protein at day 52. Sera from immunized mice (day 80) were pooled and increasing dilutions of the pooled sera were incubated with infectious virus. The reduction of virus titer with each dilution is shown.

To determine if the antibody responses to VLP-H/G+F/HR2F were neutralizing, the ability of sera from immunized mice to neutralize virus in an in vitro plaque reduction assay was determined. FIG. 13 shows results of a typical experiment. Sera from mice (day 80) were pooled and increasing dilutions of the pooled sera were incubated with infectious virus. The reduction of virus titer with each dilution is shown. Surprisingly, sera from VLP-H/G+F/HR2F immunized mice were more effective in virus neutralization than sera from mice infected with live RSV.

The data in FIGS. 6-13 demonstrate that VLPs containing both the RSV G protein and F protein ectodomains stimulate robust, neutralizing, and protective anti-F protein antibody responses in the absence of immunopathology. These properties are hallmarks of a immunologically effective RSV vaccine.

Example 9

Efficacy of VLP-H/Ga as a Vaccine in Preclinical Trials

The ND VLPs containing the HN/Ga chimera protein were further tested in mice for their ability to protect mice from respiratory syncytial virus (RSV) infection. The goals of the new experiments were to determine if intramuscular (IM) inoculation could provide protection and to determine if a single dose of VLP-H/Ga could provide protection. IM inoculation mimics the route of delivery of most human vaccines.

The protocol was to inject mice in the muscle of the hind leg with 10 or 40 □g total VLP protein. Negative controls were mice receiving buffer. Positive controls were mice receiving live RSV via intranasal infection ($3\times10^6$ pfu/mouse). In addition, a group of mice received formaldehyde treated virus (FI-RSV), intramuscularly. FI-RSV mimics the original vaccine virus that resulted in enhanced disease many years ago. This was a positive control for abnormal immune responses after vaccination with RSV.

Figure 14:
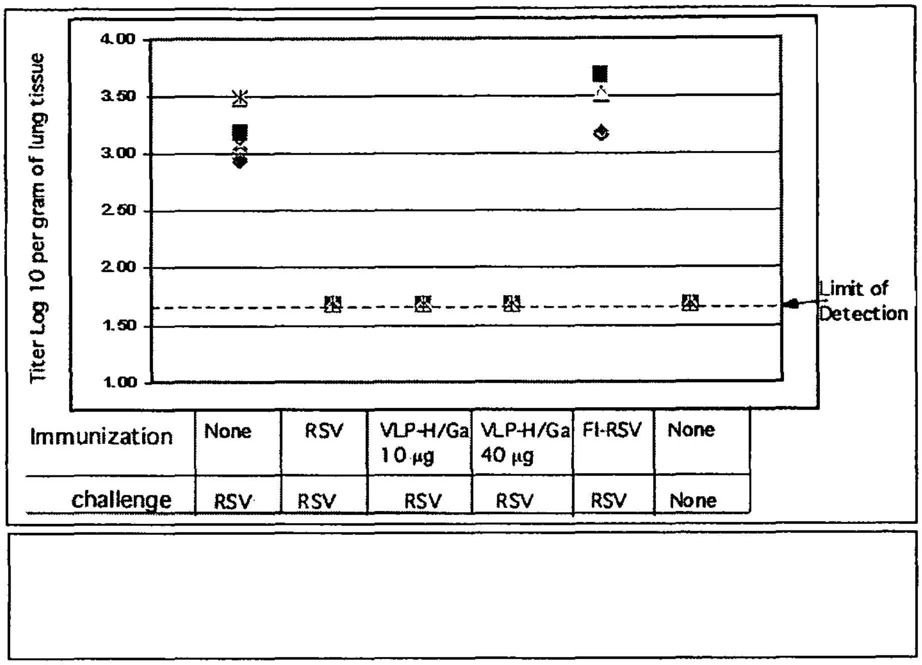
FIG. 14: Protection of Mice from RSV replication by immunization with a single dose of VLP-H/Ga. Virus Titers in lungs after challenge. Groups of 5 mice were immunized as indicated at the bottom of the figure. The mice were challenged with live RSV. Four days after challenge the virus titer in the lungs was determined by plaque assay.

At 32 days post injection, mice were infected by intranasal inoculation with live RSV ($1.5\times10^6$ pfu/mouse). Four days later, mice were sacrificed and the titers of RSV in the lungs were determined. FIG. 14 shows the results. The figure shows that RSV replicated in the lungs of mice not previously vaccinated. RSV also replicated in lungs of mice immunized with FI-RSV. As expected, RSV did not replicate in mice receiving live RSV as a vaccine. Significantly, RSV did not replicate in mice immunized with a single dose of either concentration of VLP-H/Ga.

Conclusions:

(a) IM immunization protected mice from RSV replication in lungs upon challenge with live RSV, (b) Immunization with as little as 10 μg total VLP-Ga protein protected mice from challenge, and (c) A single dose of immunogen protected mice from challenge.

Example 10

Incorporation of RSV F Protein into ND VLPs

RSV encodes two surface glycoproteins, the G protein and the F or fusion protein. A vaccine for RSV would optimally also include the RSV F protein. The inventor hypothesized that the F protein of RSV can be incorporated into ND VLPs and these particles can be used to stimulate protective immune responses in a murine model system.

A. Construction of ND VLPs Containing the RSV F Protein Ectodomain

Figure 15:
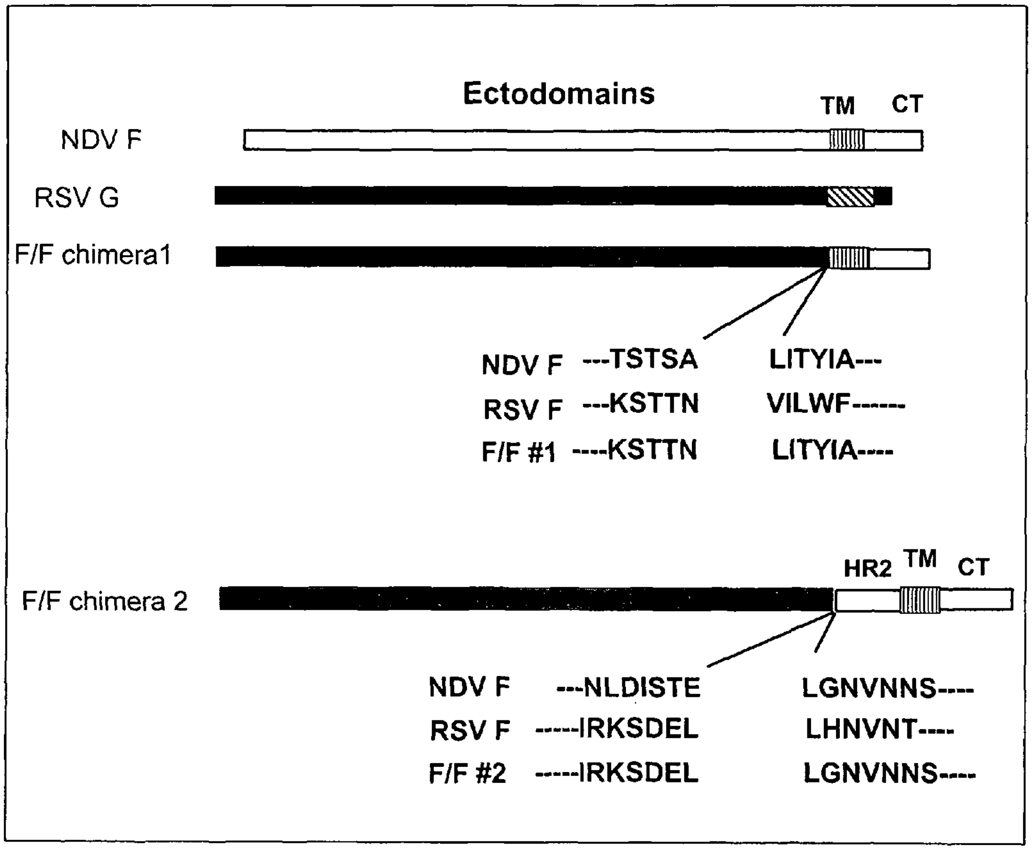
FIG. 15: Sequences at the fusion junction between RSV F sequences and NDV F sequences. F/F #1 is the same as F/F chimera F/F#2 is the same as F/HR2F chimera

To incorporate the RSV F protein into ND VLPs, two chimera protein genes were constructed. In one chimera, the transmembrane (TM) and the cytoplasmic (CT) domains of the NDV F protein was fused, in frame, to the ectodomain of the RSV F protein using standard recombinant DNA protocols (F/F chimera #1). (The F protein cDNA used in the constructions was the F-LM clone generated in the Morrison laboratory). In a second chimera, the HR2, the TM, and the CT domains of the NDV F protein was fused in frame with the ectodomain of the RSV F protein (F/F chimera #2 or F/HR2F). A diagram of the fusion junctions of the two chimera proteins is shown in FIG. 15. The nucleic acid sequences of the chimera proteins are shown in FIG. 16 and FIG. 17. The amino acid sequences of the chimera proteins are shown in FIG. 18.

B. Incorporation of Chimera F Protein into ND VLPs

Figure 19:
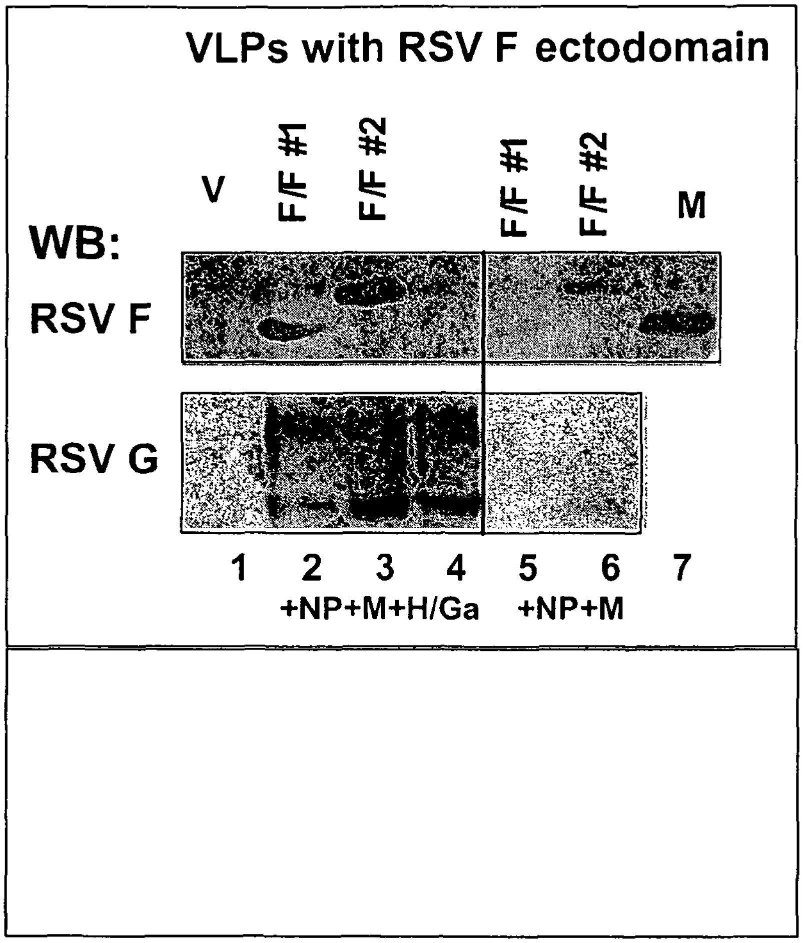
FIG. 19: Incorporation of F/F chimera proteins into VLPs. Incorporation of RSV F protein ectodomain into VLPS. Avian cells were transfected with cDNAs indicated at top and bottom of the figure. VLPs were harvested, purified, and the proteins in the purified particles were electrophoresed on polyacrylamide gels. The proteins in VLPs were detected by Western blots (WB) of the gels using antibodies for the RSV F or the RSV G proteins. M, marker F protein. V, vector DNA.

Avian cells were transfected with cDNAs encoding the NDV membrane protein (M), the NDV NP protein, and, separately, the chimera RSV F/NDV F proteins. In another set of cultures, cells were transfected with the cDNAs encoding the NP and M proteins as well as the cDNAs encoding the HN/Ga chimera protein and the cDNAs encoding the F chimera proteins. VLPs were purified by our standard protocols. FIG. 19 shows a Western blot of a polyacrylamide gel containing the proteins present in the VLPs. The RSV proteins were detected.

The figure shows that both the F chimera proteins are incorporated into VLPs (lanes 5 and 6). The F/HR2F chimera is more efficiently incorporated than the F/F chimera. Significantly, the figure also shows that the incorporation of both the F chimera proteins into VLPs is significantly enhanced by the presence of the HN/Ga chimera protein (compare lanes 2 and 3 with lanes 5 and 6).

Conclusions:

(a) The ectodomain of the RSV F protein can be incorporated into VLPs based on NDV structural proteins, (b) Co-expression of the HN/Ga chimera enhances incorporation of the chimera F proteins, and (c) These results indicate that a single VLP with both RSV glycoprotein ectodomains may be easily constructed. This VLP, used as a vaccine, should provide maximal protection from RSV disease.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

The invention claimed is:

1. A recombinant polypeptide sequence comprising RSV F-LM protein ectodomain SEQ ID NO:16.

2. A recombinant polypeptide sequence comprising a first polypeptide having at least 95% identity to RSV F protein ectodomain polypeptide SEQ ID NO:16, wherein the first polypeptide comprises at least one of (a) lysine at a position corresponding to amino acid 66 of SEQ ID NO:16, (b) glutamine at a position corresponding to amino acid 101 of SEQ ID NO:16, and (c) valine at a position corresponding to amino acid 203 of SEQ ID NO:16.

3. A virus-like particle comprising the polypeptide of claim 1 or claim 2.

4. An immunogenic composition comprising: (a) the VLP of claim 3, and (b) at least an adjuvant, diluent or excipient.

5. A method of immunizing an animal against Respiratory Syncytial Virus (RSV), comprising administering an immunologically effective amount of the composition of claim 4 to the animal to produce an immune response.

6. The VLP of claim 3, wherein said VLP further comprises a second polypeptide containing Newcastle Disease Virus (NDV) Matrix (M) protein.

7. The VLP of claim 6, wherein said VLP further comprises one or more RSV protein.

8. The VLP of claim 7, wherein the RSV protein comprises RSV F/HR2 polypeptide sequence.

9. The VLP of claim 8, wherein said VLP further comprises RSV H/G polypeptide sequence.

10. The VLP of claim 7, wherein the RSV protein comprises RSV F/F polypeptide sequence.

11. The VLP of claim 10, wherein said VLP further comprises RSV H/G polypeptide sequence.

12. The VLP of claim 6, wherein said VLP further comprises one or more NDV proteins.

13. The VLP of claim 12, wherein said VLP further comprises a NDV cytoplasmic protein sequence selected from the group consisting of NDV Nucleocapsid (NP) protein, cytoplasmic domain of NDV Fusion (F) protein, and cytoplasmic domain of NDV heamagglutinin-neuraminidase (HN) protein.

14. The VLP of claim 12, wherein said VLP further comprises a NDV transmembrane protein sequence selected from the group consisting of NDV Fusion (F) protein transmembrane domain, and heamagglutinin-neuraminidase (HN) protein transmembrane domain.

15. The VLP of claim 12, wherein said VLP further comprises RSV F/HR2 polypeptide sequence.

16. The VLP of claim 15, wherein said VLP further comprises RSV H/G polypeptide sequence.

17. The VLP of claim 12, wherein said VLP further comprises RSV F/F polypeptide sequence.

18. The VLP of claim 17, wherein said VLP further comprises RSV H/G polypeptide sequence.

* * * * *